United States Patent
Linder-Ganz et al.

(10) Patent No.: US 10,278,826 B2
(45) Date of Patent: May 7, 2019

(54) MENISCUS PROSTHETIC DEVICE SELECTION AND IMPLANTATION METHODS

(71) Applicant: Active Implants Corporation, Memphis, TN (US)

(72) Inventors: Eran Linder-Ganz, Tel Aviv (IL); Avraham Shterling, Yarkona (IL); Noam Weissberg, Rishon-Lezion (IL)

(73) Assignee: Active Implants LLC, Memphis, TN (US)

( * ) Notice: Subject to any disclaimer, the term of this patent is extended or adjusted under 35 U.S.C. 154(b) by 0 days.

(21) Appl. No.: 15/902,822

(22) Filed: Feb. 22, 2018

(65) Prior Publication Data

US 2018/0250136 A1 Sep. 6, 2018

Related U.S. Application Data

(63) Continuation of application No. 15/135,168, filed on Apr. 21, 2016, now Pat. No. 9,901,454, which is a
(Continued)

(51) Int. Cl.
*A61F 2/38* (2006.01)
*B33Y 50/00* (2015.01)
(Continued)

(52) U.S. Cl.
CPC ............ *A61F 2/3872* (2013.01); *A61B 34/10* (2016.02); *A61F 2/461* (2013.01); *A61F 2/4684* (2013.01); *B33Y 50/00* (2014.12); *A61B 2034/108* (2016.02); *A61F 2/30965* (2013.01); *A61F 2002/30014* (2013.01); *A61F 2002/30064* (2013.01); *A61F 2002/30065* (2013.01); *A61F 2002/30069* (2013.01); *A61F 2002/3093* (2013.01); *A61F 2002/30329* (2013.01); *A61F 2002/30563* (2013.01); *A61F 2002/30565* (2013.01); *A61F 2002/30616* (2013.01); *A61F 2002/30673* (2013.01); *A61F 2002/30841* (2013.01); *A61F 2002/30884* (2013.01); *A61F 2002/30906* (2013.01); *A61F 2002/30945* (2013.01); *A61F 2002/30948* (2013.01); *A61F 2002/30955* (2013.01); *A61F 2002/30957* (2013.01); *A61F 2002/30983* (2013.01);
(Continued)

(58) Field of Classification Search
CPC ........... A61B 5/4514; A61B 2017/0646; A61F 2/3603; A61F 2/4618; A61F 2/3872
See application file for complete search history.

(56) References Cited

U.S. PATENT DOCUMENTS 5,944,759 A * 8/1999 Link .................... A61F 2/30965
623/18.11

* cited by examiner

*Primary Examiner* — Jason-Dennis N Stewart
(74) *Attorney, Agent, or Firm* — Haynes and Boone, LLP

(57) ABSTRACT

Methods of selecting and implanting prosthetic devices for use as a replacement meniscus are disclosed. The selection methods include a pre-implantation selection method and a during-implantation selection method. The pre-implantation selection method includes a direct geometrical matching process, a correlation parameters-based matching process, and a finite element-based matching process. The implant identified by the pre-implantation selection method is then confirmed to be a suitable implant in the during-implantation selection method. Methods of implanting meniscus prosthetic devices are also disclosed.

17 Claims, 22 Drawing Sheets

Related U.S. Application Data continuation of application No. 13/194,787, filed on Jul. 29, 2011, now Pat. No. 9,326,863, which is a continuation of application No. 12/100,115, filed on Apr. 9, 2008, now Pat. No. 7,991,599.

(51) Int. Cl.
*A61F 2/46* (2006.01)
*A61B 34/10* (2016.01)
*B33Y 80/00* (2015.01)
*A61F 2/30* (2006.01)

(52) U.S. Cl.
CPC .............. *A61F 2002/3895* (2013.01); *A61F 2210/0071* (2013.01); *A61F 2220/0008* (2013.01); *A61F 2220/0025* (2013.01); *A61F 2240/008* (2013.01); *A61F 2250/0018* (2013.01); *A61F 2250/0064* (2013.01); *B33Y 80/00* (2014.12)

| PARAMETER: | AREA (A) | WIDTH (W) | LENGTH (L) | PERIMETER (PR) | CORONAL RELATION (C) |
|---|---|---|---|---|---|
| DEFINITION: | MENISCUS CONTACT AREA/ TIBIA MEDIAL AREA | MENISCUS WIDTH/ MEDIAL TIBIA WIDTH | MENISCUS LENGTH/ TIBIA LENGTH | MENISCUS PERIMETER/ MEDIAL TIBIA PERIMETER | MENISCUS WIDTH/ CORONAL TIBIA WIDTH |
| | $\dfrac{MA}{TMA}$ | ** $\dfrac{MW_{avg}}{TMW}$ | $\dfrac{MML}{TML}$ | $\dfrac{MP}{TMP}$ | $\dfrac{MW}{TPW}$ |

**$MW_{avg} = (MWA + MWP)/2$

Fig. 15

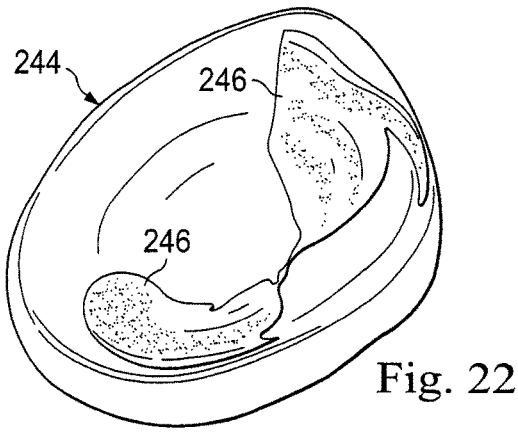
Fig. 22
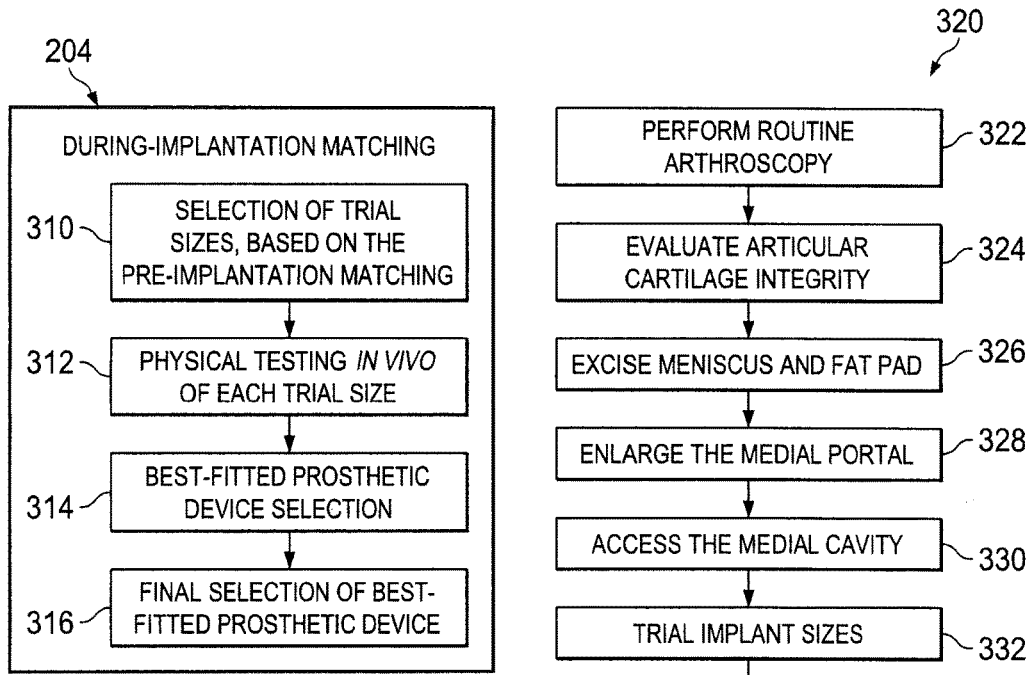
Fig. 23
Fig. 24

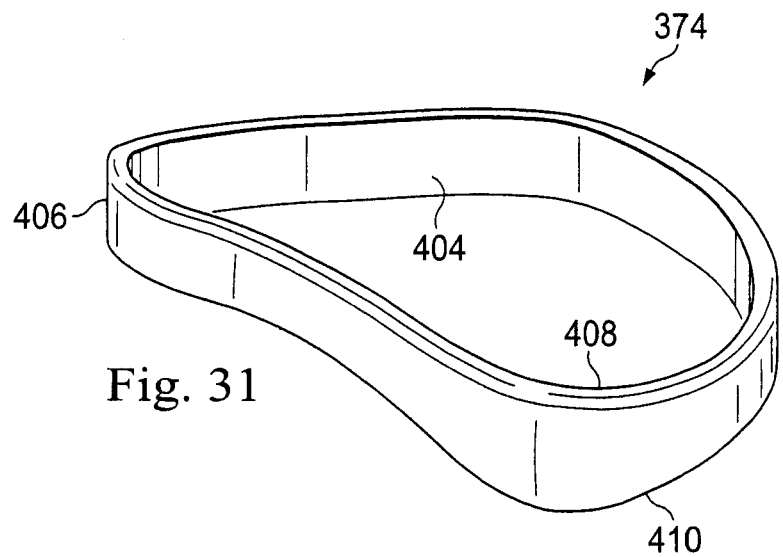
Fig. 31
| BODY WEIGHT | <60 Kg | 60-110 Kg | >110 Kg |
|---|---|---|---|
| LOW ACTIVITY | 0.1-0.3% | 0.1-0.4% | 0.2-0.6% |
| MODERATE ACTIVITY | 0.2-0.4% | 0.2-0.4% | 0.4-0.8% |
| HIGH ACTIVITY | 0.3-0.6% | 0.3-0.6% | 0.6-1.2% |
Fig. 32
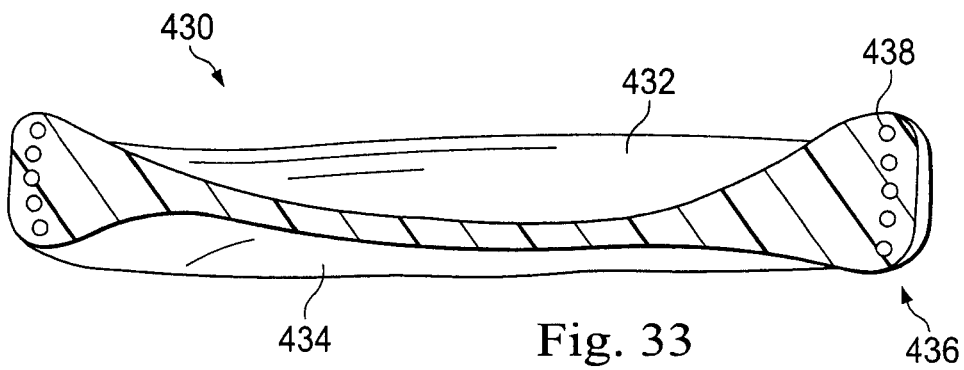
Fig. 33

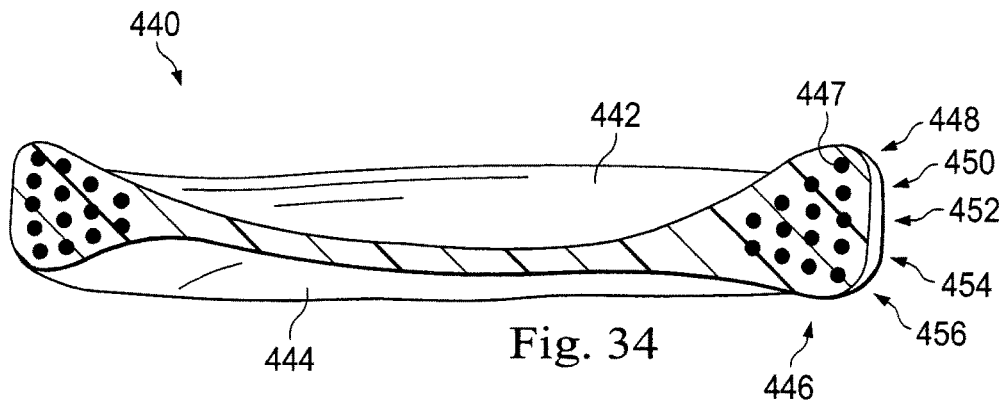
Fig. 34
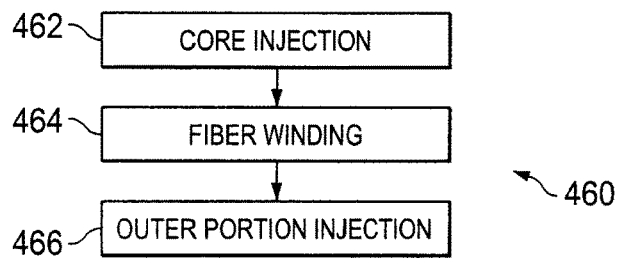
Fig. 35
| SAMPLE | TITER (dtex) | F-max (N) | TENACITY (cN/dtex) | TENSION DURING WINDING (N) |
|---|---|---|---|---|
| TO 9496-1 | 221 | 78 | 35.2 | 8.0 |
| TO 9496-2 | 226 | 77 | 34.1 | 8.0 |
| TO 9496-3 | 218 | 78 | 36.0 | 8.0 |
| TO 9402-1 | 54 | 20.9 | 38.7 | 2.0 |
| TO 9402-2 | 99 | 36.3 | 36.8 | 4.0 |
| TO 9402-3 | 228 | 82.7 | 36.3 | 8.0 |
| TO 9402-4 | 197 | 69.8 | 35.4 | 7.0 |
| TO 9402-5 | 219 | 65.1 | 29.7 | 7.0 |
| TO 9402-6 | 213 | 72.1 | 33.8 | 7.0 |
Fig. 36

MENISCUS PROSTHETIC DEVICE SELECTION AND IMPLANTATION METHODS

CROSS-REFERENCE TO RELATED APPLICATIONS

This application is a continuation of U.S. application Ser. No. 15/135,168, filed Apr. 21, 2016, now U.S. Pat. No. 9,901,454, which is a continuation of U.S. application Ser. No. 13/194,787, filed Jul. 29, 2011, now U.S. Pat. No. 9,326,863, which is a continuation of U.S. application Ser. No. 12/100,115, filed Apr. 9, 2008, now U.S. Pat. No. 7,991,599, the entireties of which are hereby incorporated by reference herein.

BACKGROUND

The present disclosure generally relates to medical prosthetic devices, systems, and methods. More specifically, in some instances the present disclosure relates to prosthetic devices that replace at least part of the functionality of the natural meniscus. Each knee has two menisci, a lateral meniscus and a medial meniscus. Each meniscus is a crescent-shaped fibrocartilaginous tissue attached to the tibia at an anterior and a posterior horn. Damage to the meniscus can cause pain and arthritis. Accordingly, in some instances it is desirable to replace the damaged natural meniscus with a prosthetic device. In some instances the prosthetic devices of the present disclosure are configured to be surgically implanted into a knee joint to replace or augment the natural meniscus. It is important that the prosthetic device be of the appropriate size and functionality for the intended patient. In some instances the methods of the present disclosure identify suitable prosthetic devices for use with a particular patient.

While existing devices, systems, and methods have attempted to address these issues, they have not been satisfactory in all respects. Accordingly, there is a need for the improved devices, systems, and methods in accordance with the present disclosure.

SUMMARY

In one embodiment, a meniscus prosthetic device is disclosed.

In another embodiment, a prosthetic device for replacing a damaged meniscus is disclosed. The prosthetic device comprises a central portion having an upper surface for engagement with a portion of a femur and an opposing lower surface for engagement with a portion of a tibia. The central portion comprises a resilient material. The prosthetic device also includes an outer portion surrounding the central portion and having an increased thickness relative to the central portion. The outer portion comprises the resilient material and tensioned with at least one reinforcing fiber embedded in the resilient material. The outer portion is sized and shaped such that a compression force imparted on the prosthetic device by the femur and the tibia urges the outer portion radially outward from the central portion.

In another embodiment, a meniscus prosthetic device for use in a knee joint is disclosed. The meniscus prosthetic device comprises a central portion having an upper surface for engagement with a portion of a femur and an opposing lower surface for engagement with a portion of a tibia. The central portion comprises a resilient polycarbonate polyurethane. The meniscus prosthetic device also includes an outer portion surrounding the central portion and having an increased thickness relative to the central portion. The outer portion comprises a resilient polycarbonate polyurethane embedded with tensioned ultra high molecular weight polyethylene reinforcing fibers. The outer portion has a first section with a semi-ellipsoidal profile similar to a natural meniscus and a second section connecting the ends of the first section. The second section is sized and shaped to engage the femur notch to secure the meniscus prosthetic device within the knee joint without penetrating bone.

In another embodiment, a meniscus implant is disclosed. The meniscus implant comprises a central portion having an upper surface for engagement with a portion of a femur and an opposing lower surface for engagement with a portion of a tibia. The central portion comprises a resilient polycarbonate polyurethane and is resiliently deformable between an unloaded position and a loaded position. The upper and lower surfaces of the central portion have increased contact with the femur and the tibia in the loaded position. The meniscus implant also includes an outer portion surrounding the central portion and having an increased thickness relative to the central portion. The outer portion comprising a resilient polycarbonate polyurethane embedded with tensioned ultra high molecular weight polyethylene reinforcing fibers. The outer portion includes a first section having a generally semi-ellipsoidal profile similar to a natural meniscus and a second section connecting the ends of the first section. The second section is sized and shaped to engage a femur notch to secure the meniscus prosthetic device within the knee joint without penetrating bone. The outer portion is resiliently deformable between an unloaded position and a loaded position. At least a section of the outer portion is displaced radially outward from the central portion in the loaded position.

In another embodiment, a prosthetic device for replacing a damaged meniscus of a knee joint is disclosed. The prosthetic device comprises a central portion having an upper surface for engagement with a portion of a femur and an opposing lower surface for engagement with a portion of a tibia. The central portion is formed of a resilient polyurethane. The prosthetic device also includes an outer portion surrounding the central portion and having an increased thickness relative to the central portion. The outer portion comprises a first section having a generally semi-ellipsoidal profile similar to that of a natural meniscus and a second section extending between first and second ends of the first section. The second section is sized and shaped to engage a femur notch to secure the meniscus prosthetic device within the knee joint without penetrating bone. The outer portion is formed of the resilient polyurethane embedded with reinforcing fibers such that the outer portion has an increased stiffness relative to the central portion.

In another embodiment, a meniscus prosthetic device is disclosed. The meniscus prosthetic devices comprises a central portion having an upper surface for engagement with a portion of a femur and an opposing lower surface for engagement with a portion of a tibia. An outer portion surrounds the central portion and has an increased thickness relative to the central portion. The outer portion comprises a first section having a generally semi-ellipsoidal profile similar to that of a natural meniscus and a second section extending between first and second ends of the first section. The second section is sized and shaped to engage a femur notch to secure the meniscus prosthetic device within a knee joint without penetrating bone. The second section has an upper-inner surface tapering into the upper surface of the central portion. The upper-inner surface is defined by a varying radius of curvature along a length of the second section.

In another embodiment, a meniscus implant for secured positioning within a knee joint without requiring the penetration of bone is disclosed. The meniscus implant comprises a central portion having an upper surface for engagement with a portion of a femur and an opposing lower surface for engagement with a portion of a tibia. An outer portion surrounds the central portion and has an increased thickness relative to the central portion. The outer portion comprises a first section having a generally semi-ellipsoidal profile similar to that of a natural meniscus and a second section extending between first and second ends of the first section. The second section has a first region adjacent the first end of the first section, a second region adjacent the second end of the first section, and third region between the first and second regions. The first region of the second section has a height between about 4 mm and about 15 mm, a first radius of curvature along the length of the second section between about 5 mm and about 70 mm, and a second radius of curvature perpendicular to the length of the second section between about 10 mm and about 100 mm. The second region of the second section has a height between about 4 mm and about 15 mm, a third radius of curvature along the length of the second section between about 5 mm and about 50 mm, and a fourth radius of curvature perpendicular to the length of the second section between about 5 mm and about 70 mm. The third region of the second section has a height between about 4 mm and about 15 mm and a first radius of curvature along the length of the second section between about 10 mm and about 30 mm.

In another embodiment, a method of manufacturing a meniscus prosthetic device is disclosed. The method comprises injection molding a core having an upper surface, a lower surface opposite the upper surface, and an outer surface disposed between the upper and lower surfaces. The outer surface defines a plurality of recesses. The method also includes winding reinforcing fiber into at least one of the plurality of recesses of the outer surface and injection molding an outer portion around the outer surface and the reinforcing fibers to secure the reinforcing fibers therein. In one aspect, the material of the core has a higher melting point than the reinforcing fibers.

In another embodiment, a method of manufacturing a prosthetic device is disclosed. The method comprises injecting a polycarbonate polyurethane into a mold to form a core. The mold comprises a mirror polished upper molding surface for defining an upper surface of the core, a mirror polished lower molding surface for defining a lower surface of the core, and one or more removable inserts for defining a plurality of recesses of the core. The method includes removing the one or more removable inserts and winding ultra high molecular weight polyethylene reinforcing fiber around the core and into at least one of the plurality of recesses of the core. The method also includes heating the core, injecting a polycarbonate polyurethane into the mold to form an outer layer surrounding the core and the reinforcing fiber, and cooling the mold. In some instances, the polycarbonate polyurethane has a higher melting point than the polyethylene reinforcing fibers such that the polycarbonate polyurethane is injected at a temperature above the melting point of the polyethylene reinforcing fibers.

In another embodiment, a method of forming a meniscus implant is disclosed. The method comprises injecting a polymer into a mold to form a core. The mold comprises a mirror polished upper molding surface for defining an upper surface of the core, a mirror polished lower molding surface for defining a lower surface of the core, and one or more removable inserts for defining a plurality of recesses around a perimeter of the core. The method also includes removing the one or more removable inserts and winding reinforcing fiber around the core and into the plurality of recesses of the core. The reinforcing fiber is tensioned with a force between about 5 N and about 78 N during the winding. The method also includes injecting a polymer into the mold to form an outer layer surrounding the core and the reinforcing fiber.

In another embodiment, a method of selecting a meniscus prosthetic device for a patient from a library of available prosthetic devices is disclosed. The method comprises a pre-implantation matching process. The pre-implantation matching process comprises a direct geometrical matching process, a correlation parameters-based matching process, and a finite element-based matching process. The direct geometrical matching process comprises obtaining an image of the patient's healthy knee, segmenting the knee into components, including a healthy meniscus, and comparing the healthy meniscus to the available prosthetic devices to identify any geometrically suitable prosthetic devices. The correlation parameters-based matching process comprises obtaining an image of the patient's injured knee, determining one or more correlation parameters for the available prosthetic devices based on anatomical measurements of the injured knee, and comparing the one or more correlation parameters for the available prosthetic devices to an accepted normative data range to identify any correlation-parameter suitable prosthetic devices. Finally, the finite element-based matching process comprises creating a finite element model of the patient's injured knee based on the image of the patient's injured knee, simulating a loading of the patient's injured knee with an available prosthetic device positioned therein for one or more of the available prosthetic devices, and evaluating a load distribution for the one or more of the available prosthetic devices to identify any finite-element suitable prosthetic devices.

In another embodiment, a method of treating a damaged meniscus is disclosed. The method comprises utilizing a pre-implantation matching process to identify a best suitable meniscus prosthetic device for replacing the damaged meniscus. The pre-implantation matching process comprises a correlation parameters-based matching process that considers an area correlation, a width correlation, a length correlation, and a perimeter correlation. The area correlation is defined by a meniscus contact area divided by a medial tibia area. The width correlation is defined by an average meniscus width divided by a medial tibia width. The length correlation is defined by a medial meniscus length divided by a medial tibia length. The perimeter correlation is defined by a meniscus perimeter divided by a medial tibia perimeter.

In another embodiment, a surgical method is disclosed. The surgical method comprises performing an arthroscopy to create a medial portal, excising a majority of a damaged meniscus, excising a portion of a fat pad, enlarging the medial portal to a diameter between about 4.0 cm and about 6.0 cm, accessing a medial cavity, trialing one or more implant trials to identify a most suitable meniscus prosthesis, and implanting and securing the most suitable meniscus prosthesis into the medial cavity without penetrating bone with the implant.

In another embodiment, a biocompatible composite material is molded from at least two materials having different melting points. In one aspect, the first material is heated above the melting point of the second material and molded around the second material.

BRIEF DESCRIPTION OF DRAWINGS

Other features and advantages of the present disclosure will become apparent in the following detailed description of embodiments of the disclosure with reference to the accompanying of drawings, of which:

FIG. 5 is a cross-sectional view of the prosthetic device of FIGS. 1 and 2 taken along section line 4-4 shown in comparison to a diagrammatic cross-sectional view of an alternative prosthetic device taken along a corresponding cross-section line.

FIG. 8 is a cross-sectional view of the prosthetic device of FIGS. 1 and 2 taken along section line 8-8 shown in comparison to a diagrammatic cross-sectional view of an alternative prosthetic device taken along a corresponding cross-section line.

FIG. 15 is a chart setting forth various correlation parameters according to one aspect of the present disclosure.

FIG. 22 is a diagrammatic perspective view of a prosthetic device for use in replacing a damaged natural meniscus according to the present disclosure shown in comparison to the dimensions of a healthy natural meniscus.

FIG. 23 is a block diagram of an embodiment of a method according to one aspect of the present disclosure for selecting an appropriate prosthetic device for use with a patient's knee during surgery.

FIG. 24 is a block diagram of a surgical protocol according to one aspect of the present disclosure.

FIG. 31 is a diagrammatic perspective view of an outer portion of the prosthetic device of FIG. 27 according to one aspect of the present disclosure.

FIG. 32 is a chart setting forth fiber incorporation ratios for prosthetic devices based on patient weight and activity levels according to one aspect of the present disclosure.

FIG. 33 is a diagrammatic cross-sectional view of a prosthetic device having a fiber density according to one aspect of the present disclosure.

FIG. 34 is a diagrammatic cross-sectional view of a prosthetic device similar to that of FIG. 38, but having an alternative fiber density according to one aspect of the present disclosure.

FIG. 35 is a block diagram of a method for manufacturing a prosthetic device according to one aspect of the present disclosure.

FIG. 36 is a chart setting forth tensioning forces for winding reinforcement fibers around a core of a prosthetic device according to one aspect of the present disclosure.

DETAILED DESCRIPTION

Figure 1:
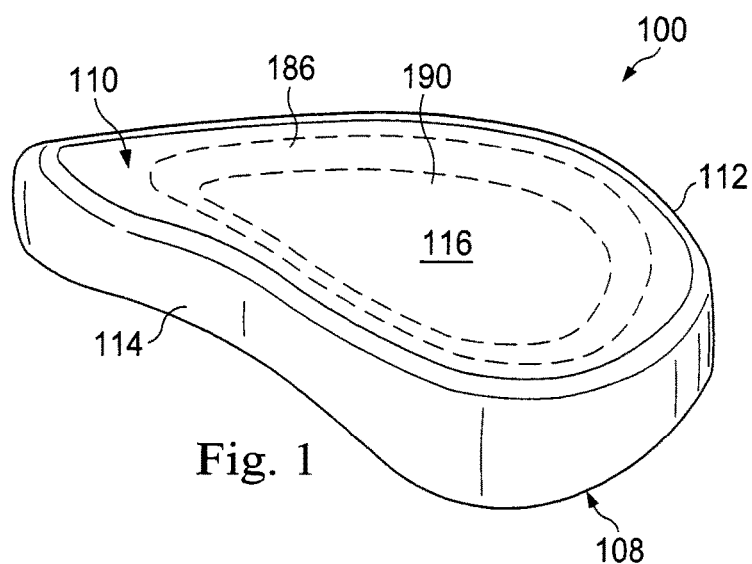
FIG. 1 is a diagrammatic perspective view of an embodiment of a prosthetic device according to one embodiment of the present disclosure.

For the purposes of promoting an understanding of the principles of the present disclosure, reference will now be made to the embodiments illustrated in the drawings, and specific language will be used to describe the illustrated embodiments. It is nevertheless understood that no limitation of the scope of the disclosure is intended. Any and all alterations or modifications to the described devices, instruments, and/or methods, as well as any further application of the principles of the present disclosure that would be apparent to one skilled in the art are encompassed by the present disclosure even if not explicitly discussed herein. Further, it is fully contemplated that the features, components, and/or steps described with respect to one embodiment may be combined with the features, components, and/or steps described with respect to other embodiments of the present disclosure.

Prosthetic Devices

Figure 3:
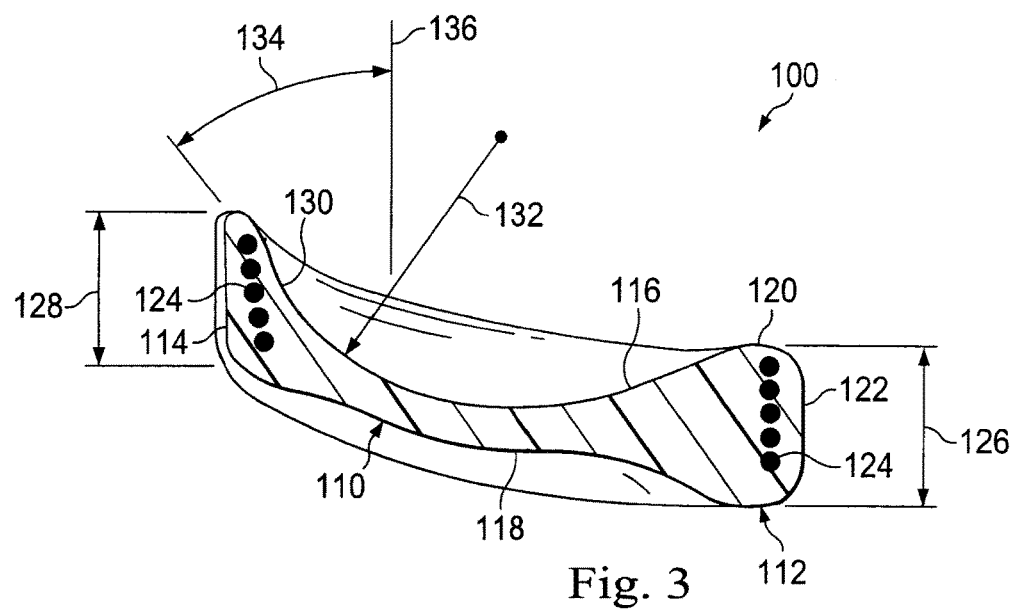
FIG. 3 is a diagrammatic cross-sectional view of the prosthetic device of FIGS. 1 and 2 taken along section line 3-3.
Figure 2:
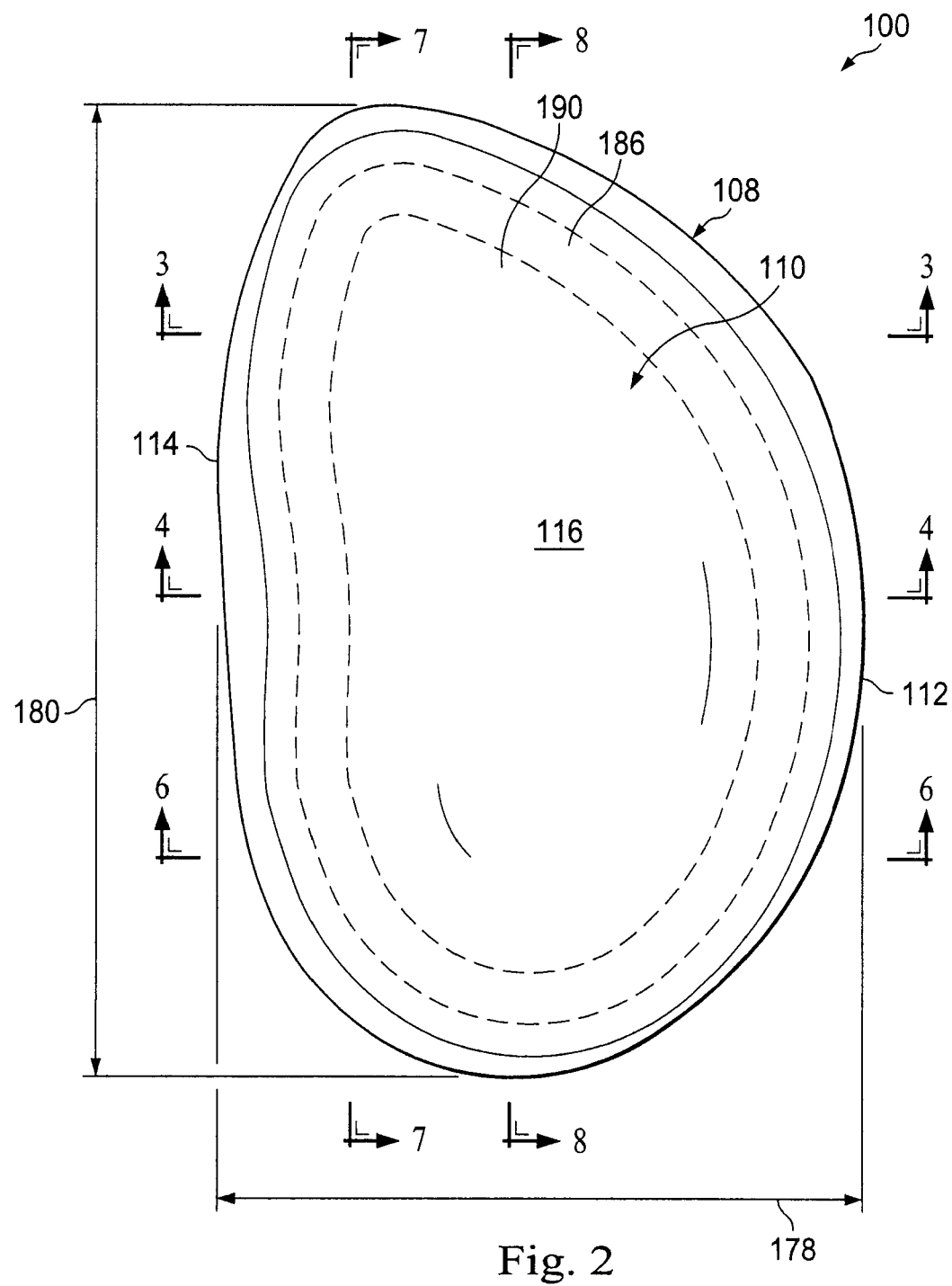
FIG. 2 is a diagrammatic top view of the prosthetic device of FIG. 1.
Figure 4:
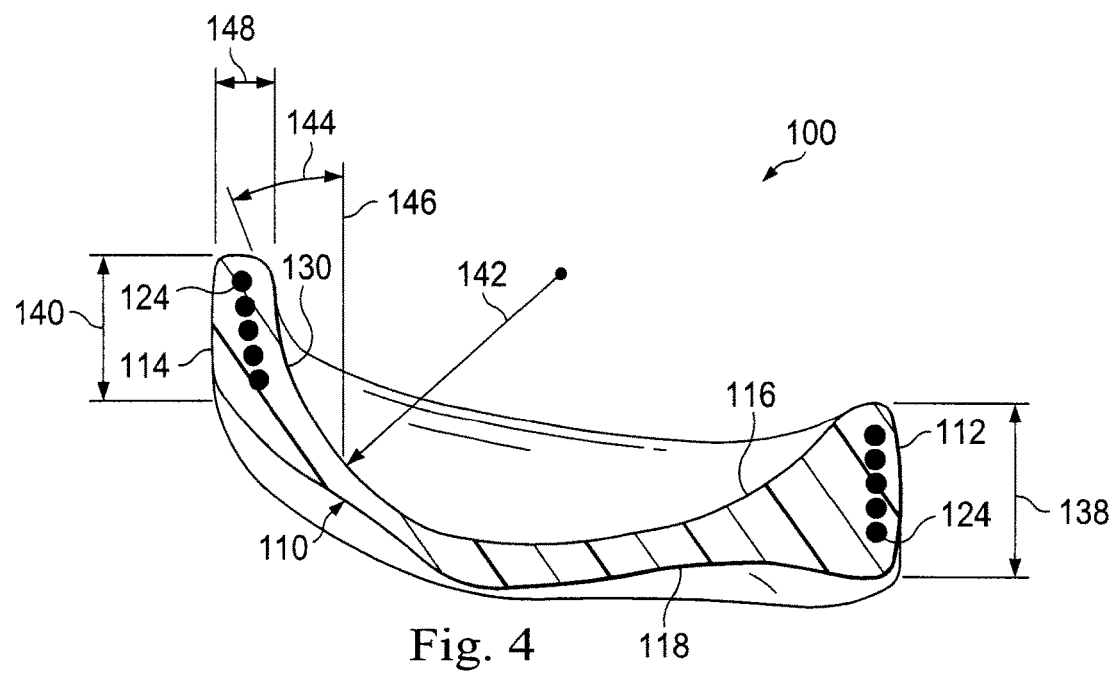
FIG. 4 is a diagrammatic cross-sectional view of the prosthetic device of FIGS. 1 and 2 taken along section line 4-4.
Figure 5:
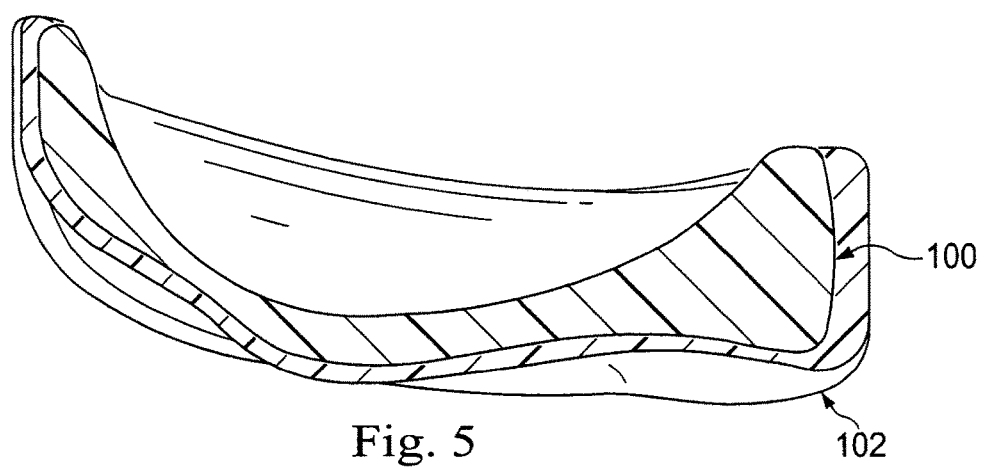
FIG. 5 is a diagrammatic cross-sectional comparison view of the prosthetic device of FIGS. 1 and 2 and an alternative prosthetic device. More specifically.
Figure 6:
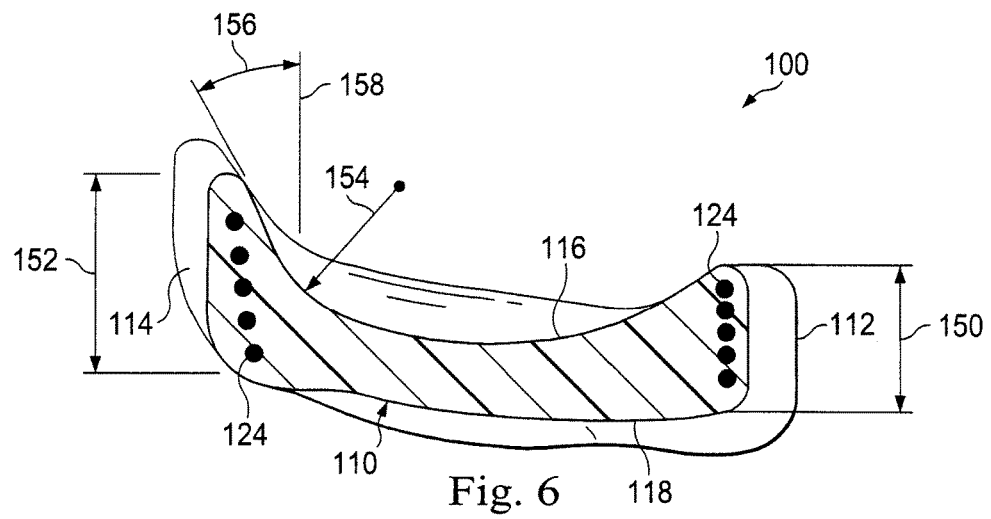
FIG. 6 is a diagrammatic cross-sectional view of the prosthetic device of FIGS. 1 and 2 taken along section line 6-6.
Figure 7:
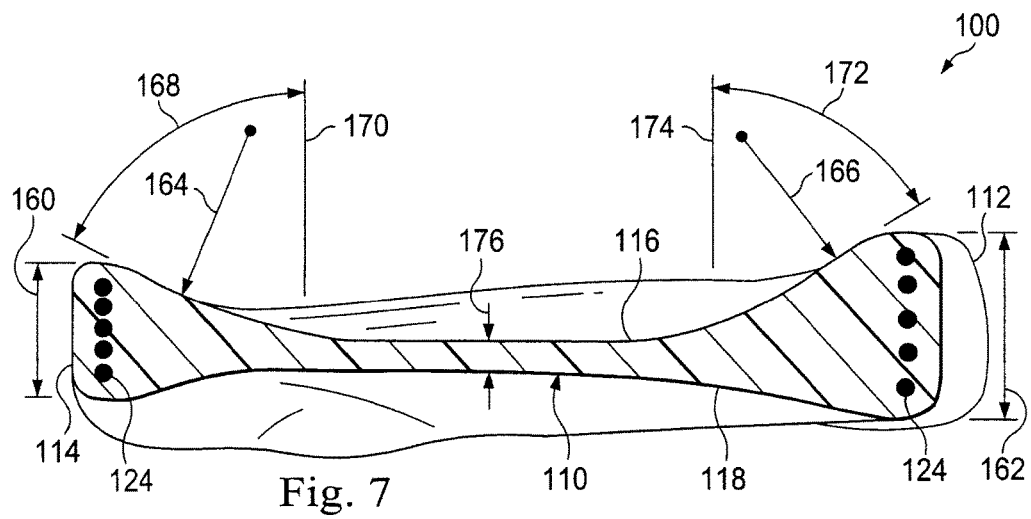
FIG. 7 is a diagrammatic cross-sectional view of the prosthetic device of FIGS. 1 and 2 taken along section line 7-7.
Figure 8:
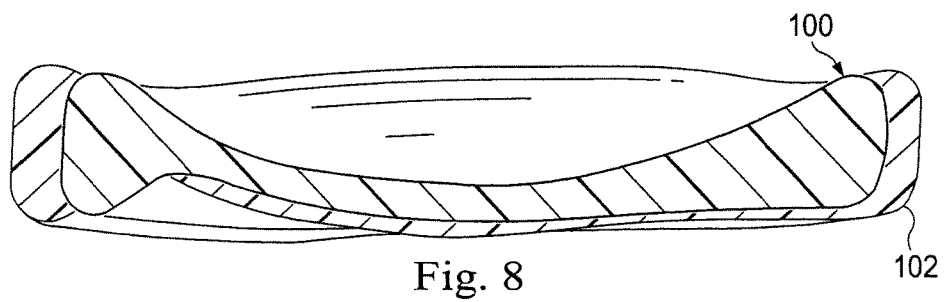
FIG. 8 is a diagrammatic cross-sectional comparison view of the prosthetic device of FIGS. 1 and 2 and an alternative prosthetic device. More specifically.
Figure 9A:
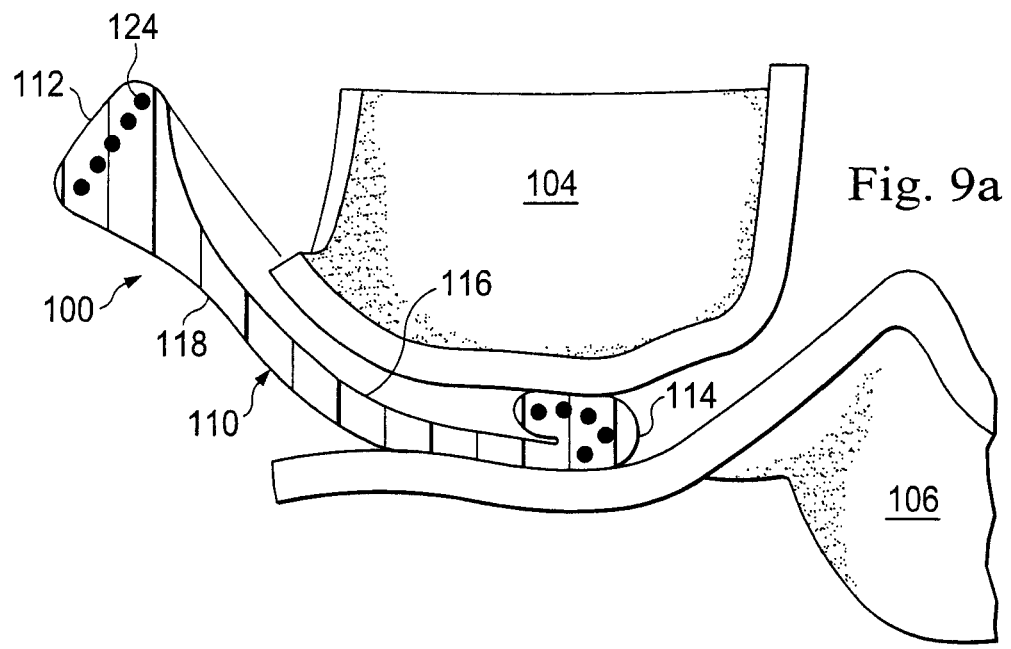
FIG. 9a is a diagrammatic cross-sectional view of the prosthetic device of FIGS. 1 and 2 positioned between a femur and a tibia in an insertion configuration.
Figure 9B:
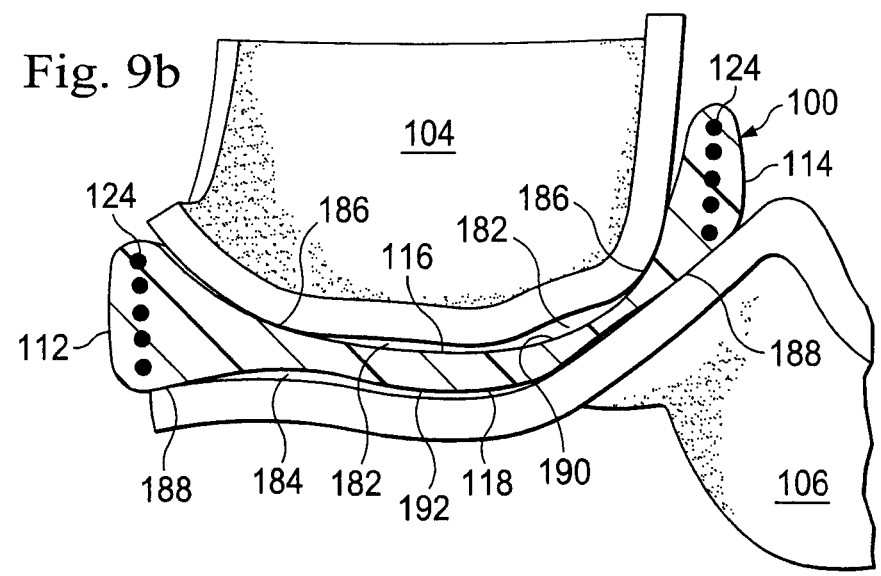
FIG. 9b is a diagrammatic cross-sectional view of the prosthetic device of FIGS. 1 and 2 positioned between a femur and a tibia in a pre-tensioned, unloaded state.
Figure 10:
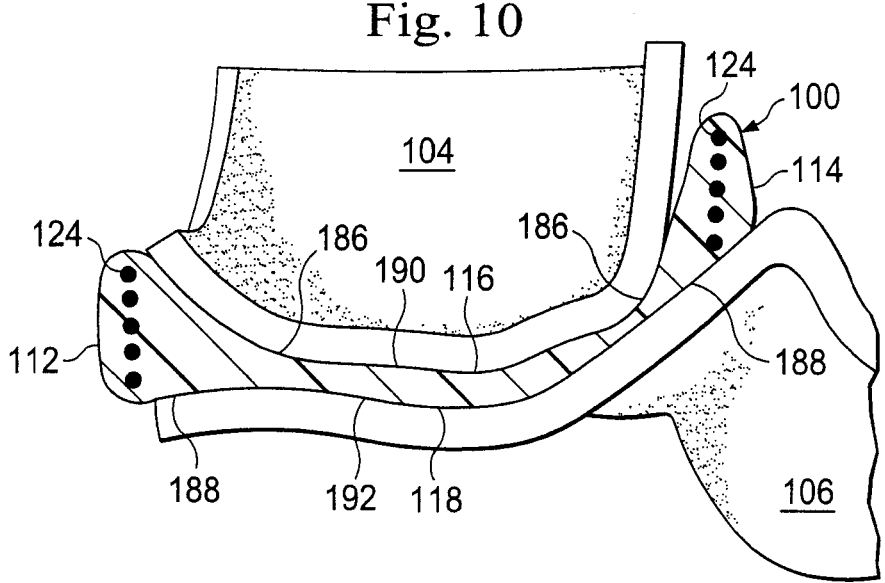
FIG. 10 is a diagrammatic cross-sectional view of the prosthetic device of FIGS. 1 and 2 positioned between a femur and a tibia similar to that of FIG. 9b, but showing the prosthetic device in a loaded, weight-bearing state.

Referring now to FIGS. 1, 2, 3, 4, 5, 6, 7, 8, 9, and 10 shown therein is a prosthetic device 100 according to one aspect of the present disclosure. In particular, FIG. 1 is a diagrammatic perspective view of the prosthetic device 100. FIG. 2 is a diagrammatic top view of the prosthetic device 100. FIGS. 3, 4, 5, 6, 7, and 8 show various cross-sectional views of the prosthetic device 100. FIG. 3 is a diagrammatic cross-sectional view of the prosthetic device 100 taken along section line 3-3 of FIG. 2. FIG. 4 is a diagrammatic cross-sectional view of the prosthetic device 100 taken along section line 4-4 of FIG. 2. FIG. 5 is a diagrammatic cross-sectional comparison view of the prosthetic device 100 with an alternative prosthetic device 102. More specifically, FIG. 5 is a cross-sectional view of the prosthetic device 100 taken along section line 4-4 of FIG. 2 shown in comparison to a cross-sectional view of the alternative prosthetic device 102 taken along a corresponding cross-section line. FIG. 6 is a diagrammatic cross-sectional view of the prosthetic device 100 taken along section line 6-6 of FIG. 2. FIG. 7 is a diagrammatic cross-sectional view of the prosthetic device 100 taken along section line 7-7 of FIG. 2. FIG. 8 is a diagrammatic cross-sectional comparison view of the prosthetic device 100 with the alternative prosthetic device 102 similar to that of FIG. 5, but taken along a different section line. More specifically, FIG. 8 is a cross-sectional view of the prosthetic device 100 taken along section line 8-8 of FIG. 2 shown in comparison to a cross-sectional view of the alternative prosthetic device 102 taken along a corresponding cross-section line. FIG. 9a is a diagrammatic cross-sectional view of the prosthetic device of FIGS. 1 and 2 positioned between a femur and a tibia in an insertion configuration. FIG. 9b is a diagrammatic cross-sectional view of the prosthetic device 100 positioned between a femur 104 and a tibia 106 in a pre-tensioned, unloaded state. FIG. 10 is a diagrammatic cross-sectional view of the prosthetic device 100 positioned between the femur 104 and the tibia 106 similar to that of FIG. 9b, but showing the prosthetic device 100 in a loaded, weight-bearing state.

Generally, the prosthetic device 100 is for the replacement of a meniscus that has been damaged, ruptured, disintegrated, diseased, or is otherwise in need of replacement. For illustrative purposes, the prosthetic device 100 will be described in conjunction with a right knee, medial meniscus replacement. However, corresponding embodiments are utilized for replacement of any of the other menisci, such as the left knee medial meniscus, left knee lateral meniscus, and/or right knee lateral meniscus. In that regard, the size, shape, thickness, material properties, and/or other properties of the prosthetic device may be configured for each particular application.

The prosthetic meniscus 100 comprises an outer body portion 108 and a central body portion 110. Generally, the outer body portion 108 has an increased thickness and height relative to the central body portion 110. In some instances the outer body portion 108 has a thickness between 5 mm and 15 mm. In some instances, the central body portion 110 has a thickness between 0.1 mm and 5 mm. In one particular embodiment, the outer body portion 108 has a maximum thickness of approximately 10 mm and the central body portion 110 has a maximum thickness of approximately 2 mm. The height or thickness of the outer body portion 108 varies around the perimeter of the prosthetic device 100 in some instances. In that regard, the variations in the height or thickness of the outer body portion 108 are selected to match the anatomical features of the patient in some embodiments. Similarly, the height or thickness of the central body portion 110 varies across the prosthetic device 100 in some embodiments. Again, the variations in the height or thickness of the central body portion 110 are selected to match the anatomical features of the patient in some embodiments. In some embodiments, the prosthetic device 100 is inserted in an insertion configuration and then loaded, stretched, moved, and/or otherwise transferred to an implantation configuration. In some embodiments the transformation between the insertion configuration and the implantation configuration is facilitated through the load bearing of the prosthetic device 100. In such embodiments, the variations in height or thickness of the outer and central body portions 108, 110 are selected to accommodate the deformation or transformation between the insertion configuration and the implantation configuration.

In the present embodiment, the prosthetic device 100 is configured for use without a fixation member or fixation device that would penetrate an adjacent bone to keep the prosthetic device in place. Rather, the prosthetic device 100 is configured to "float" within the knee joint without being secured by such bone-penetrating fixation devices or otherwise rigidly fixed to the femur or tibia. To that end, the outer body portion 108 of the prosthetic device 100 is shaped and sized to prevent unwanted expulsion of the prosthetic device 100 from the knee joint. The prosthetic device 100 is implanted into a patient without causing permanent damage to the patient's tibia or other bone structure(s) engaged by the prosthetic device in some embodiments. In some instances the prosthetic device 100 is implanted to alleviate the patient's knee problems while avoiding permanent destruction of the patient's anatomy, such as cutting or reaming a large opening in the tibia. In such instances, the prosthetic device 100 may be subsequently removed and replaced with another prosthetic device or treatment without adversely affecting the subsequent treatment.

To this end, the outer body portion 108 of the prosthetic device 100 includes a first portion 112 and a second portion or bridge 114. In some embodiments, the first portion 112 substantially matches the shape of a natural meniscus. In some embodiments, the outer body portion 108 has a semi-ellipsoidal shape. Accordingly, the first portion 112 extends around a majority of the outer body portion 108. The bridge 114 connects the two ends of the first portion 112. Thus, where the prosthetic device is configured for use as a medial meniscus device, the bridge 114 extends along the lateral side of the device. Where the prosthetic device 100 is configured for use as a lateral meniscus device, the bridge 114 extends along the medial side of the device. Accordingly, the outer body portion 108—comprised of the first portion 112 and the bridge 114 and having an increased thickness relative to the central body portion 110—completely surrounds the central body portion 110 and serves to limit movement of the prosthetic device 100 after implantation. That is, the increased height of the outer body portion 108 along with the contact pressure on the prosthetic device 100 from being positioned between the femur and the tibia prevents the prosthetic device from moving outside of the desired range of positions within the knee joint. In some instances, a distal portion of the femur is received within the upper recess defined by the outer body portion 108 and maintained within the recess by the increased height of the outer body portion 108 and the contact pressure on the device 100.

The height or thickness of the bridge component 114 is based on the size of the femur notch and the distance to the cruciate ligaments in some embodiments. In some embodiments, the bridge 114 has a maximum height or thickness that is between ¼ and ¾ the maximum height or thickness of the first portion 112 of the outer body portion 108. In some embodiments, the size and shape of the bridge 114 is selected to achieve an optimal pressure distribution on the tibialis plateau in order to mimic the pressure distribution of a healthy natural meniscus. The bridge 114 and, more generally, the outer body portion 108 are geometrically characterized by anterior, posterior, lateral-anterior, mid-lateral and lateral-posterior angles and heights as well as sagittal and coronal radii of curvature. Specific typical ranges of sizes, shapes, angles, radii of curvature, and other geometrical attributes of the bridge 114 will be discussed below with respect to FIGS. 3, 4, 6, and 7. While these ranges are understood to encompass the majority of ranges utilized in treating patients, no limitation is intended thereby. It is certainly contemplated that there are situations and/or applications where use of components outside of these ranges will be desirable or necessary.

Further, the outer body portion 108 and the central body portion 110 are shaped and sized such that the prosthetic device 100 is self-centering. That is, the shape and size of the prosthetic device 100 itself encourages the prosthetic device 100 to position or align itself with a desired orientation within the knee joint. Accordingly, as the prosthetic device 100 moves through a range of positions within the knee joint it naturally returns to the desired orientation due to the shape and size of the outer and central body portion 108, 110. In some embodiments, the outer body portion and, more specifically, the bridge 114 acts as a physical barrier limiting the movement of the prosthetic device caused by joint reaction forces. The self-centering or self-aligning mechanism combined with the prosthetic device's ability to move within the knee joint results in improved location of the prosthetic device 100 during typical load-bearing gait cycles (e.g., flexion-extension angles of 0° to 20° or "heel-strike" to "toe-off"). The result is that the prosthetic device 100 exhibits a load pressure distribution similar to that of a natural meniscus.

The central body portion 110 defines an upper surface 116 and a lower surface 118. The upper and lower surfaces 116, 118 are both articulating bearing surfaces. In particular, the upper and lower surfaces 116, 118 are configured to movingly engage with the femur and tibia, respectively. In that regard, the prosthetic device 100 can translate and rotate with respect to the femur and/or tibia within a range. In some instances, translation is possible in both the anterior-posterior and medial-lateral directions. In some embodiments, the upper surface 116 includes both a vertical and horizontal bearing components. To that end, in some embodiments the upper surface 116 comprises a concave surface that defines the vertical and horizontal bearing components. The thickness of the central body portion 110 between the upper surface 116 and the lower surface 118 supports the vertical bearing component, while the increased height of the upper surface 116 as it extends outwardly towards the outer body portion 108 defines the horizontal bearing component. Similarly, in some embodiments the lower surface 118 includes both vertical and horizontal bearing components. In particular, in some embodiments the lower surface 118 comprises a convex surface. The thickness of the central body portion 110 between the upper surface 116 and the lower surface 118 supports the vertical bearing component, while the tapered height of the lower surface 116 as it extends outwardly towards the outer body portion 108 defines the horizontal bearing component. In some embodiments, the upper surface 116 and/or the lower surface 118 are shaped such that the prosthetic device 10 is biased towards a neutral position in the knee. For example, the arcuate profiles of the upper surface 116 and/or the lower surface 116 are shaped such that the interaction between the surfaces and the bone encourages the bone to a particular orientation relative to the surfaces. This allows the prosthetic device 100 to be self-centering or self-aligning in some embodiments as discussed above with respect to the outer body portion 108.

In some embodiments, the prosthetic device 100 includes one or more recesses (not shown) in the upper surface 116. The recesses provide for the accumulation of synovial fluid. In some embodiments, the recesses are positioned at the most prevalent contact points of the femur with the upper surface 116. In such embodiments, the synovial fluid lubricates the upper articulation surface 116 of the prosthetic device to limit the friction between the prosthetic device 100 and the femur. The recesses may have various shapes within the upper surface 116 and, in some instances, are shaped based on the specific anatomical features of a patient. In that regard, the recesses may comprise a sloping depression that creates a concave recess in some embodiments. The concave recess may comprise a substantially circular profile, an elongated profile, an irregular shape, and/or combinations thereof. The prosthetic device 100 includes a various number of recesses in different embodiments. In some embodiments, the prosthetic device 100 does not include any recesses in the upper surface 116 as illustrated in FIG. 1.

As shown in FIGS. 1 and 2, the upper articulation surface 116 is bounded by the outer body portion 108. In that regard, the first portion 112 and the bridge 114 of the outer body portion 108 define a rim or wall having an increased height relative to the central body portion 110 such that the upper surface 116 is recessed with respect to the outer body portion 108. Referring more specifically to FIGS. 3, 4, 6, and 7, in the current embodiment, the outer body portion 108 defines a substantially convex upper surface 120 that tapers down in to the upper articulation surface 116 on one side and to an outer surface 122 of the prosthetic device 100 on the other side. Accordingly, the upper surface 116 of the central body portion 110 and the taper of the upper surface 120 of the outer body portion 108 define a concave recess configured for receiving a portion of the femur such as the femoral condyle. Accordingly, in some instances when the prosthetic device 100 is implanted, the central body portion 110 bounded by the outer body portion 108 serves to isolate and cushion the femoral condyle from the tibial plateau. In that regard, the outer body portion 108 serves to limit the movement of the prosthetic device relative to the femoral condyle. In particular, in the current embodiment the outer body portion 108 prevents the portion of the femur movingly engaged with the prosthetic device 100 from moving laterally beyond the outer body portion 108. In this manner the prosthetic device 100 provides shock absorption and a desirable tribology between the femur and tibia.

Referring more specifically to FIGS. 2-8, typical ranges of sizes, shapes, angles, radii of curvature, and other geometrical attributes of the prosthetic device 100 will be discussed. While these ranges are understood to encompass the majority of ranges utilized in treating patients, no limitation is intended thereby. It is certainly contemplated that there are situations and/or applications where use of components outside of these ranges will be desirable or necessary.

Referring more specifically to FIG. 3, shown therein is a diagrammatic cross-sectional view of the prosthetic device 100 taken along section line 3-3 of FIG. 2. As shown, in the current embodiment the outer body portion 108 includes a plurality of imbedded fibers 124 therein. The imbedded fibers 124 are utilized in some embodiments to pretension the prosthetic device 100. In some embodiments the imbedded fibers 124 are utilized to increase the stiffness and/or strength of the outer body portion 108 relative to the central body portion 110. In some embodiments, the fibers 124 are utilized to both pretension the prosthetic device 100 and to increase the radial stiffness and/or hoop strength of the outer body portion 108. In some instances, the imbedded fibers 124 comprise an ultra high molecular weight polyethylene. In one particular embodiment, the fibers 124 comprise an ultra high molecular weight polyethylene and are imbedded within a polycarbonate polyurethane forming at least the outer body portion 108 of the prosthetic device 100.

In some instances, the fibers 124 prevent the bridge 114 from splaying outwardly, which prevents the prosthetic device 100 from being released from the knee. The fibers 124 tend to transfer the radial outward forces applied on the bridge 114 to a portion of the outer body portion 108 on the opposite side of the prosthetic device 100, which is in contact with the femur. In this manner, the fibers 124 prevent unwanted movement of the prosthetic device 100 and, in particular, prevent the prosthetic device from slipping or popping out of the knee joint. During insertion, however, the bridge 114 may be folded inwardly into an insertion configuration (see FIG. 9a for example) as the fibers do not resist inwardly directed radial or compressive forces. Once the bridge 114 is inserted past the bearing condyle surfaces and adjacent to the femoral notch, the resilient properties of the prosthetic device's core material causes the bridge to spring outwardly into an anchoring configuration (see FIG. 9b for example).

As shown in FIG. 3, the first portion 112 of the outer body portion 108 has a height or thickness 126 at cross-sectional line 3-3. In that regard, the height or thickness 126 of the first portion 112 is between about 4 mm and about 15 mm and, in some instances, between about 5.7 mm and about 9.3 mm. In the present embodiment, the height or thickness 126 of the first portion 112 is approximately 7.6 mm. In a smaller embodiment, the height or thickness 126 is approximately 5.7 mm. In a larger embodiment, the height or thickness 126 is approximately 9.3 mm. In the present embodiment, configured for use as a medial meniscus replacement, the height or thickness 126 may be considered a medial-anterior height or thickness of the first portion 112 of the outer body portion 108. In a lateral meniscus replacement, the corresponding height or thickness of a similar prosthetic device configured for the lateral replacement may be within a similar range and be considered a lateral anterior height or thickness of the outer body portion.

Similarly, the bridge 114 of the outer body portion 108 has a height or thickness 128 at cross-sectional line 3-3. The height or thickness 128 of the bridge 114 is also between about 4 mm and about 15 mm and, in some instances, between about 5.1 mm and about 8.8 mm. In the present embodiment, the height or thickness 128 of the bridge 114 is approximately 7.0 mm. In a smaller embodiment, the height or thickness 128 is approximately 5.1 mm. In a larger embodiment, the height or thickness 128 is approximately 8.8 mm. In the present embodiment, configured for use as a medial meniscus replacement, the height or thickness 128 may be considered a lateral-anterior height or thickness of the bridge 114. In a lateral meniscus replacement, the corresponding height or thickness of a similar prosthetic device configured for the lateral replacement may be within a similar range and be considered a medial anterior height or thickness of the bridge.

An inner surface 130 of the bridge 114 connects the bridge 114 to the upper articulating surface 116 of the central body portion 110. The inner surface 130 has a radius of curvature 132 at cross-sectional line 3-3. In that regard, the radius of curvature 132 is between about 5 mm and about 70 mm and, in some instances, between about 9.3 mm and about 15.3 mm. In the present embodiment, the radius of curvature 132 is approximately 12 mm. In a smaller embodiment, the radius of curvature 132 is approximately 9.3 mm. In a larger embodiment, the radius of curvature is approximately 15.3 mm. In some instances, the radius of curvature 132 is smaller than the radius of curvature of the upper surface 116. In the present embodiment, configured for use as a medial meniscus replacement, the radius of curvature 132 may be considered a lateral-anterior radius of curvature of the prosthetic device 100. In a lateral meniscus replacement, the corresponding radius of curvature of a similar prosthetic device configured for the lateral replacement may be within a similar range and be considered a medial-anterior radius of curvature of the prosthetic device.

At cross-sectional line 3-3, the bridge 114 generally extends at an angle 134 with respect to an axis 136 extending substantially perpendicular to a plane generally defined by the prosthetic device 100, as shown. In some instances, the axis 136 extends from the intersection of the bridge 114 with the central body portion 110. The angle 134 is between about 20 degrees and about 70 degrees and, in some instances, is between about 30 degrees and about 32 degrees. In the present embodiment, the angle 134 is approximately 31 degrees. In a smaller embodiment, the angle 134 is approximately 30 degrees. In a larger embodiment, the angle 134 is approximately 32 degrees. In the present embodiment, configured for use as a medial meniscus replacement, the angle 134 may be considered a lateral-anterior angle of the prosthetic device 100. In a lateral meniscus replacement, the corresponding angle of a similar prosthetic device configured for the lateral replacement may be within a similar range and be considered a medial-anterior angle of the prosthetic device.

Referring more specifically to FIG. 4, shown therein is a diagrammatic cross-sectional view of the prosthetic device 100 taken along section line 4-4 of FIG. 2. As shown, the first portion 112 of the outer body portion 108 has a height or thickness 138 at cross-sectional line 4-4. In that regard, the height or thickness 138 of the first portion 112 is between about 4 mm and about 15 mm and, in some instances, is between about 5.8 mm and about 9.5 mm. In the present embodiment, the height or thickness 138 of the first portion 112 is approximately 7.7 mm. In a smaller embodiment, the height or thickness 138 is approximately 5.8 mm. In a larger embodiment, the height or thickness 138 is approximately 9.5 mm. In the present embodiment, configured for use as a medial meniscus replacement, the height or thickness 138 may be considered a mid-medial height or thickness of the first portion 112 of the outer body portion 108. In a lateral meniscus replacement, the corresponding height or thickness of a similar prosthetic device configured for the lateral replacement may be within a similar range and be considered a mid-lateral height or thickness of the outer body portion.

Similarly, the bridge 114 of the outer body portion 108 has a height or thickness 140 at cross-sectional line 4-4. The height or thickness 140 of the bridge 114 is also between about 4 mm and about 15 mm and, in some instances, is between about 4.6 mm and about 7.8 mm. In the present embodiment, the height or thickness 140 of the bridge 114 is approximately 6.0 mm. In a smaller embodiment, the height or thickness 140 is approximately 4.6 mm. In a larger embodiment, the height or thickness 140 is approximately 7.8 mm. In the present embodiment, configured for use as a medial meniscus replacement, the height or thickness 140 may be considered a mid-lateral height or thickness of the bridge 114. In a lateral meniscus replacement, the corresponding height or thickness of a similar prosthetic device configured for the lateral replacement may be within a similar range and be considered a mid-medial height or thickness of the bridge.

The inner surface 130 connecting the bridge 114 to the articulating surface 116 has a radius of curvature 142 at cross-sectional line 4-4. In that regard, the radius of curvature 142 is between about 8 mm and about 30 mm and, in some instances, between about 8.9 mm and about 15.2 mm. In the present embodiment, the radius of curvature 142 is approximately 14 mm. In a smaller embodiment, the radius of curvature 142 is approximately 8.9 mm. In a larger embodiment, the radius of curvature is approximately 15.2 mm. In some instances, the radius of curvature 142 is smaller than the radius of curvature of the upper surface 116. In the present embodiment, configured for use as a medial meniscus replacement, the radius of curvature 142 may be considered a mid-lateral radius of curvature of the prosthetic device 100. In a lateral meniscus replacement, the corresponding radius of curvature of a similar prosthetic device configured for the lateral replacement may be within a similar range and be considered a mid-medial radius of curvature of the prosthetic device.

At cross-sectional line 4-4, the bridge 114 generally extends at an angle 144 with respect to an axis 146 extending substantially perpendicular to a plane generally defined by the prosthetic device 100, as shown. The angle 144 is between about 15 degrees and about 60 degrees and, in some instances, is between about 18 degrees and about 20 degrees. In the present embodiment, the angle 144 is approximately 19 degrees. In a smaller embodiment, the angle 144 is approximately 18 degrees. In a larger embodiment, the angle 144 is approximately 20 degrees. In the present embodiment, configured for use as a medial meniscus replacement, the angle 144 may be considered a mid-lateral angle of the prosthetic device 100. In a lateral meniscus replacement, the corresponding angle of a similar prosthetic device configured for the lateral replacement may be within a similar range and be considered a mid-medial angle of the prosthetic device.

The bridge 114 of the outer body portion 108 also has a width or thickness 148 at cross-sectional line 4-4. The width or thickness 148 of the bridge 114 is between about 1 mm and about 5 mm and, in some instances, is between about 2.0 mm and about 3.3 mm. In the present embodiment, the width or thickness 140 of the bridge 114 is approximately 2.0 mm. In a smaller embodiment, the width or thickness 140 is also approximately 2.0 mm. In a larger embodiment, the width or thickness 140 is approximately 3.3 mm. In the present embodiment, configured for use as a medial meniscus replacement, the width or thickness 148 may be considered a mid-lateral width or thickness of the bridge 100. In a lateral meniscus replacement, the corresponding width or thickness of a similar prosthetic device configured for the lateral replacement may be within a similar range and be considered a mid-medial width or thickness of the bridge. In some embodiments, the width or thickness of the bridge 114 is substantially constant along the length of the bridge from the anterior to the posterior of the prosthetic device 100. In other embodiments, the width or thickness of the bridge 114 varies along the length of the bridge from the anterior to the posterior of the prosthetic device 100.

Referring now to FIG. 5, shown therein is a diagrammatic cross-sectional view of the prosthetic device 100 shown in comparison with an alternative prosthetic device 102. More specifically, FIG. 5 is a cross-sectional view of the prosthetic device 100 taken along section line 4-4 of FIG. 2 shown in comparison to a cross-sectional view of the alternative prosthetic device 102 taken along a corresponding cross-section line. As illustrated, the prosthetic device 100 has a reduced profile relative to the larger profile of the prosthetic device 102. In that regard, the prosthetic device 102 is sized to substantially match the size of a natural meniscus of the patient, whereas the prosthetic device 100 has a reduced size relative to the natural meniscus it is to replace. In that regard, the prosthetic device 100 is pretensioned to a reduced size in some instances. In one particular embodiment, the imbedded fibers positioned within the outer body portion 108 are utilized to the pretension the device 100. In some embodiments, the prosthetic device 100 is configured to stretch or expand once positioned within the knee joint and subjected to load bearing. In some instances, the outer body portion 108 is configured to expand outwardly as loading forces are applied to the prosthetic device and the inner body portion 110 is configured to conform to the engagement surfaces of the femur and tibia as the loading forces are applied. To that end, the angles of the inner walls of the prosthetic device 100 that will mate with the femur are steep enough such that as loading is applied to the prosthetic device the outer body portion 108 will be urged outward and not simply compressed downward. Accordingly, in some instances the prosthetic device 100 selected for use in treating a patient is intentionally smaller in size than the natural meniscus it will be replacing.

Referring to FIG. 6, shown therein is a diagrammatic cross-sectional view of the prosthetic device 100 taken along section line 6-6 of FIG. 2. As shown, the first portion 112 of the outer body portion 108 has a height or thickness 150 at cross-sectional line 4-4. In that regard, the height or thickness 150 of the first portion 112 is between about 4 mm and about 15 mm and, in some instances, is between about 5.8 mm and about 9.1 mm. In the present embodiment, the height or thickness 150 of the first portion 112 is approximately 7.5 mm. In a smaller embodiment, the height or thickness 150 is approximately 5.8 mm. In a larger embodiment, the height or thickness 150 is approximately 9.1 mm. In the present embodiment, configured for use as a medial meniscus replacement, the height or thickness 150 may be considered a medial posterior height or thickness of the first portion 112 of the outer body portion 108. In a lateral meniscus replacement, the corresponding height or thickness of a similar prosthetic device configured for the lateral replacement may be within a similar range and be considered a lateral posterior height or thickness of the outer body portion.

Similarly, the bridge 114 of the outer body portion 108 has a height or thickness 152 at cross-sectional line 6-6. The height or thickness 152 of the bridge 114 is also between about 4 mm and about 15 mm and, in some instances, is between about 8 mm and about 12.1 mm. In the present embodiment, the height or thickness 152 of the bridge 114 is approximately 8.8 mm. In a smaller embodiment, the height or thickness 152 is approximately 8.0 mm. In a larger embodiment, the height or thickness 152 is approximately 12.1 mm. In the present embodiment, configured for use as a medial meniscus replacement, the height or thickness 152 may be considered a lateral posterior height or thickness of the bridge 114. In a lateral meniscus replacement, the corresponding height or thickness of a similar prosthetic device configured for the lateral replacement may be within a similar range and be considered a medial posterior height or thickness of the bridge.

The inner surface 130 connecting the bridge 114 to the articulating surface 116 has a radius of curvature 154 at cross-sectional line 6-6. In that regard, the radius of curvature 154 is between about 5 mm and about 50 mm and, in some instances, is between about 7.4 mm and about 11.6 mm. In the present embodiment, the radius of curvature 154 is approximately 11 mm. In a smaller embodiment, the radius of curvature 154 is approximately 7.4 mm. In a larger embodiment, the radius of curvature 154 is approximately 11.6 mm. In some instances, the radius of curvature 154 is smaller than the radius of curvature of the upper surface 116. In the present embodiment, configured for use as a medial meniscus replacement, the radius of curvature 154 may be considered a lateral posterior radius of curvature of the prosthetic device 100. In a lateral meniscus replacement, the corresponding radius of curvature of a similar prosthetic device configured for the lateral replacement may be within a similar range and be considered a medial posterior radius of curvature of the prosthetic device.

At cross-sectional line 6-6, the bridge 114 generally extends at an angle 156 with respect to an axis 158 extending substantially perpendicular to a plane generally defined by the prosthetic device 100, as shown. The angle 156 is between about 15 degrees and about 60 degrees and, in some instances, is between about 29 degrees and about 31 degrees. In the present embodiment, the angle 156 is approximately 30 degrees. In a smaller embodiment, the angle 156 is approximately 29 degrees. In a larger embodiment, the angle 156 is approximately 31 degrees. In the present embodiment, configured for use as a medial meniscus replacement, the angle 156 may be considered a lateral posterior angle of the prosthetic device 100. In a lateral meniscus replacement, the corresponding angle of a similar prosthetic device configured for the lateral replacement may be within a similar range and be considered a medial posterior angle of the prosthetic device.

Referring to FIG. 7, shown therein is a diagrammatic cross-sectional view of the prosthetic device 100 taken along section line 7-7 of FIG. 2. Section line 7-7 extends through the bridge 114 of the outer body portion 108 of the prosthetic device 100. As shown, the bridge 114 of the outer body portion 108 has an anterior height or thickness 160 at cross-sectional line 7-7. In that regard, the anterior height or thickness 160 of the bridge 114 is between about 4 mm and about 15 mm and, in some instances, is between about 5.7 mm and about 9.3 mm. In the present embodiment, the anterior height or thickness 160 of the bridge 114 is approximately 7.8 mm. IN a smaller embodiment, the anterior height or thickness 160 is approximately 5.7 mm. In a larger embodiment, the anterior height or thickness 160 is approximately 9.3 mm. The bridge 114 of the outer body portion 108 has a posterior height or thickness 162 at cross-sectional line 7-7. The posterior height or thickness 162 of the bridge 114 is between about 4 mm and about 20 mm and, in some instances, is between about 7.7 mm and about 12.7 mm. In the present embodiment, the posterior height or thickness 162 of the bridge 114 is approximately 9.0 mm. In a smaller embodiment, the posterior height or thickness 162 is approximately 7.7 mm. In a larger embodiment, the posterior height or thickness 162 is approximately 12.7 mm.

The anterior portion of the upper surface of the bridge 114 has an anterior radius of curvature 164 at cross-sectional line 7-7. In that regard, the anterior radius of curvature 164 is between about 10 mm and about 100 mm and, in some instances, is between about 23.0 mm and about 33.1 mm. In the present embodiment, the radius of curvature 164 is approximately 72 mm. In another embodiment, the radius of curvature 164 is approximately 28 mm. In a smaller embodiment, the radius of curvature 164 is approximately 23 mm. In a larger embodiment, the radius of curvature 164 is approximately 33.1 mm. The posterior portion of the upper surface of the bridge 114 has a posterior radius of curvature 166 at cross-sectional line 7-7. In that regard, the posterior radius of curvature 166 is between about 5 mm and about 70 mm and, in some instances, is between about 15.2 mm and about 24.2 mm. In the present embodiment, the radius of curvature 166 is approximately 18.5 mm. In a smaller embodiment, the radius of curvature 166 is approximately 15.2 mm. In a larger embodiment, the radius of curvature 166 is approximately 24.2 mm.

Further, the anterior portion of the upper surface of the bridge 114 generally extends at an anterior angle 168 with respect to an axis 170 extending substantially perpendicular to a plane generally defined by the prosthetic device 100, as shown. The anterior angle 168 is between about 45 degrees and about 75 degrees and, in some instances, is between about 62 degrees and about 68 degrees. In the present embodiment, the angle 168 is approximately 65 degrees. In a smaller embodiment, the angle 168 is approximately 62 degrees. In a larger embodiment, the angle is approximately 68 degrees. The posterior portion of the upper surface of the bridge 114 generally extends at an posterior angle 172 with respect to an axis 174 extending substantially perpendicular to a plane generally defined by the prosthetic device 100, as shown. The posterior angle 172 is between about 35 degrees and about 70 degrees and, in some instances, is between about 55 degrees and about 61 degrees. In the present embodiment, the angle 172 is approximately 58 degrees. In a smaller embodiment, the angle 172 is approximately 55 degrees. In a larger embodiment, the angle 172 is approximately 61 degrees.

The central body portion 110 has a height or thickness 176 between the upper articulation surface 116 and the lower articulation surface 118 at cross-sectional line 7-7. In some embodiments, the height or thickness 176 is the minimal thickness of the central body portion 110 and, in more specific embodiments, the minimal thickness of the entire prosthetic device 100. To that end, the height or thickness 176 is between about 1 mm and about 3 mm and, in some instances, is between about 1.2 mm and about 2.1 mm. In the present embodiment, the height or thickness 176 is approximately 1.5 mm. In a smaller embodiment, the height or thickness 176 is approximately 1.2 mm. In a larger embodiment, the height or thickness 176 is approximately 2.1 mm.

Referring again to FIG. 2, as shown therein the prosthetic device 100 has a maximum or total width 178 extending between the outer boundaries of the first portion 112 and the bridge 114 of the outer body portion 108. In that regard, the width 178 is between about 20 mm and about 65 mm and, in some instances, is between about 24.8 mm and about 40.6 mm. In the current embodiment, the width 178 is approximately 32 mm. In a smaller embodiment, the width 178 is approximately 24.8 mm. In a larger embodiment, the width 178 is approximately 40.6 mm. Also, the prosthetic device 100 has a maximum or total length 180 extending between the opposing outer boundaries of the first portion 112 of the outer body portion 108. In that regard, the length 180 is between about 20 mm and about 60 mm and, in some instances, is between about 34.5 mm and about 56.5 mm. In the current embodiment, the length 180 is approximately 46 mm. In a smaller embodiment, the length 180 is approximately 34.5 mm. In a larger embodiment, the length 180 is approximately 56.5 mm.

Referring now to FIG. 8, shown therein is a diagrammatic cross-sectional view of the prosthetic device 100 shown in comparison with an alternative prosthetic device 102. More specifically, FIG. 8 is a cross-sectional view of the prosthetic device 100 taken along section line 8-8 of FIG. 2 shown in comparison to a cross-sectional view of the alternative prosthetic device 102 taken along a corresponding cross-section line. Similar to FIG. 5 discussed above, the prosthetic device 100 has a reduced profile relative to the larger profile of the prosthetic device 102. In that regard, the prosthetic device 102 is again sized to substantially match the size of a natural meniscus of the patient, whereas the prosthetic device 100 has a reduced size relative to the natural meniscus it is to replace. The prosthetic device 100 is pretensioned to a reduced size in some instances. In some embodiments, the prosthetic device 100 is configured to stretch or expand once positioned within the knee joint and subjected to load bearing. In some instances, the outer body portion 108 is configured to expand outwardly as loading forces are applied to the prosthetic device and the inner body portion 110 is configured to conform to the engagement surfaces of the femur and tibia as the loading forces are applied. To that end, the angles of the inner walls of the prosthetic device 100 that mate with the femur are steep enough such that as loading is applied to the prosthetic device the outer body portion 108 will be urged outward and not simply compressed downward. Accordingly, in some instances the prosthetic device 100 selected for use in treating a patient is intentionally smaller in size than the natural meniscus it replaces.

In some instances the outer body portion 108 has an increased stiffness relative to the central body portion 110. As discussed in greater detail below, this increased stiffness may be the result of different material properties, geometries, support features, and/or other mechanisms for varying the stiffness between the central body portion 110 and the outer body portion 108. Further, in some embodiments, the outer body portion 108 is pre-tensioned to improve the mating fit of the prosthetic device 100 within the knee joint. In some instances pre-tensioning the prosthetic device 100 maximizes the contact area of the load-bearing surfaces of the prosthetic device 100 to distribute loading through the prosthetic device 100 in a manner substantially similar to that of a healthy natural meniscus. In some embodiments, a single feature of the outer body portion 108 is utilized to both pretension the prosthetic device 100 and also increase the stiffness and/or strength of outer body portion.

In some embodiments the outer body portion 108 of the prosthetic device 100 includes a deformation control element to limit the deformation of the outer body portion. In some embodiments, the deformation control element is also utilized to pretension the device as discussed above. The deformation control element may be a material property, a structural property, an additional component, and/or combinations thereof. It should be noted that the various deformation control elements described herein may be combined to further limit or define the amount of deformation of the outer body portion 108 and/or tailor the amount of pretensioning of the prosthetic device. In some embodiments, the outer body portion 108 is includes materials or fibers for increasing the stiffness and/or strength of the outer body portion relative to the central body portion 110. In one specific embodiment, the central body portion 110 of the prosthetic device 100 is formed of Bionate 80A with the outer body portion 108 reinforced with DSM Dyneema UHMWPE fibers. Bionate 80A is a resilient polymeric material having a modulus of elasticity similar to that of articular cartilage and, in some instances, between about 1-10 MPa and, in some instances, between about 4-8 MPa. As another example, in one embodiment the outer body portion 108 includes carbon fibers providing additional strength and limiting the flexibility of the outer body portion. In some embodiments the carbon fibers are injected prior to the curing of the outer body portion 108. In other embodiments, the outer body portion 108 is formed or molded around the carbon fibers. In other embodiments, other additives or fibers are utilized to reinforce the material of the outer body portion 108. The particular additives or reinforced materials that are used depend upon the based material(s) used for forming the outer body portion 108 and the prosthetic device 100. In some instances the additives are distributed substantially uniformly through the base material(s) of the outer body portion 108. In other embodiments the deformation control element comprises only a defined portion of the outer body portion 108. In that regard, the deformation control element may extend along only a portion of the outer body portion 108, the deformation control element may be positioned within a particular portion of the outer body portion, and/or combinations thereof.

In other embodiments, the outer body portion 108 has a reinforcing layer that serves as the deformation control element and/or the pretensioning element. In some instances, the reinforcing layer includes a wire, cable, filament, thread, and/or structure extending therethrough The reinforcing layer increases the stiffness of the outer body portion 108 to limit the flexibility, deformity, and/or tensions the prosthetic device 100. In some embodiments, the reinforcing layer comprises a carbon fiber. In other embodiments, the reinforcing layer comprises a metal, polymer, or other material having an increased hardness and/or stiffness relative to the material comprising the central body portion 110. In some embodiments, at least a portion of the outer body portion 108 is formed around the reinforcing layer. In other embodiments, the reinforcing layer is inserted into the outer body portion 108 prior to curing of the prosthetic device 108. In some embodiments, the reinforcing layer is inserted into an opening in the body portion 108 and then additional material is inserted into the opening to close the opening and secure the reinforcing layer therein. The reinforcing layer has a cross-sectional profile configured to provide the desired stiffness, deformation properties, and/or tension to the outer body portion 108. Further the reinforcing layer is positioned within the outer body portion 108 appropriately to provide the desired stiffness, deformation properties, and/or tension to the outer body portion. In some embodiments, the outer body portion 108 includes multiple reinforcing layers therein. In that regard, the multiple reinforcing layers may be spaced equally about the outer body portion 108 and/or grouped into specific areas of the outer body portion. In some instances, the multiple reinforcing layers form a circumferential reinforcing wall extending from adjacent an upper surface of the prosthetic device to adjacent a lower surface of the prosthetic device.

In some embodiments, the outer body portion 108 includes one or more recesses and/or undercuts for receiving a component for defining the deformation properties of the outer body portion. For example, in some instances the component may be a wire, cable, or filament similar to those described above. In other instances, the component may be a material that is injected or otherwise introduced into the recess in the outer body portion 108. Generally, the size of the recess and the properties of the component are tailored to achieve the desired deformation properties and/or tensioning of the outer body portion 108. In some embodiments, the recess comprises between ⅛ and ⅔ of the height of the outer body portion 108 and between ⅛ and ⅔ of the width of the outer body portion. In many embodiments, the component substantially fills the entire recess 44. However, in some embodiments the component is sized such that it fills only a portion of the recess. In such embodiments, the remaining portion of the recess may remain vacant or be filled with another material. In some embodiments, the component is secured in the recess by the introduction of additional material into the open space remaining in the recess.

As noted above, the prosthetic device 100 is configured for use without being fixedly secured to the femur or tibia. However, in some embodiments the prosthetic device 100 includes a fixation member for engaging a portion of bone or surrounding tissue. In some such embodiments, the prosthetic device 100 includes fixation member extending down from the lower surface of the prosthetic device. The fixation member extends from the lower surface adjacent to and substantially parallel to the bridge 114 in some instances. In one embodiment, the fixation member comprises a keel structure configured to engage a complementary keyhole shaped groove that has been surgically incised in a portion of the tibia, such as the tibia plateau, according to a keyhole surgical approach. In another embodiment, the fixation member comprises a dovetail configured to engage a dovetailed groove prepared in the tibia. In other embodiments, the fixation member extends from other portions of the prosthetic device and/or in other directions, including directions substantially perpendicular to the bridge 114 and/or oblique to the bridge 114. Alternative positioning and orientations of the fixation member are used to accommodate alternative surgical approaches, patient specific anatomical attributes, meniscus specific orientations, physician preference, and/or other factors. The fixation member is manufactured as an integral part of the prosthetic device in some embodiments.

In some embodiments, a fixation device (e.g., bone screw, nail, staple, etc.) is utilized in combination with or in lieu of the fixation member to secure the prosthetic device 10 to the tibia. In that regard, the prosthetic device includes an opening or recess configured to receive and mate with the fixation device in some embodiments. Further still, in such embodiments where fixation is desired the bottom surface of the prosthetic device is coated with a bioactive coating to encourage the in-growth of natural tissue to further improve fixation of the prosthetic device to the tibial plateau in some instances. The coating is formed by grit blasting or spraying the bottom surface with any suitable material for encouraging tissue growth and, in some embodiment, is specifically adapted for promoting bone growth between the tibia and the prosthetic device.

In some instances, applying an internal pre-tension to the prosthetic device 100 maximizes the contact area of the upper and lower surfaces 116, 118 and distributes the loading in an optimal way, simulating the load distribution of a natural meniscus. Based on experimental and computational (e.g., finite element) analyses, it was found that applying an internal pretension to a meniscus prosthetic device such as prosthetic device 100 described above improves the device's functionality in terms of load bearing. In particular, pretensioning reduces the peak stresses applied on articular cartilage, increases the total load bearing threshold of the device, and improves the load distribution of the device.

In some embodiments the prosthetic device 100 comprises a pliable host material—such as PTG Bionate® Polycarbonate-Urethane (PCU), 80 Shore A—integrated with imbedded fibers—such as DSM Dyneema® fibers. In such embodiments, the imbedded fibers may be utilized to pretension the prosthetic device. Where the prosthetic device 100 has been pretensioned, the pliable host material gives the prosthetic device the ability to conform to the engaging surfaces of the femur and tibia as a function of load. On the other hand, the imbedded fibers bear more of the load than the pliable host material such that the risk for short-term failure of the prosthetic device is significantly decreased. In some instances, pretensioning is applied to a prosthetic device 100 that is smaller than the natural meniscus being replaced. In that regard, previous mechanical tests as well as finite element analyses have shown that pretensioning is effective when using a scaled-down implant. In some embodiments, the prosthetic device 100 subjected to pretensioning is scaled-down by 0.5 to 7.5% relative to the size of the natural meniscus being replaced and, in some instances, is scaled-down between about 2.0% and about 4.0%. In that regard, the specific size of the prosthetic device may be determined based on a specific candidate patient's knee structure. In some instances, the pretensioning of the device itself results in the reduced size of the device. Specifically, the tension of the fibers or other elements that tension the device cause the prosthetic device to contract or shrink in overall size. In other instances, the pretensioning of the device does not affect the size of the device. In some instances, upon loading within the knee joint the prosthetic device is expanded or stretched to a desired implantation size.

Add Contact Zones

In the pretensioned devices, contact between the prosthetic device 100 and the femur is reached initially at the outer body portion 108. which causes the central body portion 110 of the prosthetic device to be stretched as the weight is transferred through the femur to the prosthetic device and urges the outer body portion 108 outward. The engagement angles of the outer body portion 108 are such that compression forces applied to the device 100 are transferred at least partially to the reinforcing fibers. In some instances, the outer body portion 108 is urged outwardly and the central body portion 110 stretches upon weight being applied through the femur, rather than the femur simply compressing the outer body portion. This stretching of the central body portion 110 and the upper and lower articulation surfaces 116, 118 increases the contact area between the prosthetic device and the femur and tibia (see transition between FIGS. 9b and 10, for example) as well as lowers the average and peak loading stresses acting on the prosthetic device 100.

As shown in FIG. 9a, in some instances the reinforcing fibers 124 limit, restrict, or otherwise oppose outward movement or deformation of the outer body portion 108, but allow inward folding or collapsing of the device 100. The prosthetic device 100 is shown in a folded implantation orientation in FIG. 9a. In that regard, the bridge portion 114 is folded or collapsed towards the central body portion 110 to facilitate introduction of the device 100 into the knee joint. In some embodiments, the bridge 114 is both folded and compressed in this insertion configuration. In some instances, the bridge 114 is resilient such that it returns to its original, unfolded configuration after insertion (see FIG. 9b for example). In particular, once the bridge 114 reaches the other side of the femur 104 and has room to expand, it returns to its neutral position. Accordingly, in some surgical procedures a portion of the prosthetic device 100 is folded and/or compressed to facilitate insertion of the device into the knee joint. While the bridge 114 is illustrated as being folded/compressed in the present embodiment, in other instances other portions of the outer body portion 108 are folded and/or compressed.

As shown in FIG. 9b, upon initial contact between the femur and the tibia with the prosthetic device 100 there are gaps 182 between the upper surface 116 and the femur and gaps 184 between the lower surface 118 the tibia. In this regard, the initial contact of the bones 104, 106 and the prosthetic device 100 is with an upper constant contact area 186 and a lower constant contact area 188. The constant contact areas 186 and 188 are in constant contact with the femur and tibia, respectively, after insertion of the prosthetic device 100 into the knee joint. Accordingly, in some instances the constant contact areas 186 and 188 comprise an annular surface areas of the upper and lower portions of the device 100. In that regard, the constant contact areas 186 and 188 may comprise part of the outer body portion 108 or a combination of the outer body portion 108 and the central body portion 110. Within the upper and lower constant contact areas 186, 188 are upper and lower intermittent contact areas 190 and 192, respectively. The intermittent contact areas 190, 192 come into contact with the femur and tibia, respectively, upon sufficient loading of the prosthetic device 100. More specifically, as load is applied to the prosthetic device 100 the tapered surfaces of the constant contact areas 186, 188 urge the outer body portion 108 slightly outwardly such that the femur and tibia come into contact with the intermittent contact areas 190, 192. In some instances the pliable nature of the prosthetic devices material allows the intermittent contact areas 190, 192 to conform to the shape of the bearing condyles of the femur and tibia upon loading. In this manner, the intermittent contact areas 190, 192 do not constantly engage the femur and tibia as the constant contact areas 186, 188 do. In some instances, the intermittent contact areas 190, 192 are circumferentially or annularly bounded and/or defined by the constant contact areas 186, 188, respectively. Further, in some embodiments, additional intermittent contact areas 190, 192 are included outside of the constant contact areas 186, 188. Thus, in some instances, the intermittent contact areas 190, 192 comprise part of the central body portion 110 and/or outer body portion 108. In some embodiments, the constant contact areas 186, 188 extend to the perimeter of the device 100 such that the intermittent contact areas are solely within the constant contact areas. In some instances, the constant contact areas 186, 188 are shaped to substantially match a contour of the femur and/or tibia. Referring to FIG. 1, shown therein is one example of an orientation of an upper constant contact area 186 and an intermittent contact area 190.

Referring to FIG. 10, as the prosthetic device 100 is subjected to weight bearing between the femur and tibia, the outer body portion is urged outwardly and the central body portion 110 stretches to achieve the substantially uniform contact between the upper and lower surfaces 116, 118 and the femur and tibia. As shown, the gaps 182, 184 are eliminated and the intermittent contact areas 190,192 as well as the constant contact areas 186, 188 are in contact with the femur and tibia, respectively. The pliability of the material of the central body portion 110 facilitates the continuous contact as the material is able to conform to the shape of the engaging surfaces of the femur and tibia, which comprise cartilage in some instances. Further, the stretching and mating of the prosthetic device 100 reduces the translation and rotation of the prosthetic device within the knee joint. The reduced translation and rotation of the prosthetic device serves to limit wear damage to the cruciate ligaments over time.

Prosthetic Device Selection

In some embodiments, a prosthetic device is selected for a patient from a finite library or catalog of available prosthetic device. In that regard, the available prosthetic devices are of various sizes, various materials, and/or various shapes. In some instances, a selection methodology is applied to identify one or more suitable prosthetic devices and/or a best prosthetic device for a patient based on the patient's anatomical features. In other instances, a custom prosthetic device is designed and manufactured specifically for the patient based on the patient's anatomical features. Specific methods for identifying an appropriate prosthetic device for a patient will now be described. It is recognized that the methods described herein may be used individually, combined with one another, and/or combined with other methods in an effort to identify a suitable prosthetic device for the patient.

In most healthy patient knees, the natural meniscus and the surrounding bone structures have substantially matching geometrical contours. Accordingly, in order to restore the function of the knee joint with a prosthetic meniscus, the prosthetic device should be configured to substantially match the geometrical contours of the surrounding bone structures of the knee joint after implantation. Thus, in some embodiments the geometrical attributes of the patient's knee joints and the prosthetic device are taken in consideration. In that regard, the both the patient's healthy knee and the patient's damaged knee are considered, including the bone structures, the articular cartilage, and/or the menisci.

Figure 11:
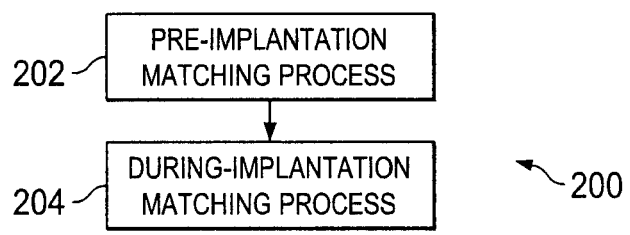
FIG. 11 is a block diagram of an embodiment of a method according to one aspect of the present disclosure for selecting an appropriate prosthetic device for use with a patient's knee.
Figure 12:
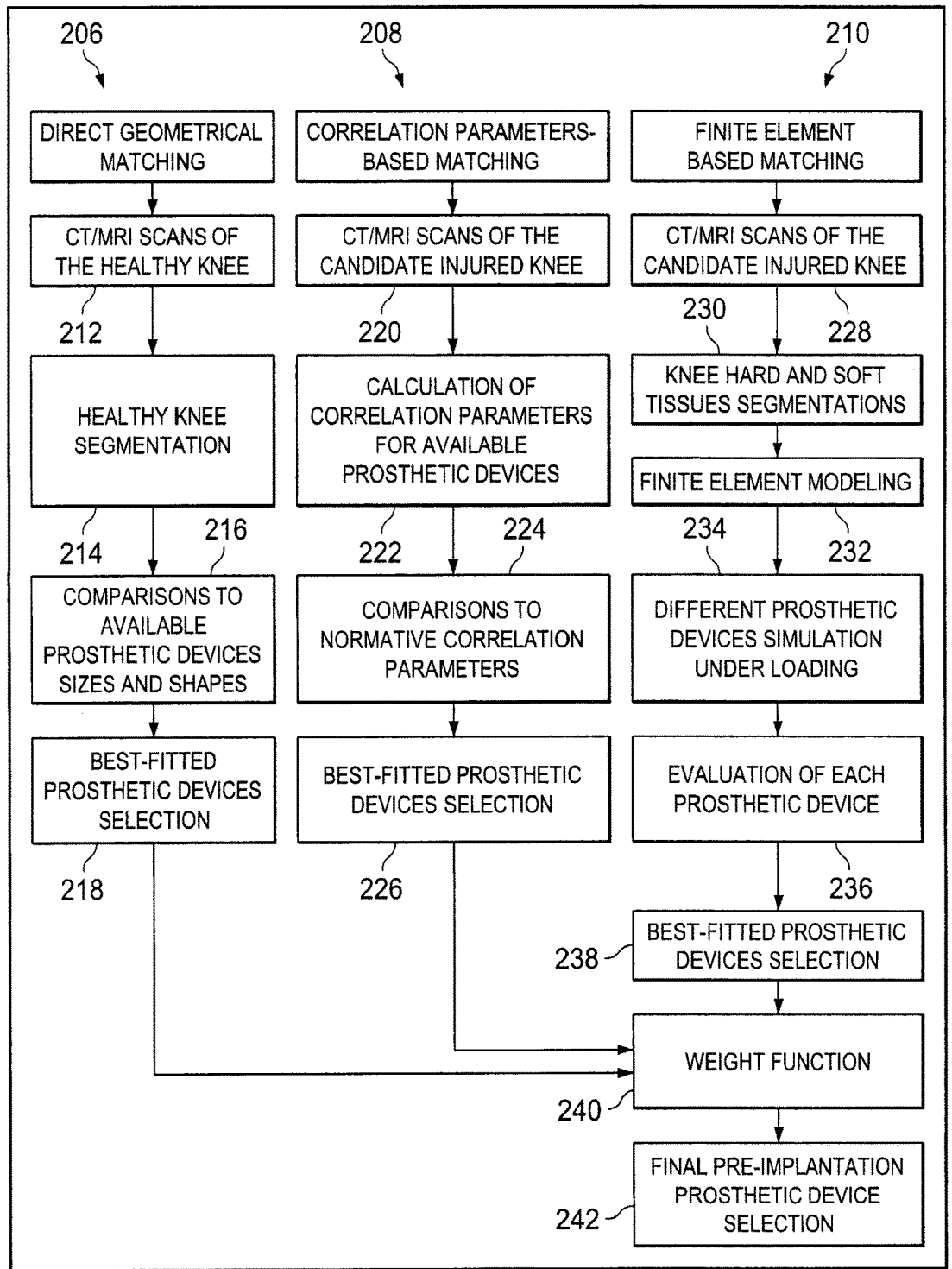
FIG. 12 is a block diagram of an embodiment of a method according to one aspect of the present disclosure for selecting an appropriate prosthetic device for use with a patient's knee prior to surgery.

Referring now to FIG. 11, shown therein is a method 200 for identifying at least one suitable prosthetic device for a patient. The method 200 includes a pre-implantation matching process at step 202 and a during-implantation matching process at step 204. The pre-implantation and during-implantation matching procedures 202 and 204 described herein are utilized for both medial and lateral meniscus replacements in both the left and right knees. The method 200 begins at step 202 with the pre-implantation matching process. The pre-implantation matching process of step 202 is comprised of one or more matching methods. Referring more specifically to FIG. 12, in the present embodiment the pre-implantation matching process 202 comprises three different matching methods: a direct geometrical matching method 206, a correlation parameters-based matching method 208, and a finite element-based matching method 210. Each of these three matching processes 206, 208, and 210 will be described in greater detail below. While these processes 206, 208, and 210 are described as being used together, in some instances only one or two of the three methods are utilized in the pre-implantation matching process 202. In other instances, the processes 206, 208, and 210 are utilized in combination with additional and/or alternative matching processes.

Figure 13:
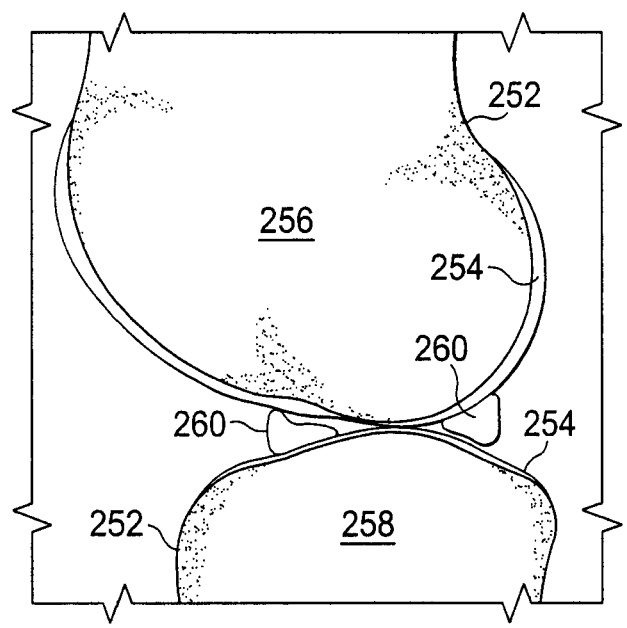
FIG. 13 is a diagrammatic side view of a rendering knee joint where the bone, articular cartilage, and meniscus have been segmented according to one aspect of the present disclosure.
Figure 14:
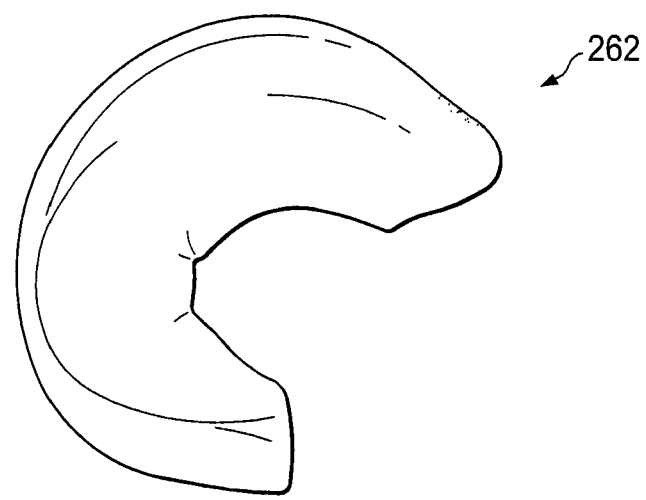
FIG. 14 is a diagrammatic perspective view of a three-dimensional reconstruction of a natural meniscus according to one aspect of the present disclosure.
Figure 16:
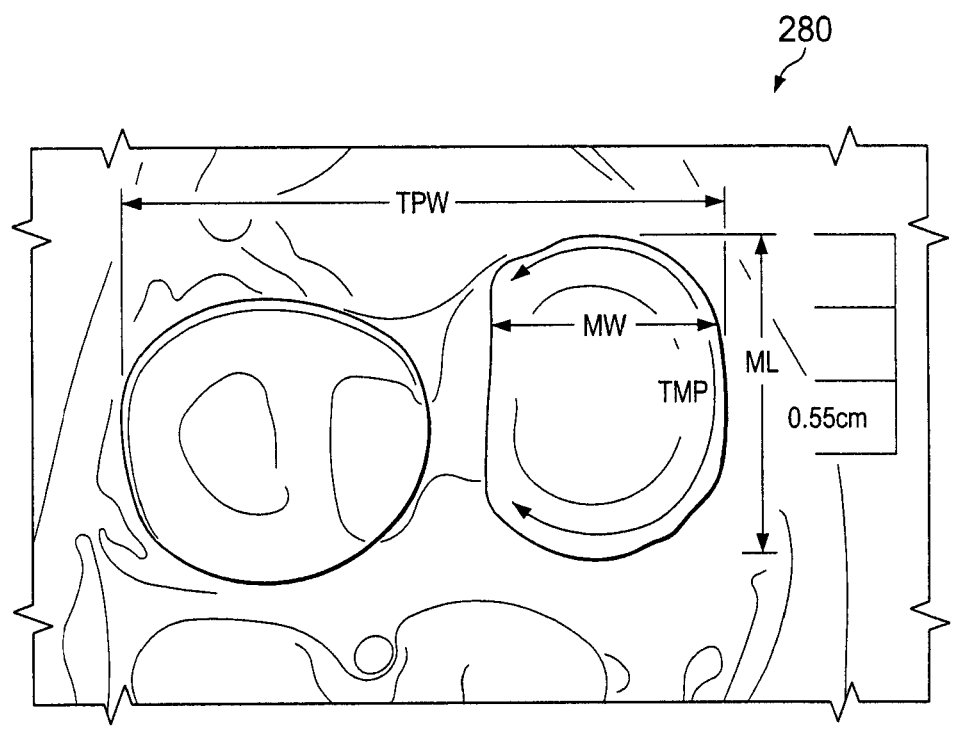
FIG. 16 is a cross-sectional top view of a knee joint based on an MRI and/or CT scan of the knee joint identifying measurements of the anatomical features of the knee joint according to one aspect of the present disclosure.

The direct geometrical matching process 206 begins at step 212 where CT and/or MRI scans of the healthy knee of a candidate patient are obtained. In some instances, the CT and/or MRI scans of the healthy knee are utilized to identify the appropriate for measurements the prosthetic device for the damaged knee. At step 214, the healthy knee joint is segmented into its various components. In some embodiments, image-processing algorithms are utilized to segment the knee joint. In some embodiments, one or more of the bone surfaces, the articular cartilage, and the meniscus of the knee joint are segmented. For example, referring to FIG. 13, shown therein is a diagrammatic side view of a patient's right knee joint 250 where the bone surfaces 252 and articular cartilage 254 of the femur 256 and the tibia 258 have been segmented. Further, the medial meniscus 260 extending between the articular cartilage 254 has been segmented. In some instances, the bone surfaces, the articular cartilage, and the meniscus are segmented in separate steps. In other instances, the segmentation of the bone surfaces, the articular cartilage, and the meniscus are performed approximately simultaneously. In some embodiments, the internal knee joint cavity is characterized based on the surfaces of the articular cartilage. In some instances, the healthy meniscus is defined at least partially based on the knee joint cavity defined by the articular cartilage. In some embodiments, at step 214 or a subsequent step of the direct geometrical matching process 206, a virtual solid model 262 of the healthy meniscus 260 is built graphically, as shown in FIG. 14. In some embodiments, the virtual solid model 262 is created in a stereolithography ("STL") format. The virtual model 262 is used in some instances to compare the healthy meniscus 260 to the available prosthetic devices.

In the present embodiment, at step 216, the segmented healthy meniscus is compared to available prosthetic devices. In some instances, this comparison includes comparing the relative sizes and shapes in terms of linear dimensions (such as depths, widths, heights, and/or radii of curvature) in the different sections or regions of the meniscus; outer surfaces (such as upper and lower contact surfaces and/or peripheral surfaces); and volumes. In some embodiments, each prosthetic device is given a score or ranking based on how well it matches each of the various dimensions of the natural meniscus. By combining the scores for each of the dimensions, an overall score is obtained for each available prosthetic device. In that regard, it is understood that the various dimensions are weighted in some embodiments to emphasize the importance of certain dimensions. The importance or weighting of the various dimensions are determined by such factors as the patient's age, activity level, weight, and/or other factors considered by the treating medical personnel. In some instances, the weighting function is determined by a computer system based on the answers provided to prompted questions. In other instances, the treating medical personnel manually set the weighting function of the various dimensions.

In that regard, it is understood that the best prosthetic device or a prosthetic device that will obtain the best score for a particular dimension is not necessarily one with the exact same measurements as the natural meniscus. Rather, in some embodiments of the present disclosure the prosthetic device is approximately the same size or smaller than a natural healthy meniscus. In some embodiments the prosthetic device is generally between about 5% and about 20% smaller than the natural meniscus in its relaxed pre-implantation state. Similarly, in some embodiments of the present disclosure the prosthetic device does not match the shape of the natural meniscus. For example, FIG. 22 is a diagrammatic perspective view of a prosthetic device 244 for use in replacing a damaged natural meniscus according to the present disclosure shown in comparison to the dimensions of a healthy natural meniscus 246. As illustrated, the prosthetic device 244 does not match the dimensions of the natural meniscus 246. In some embodiments, the best prosthetic device is substantially the same size and shape as the natural meniscus. At step 218, one or more of the best-graded prosthetic devices is selected for the direct geometrical matching method as a suitable implant for the specific candidate knee. In some embodiments, only a single, best prosthetic device is identified by the geometrical matching process 206 at step 218. In other embodiments, all of the available prosthetic devices are ranked based on their score as calculated using the geometrical matching process 206. In yet other embodiments, all of the prosthetic devices suitable for the candidate knee are identified and the prosthetic devices that are not suitable are discarded as potential implant options.

While the measurements and comparisons of the patient's knee and meniscus have been described as being performed substantially by electronic or automated means, in some embodiments the measurements are taken manually, directed form CT/MRI scans. Further, these manual measurements may be compared with prosthetic device measurements. The prosthetic device measurements are provided by the manufacturer in some instances. In other instances, the measurements of the prosthetic device are obtained manually as well. The manual measurements may be utilized to confirm the measurements and comparisons obtained using the image processing algorithm and matching process or in lieu of the image processing algorithm and matching process. Further, while the present disclosure discusses the use of CT and/or MRI scans, it is fully contemplated that other medical imaging methods may be utilized. Accordingly, it is fully contemplated that alternative medical imaging devices and methods may be utilized with any and all of the methods described herein.

The correlation parameters-based matching process 208 is utilized in some embodiments. The correlation parameters-based matching process utilizes dimension measurements based on one or more large-scale studies of patients having healthy knees. Generally, the studies considered the dimensions of the patients' knees and defined "normal" or acceptable ranges. In some instances, geometrical relationships or formulas based on the measured dimensions of the bones and the menisci were calculated for each healthy subject. These geometrical relationships or formulas define the correlation parameters utilized for selecting an appropriate prosthetic device in some embodiments of the present disclosure.

Referring now to FIG. 15, shown therein is a chart setting forth various correlation parameters according to one aspect of the present disclosure. In the present embodiment, five correlation parameters are identified: area, width, length, perimeter, and coronal relation. In other embodiments, a greater or fewer number of correlation parameters are utilized. Each of the correlation parameters is defined by formula or equation comprised of dimensional measurements of the knee joint. These measurements are based on CT and MRI scans of the healthy subject patients of the large-scale studies in some instances. The area correlation parameter is defined by the meniscus contact area divided by the tibia medial area, or $$A = \frac{MA}{TMA}.$$

The width correlation parameter is defined by the average meniscus width divided by the medial tibia width, or $$W = \frac{MW_{avg}}{TMW},$$

where the average meniscus width is the average of the anterior meniscus width and posterior meniscus width, or $$MW_{avg} = \frac{MW_A + MW_P}{2}.$$

The length correlation parameter is defined by the medial meniscus length divided by the tibia medial length, or $$L = \frac{MML}{TML}.$$

The perimeter correlation parameter is defined by the meniscus perimeter divided by the tibia medial perimeter, or $$P = \frac{MP}{TMP}.$$

The coronal relation correlation parameter is defined by the meniscus coronal width divided by the tibia coronal width, or $$C = \frac{MW_C}{TCW}.$$

The mean and standard deviation are calculated for each correlation parameter in the large scale studies. The means and standard deviations are considered as the knee normative data or acceptable ranges. According to one large scale study, the normative data ranges were as follows. The average coronal tibia width was 75.6 mm with a standard deviation of 6.7 mm or 8.8%. The average meniscus width as measured in the coronal plane was 32.1 mm with a standard deviation of 3.1 mm or 9.6%. The average tibia medial length was 48.8 mm with a standard deviation of 5.2 mm or 10.6%. The average tibia area was 1282.8 mm with a standard deviation of 227.2 or 17.7%. The average tibia medial perimeter was 92.9 mm with a standard deviation of 9 mm or 10.4%. The average anterior meniscus width was 28.7 with a standard deviation of 10.3 mm or 35.8%. The average posterior meniscus width was 28.7 mm with a standard deviation of 10.4 mm or 36.3%. The average medial meniscus body width was 6.7 mm with a standard deviation of 11.7 mm or 173.3%. The average medial meniscus length was 44.5 mm with a standard deviation of 9.5 or 21.3%. The average meniscus perimeter was 87.6 mm with a standard deviation of 9.5 mm or 10.8%. The average anterior meniscus height was 6.9 mm with a standard deviation of 11.7 mm or 169.6%. The average posterior meniscus height was 7.4 mm with a standard deviation of 11.6 mm or 157.4%. The average medial meniscus height was 6.9 mm with a standard deviation of 11.6 mm or 167.2%. The average meniscus oval area was 965.68 mm with a standard deviation of 186.64 mm or 19.3%.

Based on these normative data ranges, the following correlation parameter ranges were determined. The average area correlation parameter was 0.75 with a standard deviation of 0.08 or 10.77%. The average perimeter correlation parameter was 0.95 with a standard deviation of 0.05 or 5.0%. The average width correlation parameter was 0.87 with a standard deviation of 0.06 or 6.6%. The average length correlation parameter was 0.91 with a standard deviation of 0.07 or 8.0%. The average coronal relation correlation parameter was 0.37 with a standard deviation of 0.03 or 7.1%. It is contemplated that additional large-scale studies may be performed in the future and that the accepted ranges for the correlation parameters discussed herein below may be adjusted as necessary to conform with the accepted dimensional ranges in the field.

Figure 17:
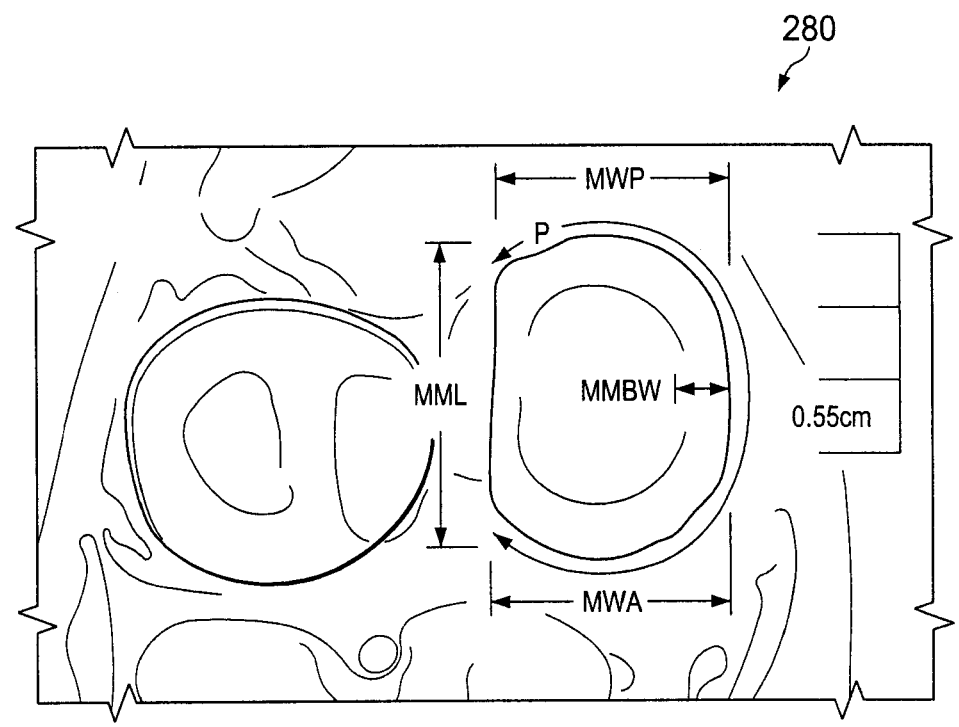
FIG. 17 is a cross-sectional top view of a knee joint based on an MRI and/or CT scan of the knee joint similar to that of FIG. 16, but identifying measurements of other anatomical features according to one aspect of the present disclosure.
Figure 18:
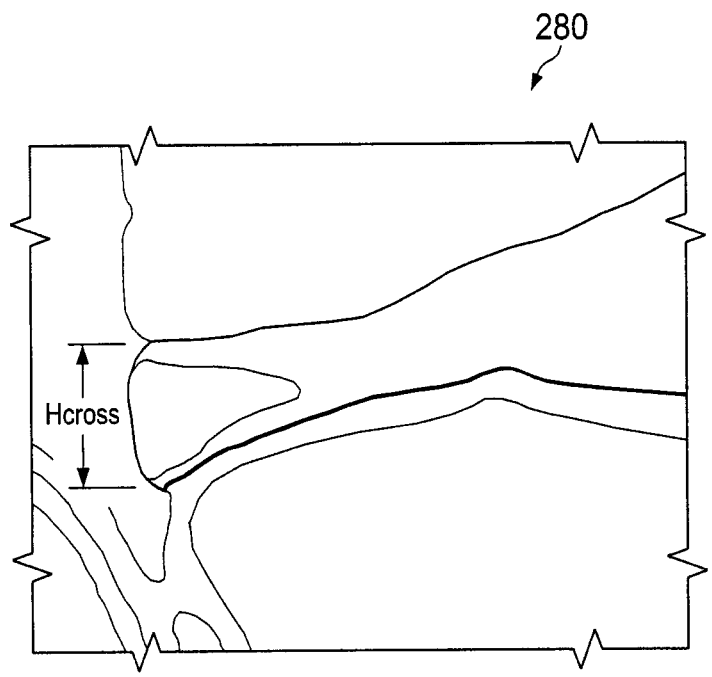
FIG. 18 is a cross-sectional sagittal view of a knee joint based on an MRI and/or CT scan of the knee joint identifying a medial meniscus height according to one aspect of the present disclosure.
Figure 19:
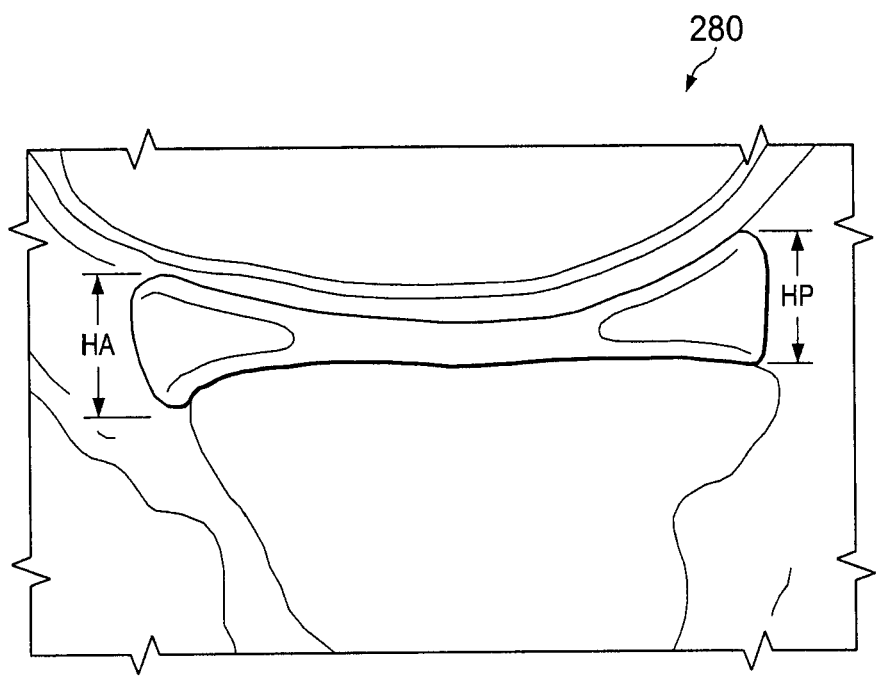
FIG. 19 is a cross-sectional side view of a knee joint based on an MRI and/or CT scan of the knee joint identifying anterior and posterior meniscus heights according to one aspect of the present disclosure.

Referring now to FIGS. 16-19, shown therein are various views of a knee joint 280 based on MRI and/or CT scans identifying measurements of the anatomical features of the knee joint. For example, referring more specifically to FIG. 16, a cross-sectional top view of the knee joint 280 identifying various measurements of the anatomical features is provided. In particular, the width of the meniscus as measured in the coronal plane (labeled MW) and the coronal tibia width (labeled TPW) are identified. These parameters are utilized for calculating the coronal relation as described above. Further, the tibia medial length (labeled ML) is identified along with the tibia medial perimeter (labeled TMP). Referring more specifically to FIG. 17, a cross-sectional top view of the knee joint 280 similar to that of FIG. 16, but identifying measurements of other anatomical features is provided. Specifically, the anterior and posterior meniscus widths (labeled MWA and MWP, respectively) are provided. Also, the medial meniscus length (labeled MML)

and the meniscus perimeter (labeled P) are provided. Finally, the medial meniscus body width (labeled MMBW) is provided. Referring to FIG. 18, a cross-sectional sagittal view close-up of the knee joint 280 identifying the medial meniscus height (labeled Hcross) is provided. Finally, referring to FIG. 19, a cross-sectional side view close-up of the knee joint 280 identifying anterior and posterior meniscus heights (labeled HA and HP, respectively) is provided. It is fully contemplated that additional and/or alternative views of the knee joint 280 be provided. In addition, it is fully contemplated that additional and/or alternative measurements of the knee joint 280 be provided.

The correlation parameters-based matching process 208 begins at step 220 where CT and/or MRI scans of the injured knee of a candidate patient are obtained. Based on the imaging of the injured knee, various anatomical measurements of the knee can be obtained. For example, in some instances it is desirable to obtain information regarding the dimensions of the tibia. In that regard, the dimensions of the tibia discussed above with respect to the correlation parameters (e.g., tibia medial area, tibia medial width, tibia medial length, tibia medial perimeter, tibia coronal width, and/or other tibia dimensions) are obtained in some instances.

The process 208 continues at step 222 where the correlation parameters for one or more of the available prosthetic devices are determined. The geometrical relationship formulas of the correlation parameters are calculated for the prosthetic device based on the available candidate knee data and compared to the accepted normative data for each prosthetic device. Each prosthetic device is given a sub-grade for each correlation parameter based on how well the device matches up with the accepted ranges for that correlation parameters. In that regard, an acceptable range of values for the prosthetic device can be determined based the available measurements of the candidate knee and the normative data (e.g., normative range ±standard deviation) for the candidate knee. For example, with respect to the area correlation parameter, the acceptable range of meniscus contact areas for the prosthetic devices can be determined by multiplying the normative range of acceptable areas by the tibia medial area, or A×TMA=MA. The acceptable ranges for other aspects of the prosthetic device may be calculated similarly for each of the correlation parameters.

The process 208 continues at step 224 where the calculated correlation parameters are compared to the normative or accepted correlation parameters. Depending on how well the prosthetic device fits within the range for each correlation parameter, a sub-grade is determined for that parameter. The better the fit, the better the sub-grade for that parameter. In some instances, the grades are binary. Meaning if the device is within the acceptable range it receives the best score and if the device is outside of the range it receives the worst score. Similar to the previous geometrical matching method, the best-graded prosthetic device is calculated by adding up all of the sub-grades to determine an overall grade. In that regard, it is understood that the various correlation parameters are weighted in some embodiments to emphasize the importance of certain correlation parameters. The importance or weighting of the correlation parameters are determined by such factors as the patient's age, activity level, weight, and/or other factors considered by the treating medical personnel. In some instances, the weighting function for the correlation parameters is determined by a computer system based on the answers provided to prompted questions. In other instances, the treating medical personnel manually set the weighting function for the correlation parameters.

Further, it is understood that the correlation parameters may vary depending on the type of implant being considered. For example, in some embodiments of the present disclosure the prosthetic devices are designed to be between about 5% and about 20% smaller than the natural meniscus in its relaxed pre-implantation state. Accordingly, such sizing can be taken into consideration when determining the acceptable ranges of the dimensions for the prosthetic device as they relate to the correlation parameters. At step 226, one or more of the best-graded prosthetic devices is selected for the correlation parameters-based matching process 208 as a suitable implant for the specific candidate knee. In some embodiments, only a single, best prosthetic device is identified by the correlation parameters-based matching process 208. In other embodiments, all of the available prosthetic devices are ranked based on their score as calculated using the correlation parameters-based matching process 208. In yet other embodiments, all of the prosthetic devices suitable for the candidate knee are identified and the prosthetic devices that are not suitable are discarded as potential implant options.

The finite element-based matching process 210 is utilized in some embodiments. The finite element-based matching process 210 begins at step 228 where CT and/or MRI scans of the injured knee of a candidate patient are obtained. In some instances, the same CT and/or MRI scans are utilized for both the finite element-based matching process 210 and the correlation parameters-based matching 208. Similar to the direct geometrical matching process 206 discussed above with respect to the healthy knee joint, at step 230 the injured knee joint of the patient is segmented into its various components, such as the bone, articular cartilage, and menisci. In some instances, a three-dimensional solid geometry model of the bones, cartilage, and menisci of the injured knee is built. Based on the solid geometry, a patient-specific finite element model of the knee is created at step 232. The patient-specific finite element model is configured to interface with various finite element models of prosthetic devices in some instances. In that regard, in some embodiments the finite element model does not include the natural meniscus. Further, in some instances a finite element model of the patient's healthy knee is created for use in evaluating the effectiveness of the prosthetic devices in the injured knee.

The finite element-based matching process 210 continues at step 234 where several simulation cases using the finite element model are tested. First, in some embodiments a load of up to 3-times the patient's body-weight is applied by the femur on the natural, damaged meniscus. In other embodiments, the simulation of loading on the damaged meniscus is omitted. In other embodiments, a simulation of loading of the natural meniscus of the patient's healthy knee is performed and utilized as a base line. Regardless of whether a damaged or healthy meniscus is utilized, peak and average pressure measurements across the meniscus, peak and average pressure measurements acting on the femoral and tibial articular cartilage, pressure distributions across the tibialis plateau, and/or other measurements are calculated.

Figure 20:
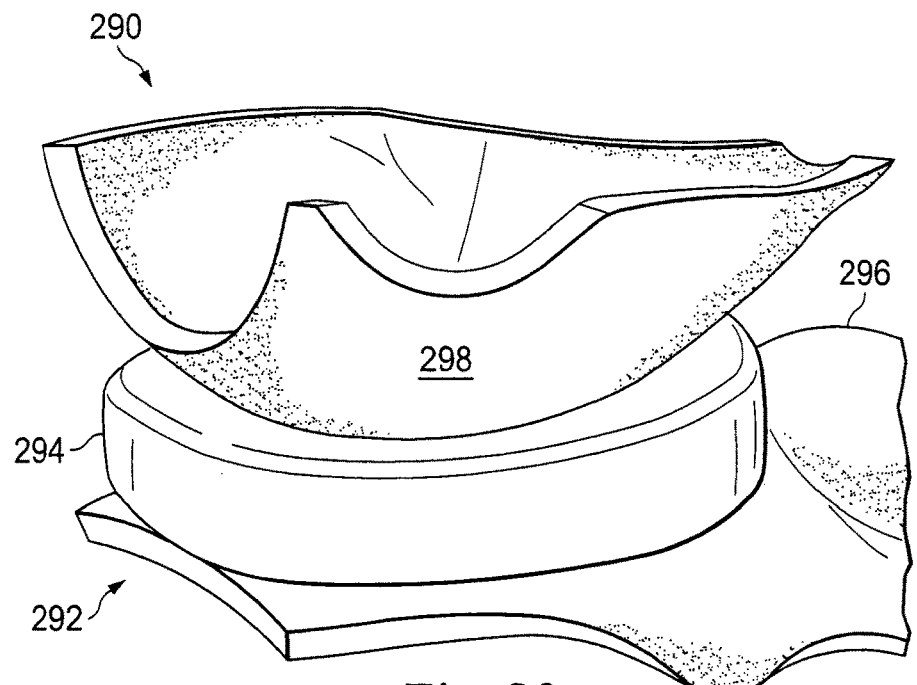
FIG. 20 is a diagrammatic perspective view of a three-dimensional finite element model of a knee joint according to one aspect of the present disclosure.
Figure 21:
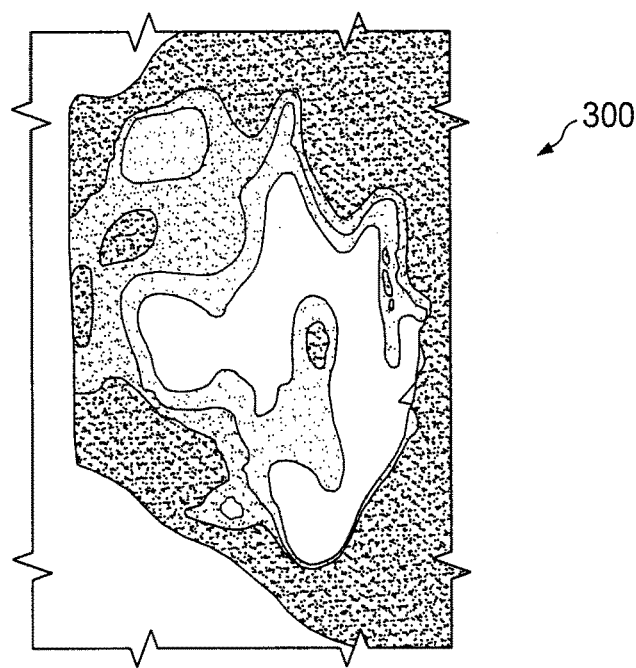
FIG. 21 is a rendering of a simulated contact pressure map between a prosthetic device and a tibialis plateau according to one aspect of the present disclosure.

Step 234 also includes testing one or more available prosthetic devices under a simulated load. Referring to FIG. 20, shown therein is a three-dimensional finite element model 290 of a knee joint 292 with a prosthetic device 294 positioned between a tibialis plateau 296 and a femur 298 according to one aspect of the present disclosure. For each of the available prosthetic devices, peak and average pressure measurements across the prosthetic device, peak and average pressure measurements acting on the femoral and tibial articular cartilage, pressure distributions across the tibialis plateau, and/or other measurements are calculated. Referring to FIG. 21, shown therein is a simulated contact pressure map 300 for the prosthetic device 294 of FIG. 20 illustrating contact pressures between the prosthetic device and the tibialis plateau 296.

At step 236, the resultant pressure measurements for each of the prosthetic devices are compared to industrial accepted values and/or the natural, healthy meniscus to provide the prosthetic devices with sub-grades for each of the measurements. For example, the peak pressure measurements of each of the prosthetic devices are compared to the accepted ranges or the peak pressure measurements of the natural, healthy meniscus. The extent to which the prosthetic device is within the accepted range determines the device's sub-grade for peak pressure. Similarly, the peak and average pressure acting on the articular cartilages are compared to the allowed natural values for each prosthetic device and the prosthetic device is given sub-grades accordingly. Further, the tibialis plateau pressure distributions for each prosthetic device are compared to those of a healthy natural meniscus in terms of contact area size and stress concentrations. In one particular embodiment, a prosthetic device is given a perfect sub-grade score if the resultant pressure distribution across the tibialis plateau is within ±15% of a healthy natural meniscus.

By combining the scores for each factor of the loading simulations, an overall score is obtained for each available prosthetic device. In that regard, it is understood that the various factors or measurements are weighted in some embodiments to emphasize the importance of certain aspects of the prosthetic device. The importance or weighting of the various factors are determined by such factors as the patient's age, activity level, weight, and/or other factors considered by the treating medical personnel. In some instances, the weighting function is determined by a computer system based on the answers provided to prompted questions. In other instances, the treating medical personnel manually set the weighting function of the various dimensions.

In some instances, the finite element-based matching process 210 includes motion simulations in addition to or in lieu of the load bearing simulations discussed above. In that regard, the motion of the knee joint is compared to that of natural, healthy meniscus for one or more available prosthetic devices. In some instances, these simulations are designed to simulate typical patient movements such as walking, running, riding a bicycle, standing up, sitting down, etc. The prosthetic devices are then provided sub-grades based on their performance for various factors related to knee movement (e.g., position and/or loading support at various degrees of flexion). In some embodiments, the loading simulations and motion simulations are combined such that the devices are scored base on loading functions during the motion simulations.

In some instances, the finite element-based matching process is compared to a generic model rather than a patient specific model. For example, in some embodiments a plurality of finite element models are provided corresponding to variety of different knee sizes and/or knee types. A specific finite element model from the plurality of different finite element models is selected for the current patient. In some embodiments, the specific finite element model is based at least partially on the knee size of the current patient. In one instance, the selected model is determined based on MRI data of the patient. Further, in some instances the selection of the specific finite element model is at least partially based on correlation parameters—such as those discussed above with respect to the correlation-based matching process 208—or the candidate knee. In some instances, each of the available prosthetic devices is tested or simulated with respect to each of the finite element models and the functionality of each the prosthetic devices is compared to the accepted values for a natural, healthy meniscus. Accordingly, for each of the finite models one or more suitable prosthetic devices are identified. Thus, using only the associated bone measurements from the CT and/or MRI scans of a candidate knee, a best-matched finite element model is identified and, from the best-matched finite element model, the corresponding suitable prosthetic devices are identified as suitable devices for the current patient.

In some embodiments, the pre-implantation matching method 202 continues at step 240 by weighting the answers provided by the direct geometrical matching process 206, the correlation parameters-based matching process 208, and the finite element-based matching process 210. In some embodiments, each of the matching processes 206, 208, and 210 are given equal weight. However, in other embodiments the matching processes 206, 208, and 210 are given unequal weights. For example, where a generic finite element model has been utilized rather than a patient-specific generated finite element model—the finite element model-based correlation may be given less weight than the direct geometrical matching process 206 and the correlation parameters-based matching process 208. The determination of the weighting of the different matching processes 206, 208, and 210 is determined by the treating medical personnel in some instances. Finally, the pre-implantation matching method 202 continues at step 242 with the identification of one or more suitable prosthetic devices are identified. In some embodiments, a single "best" prosthetic device is identified by the pre-implantation matching method 202. In other embodiments, two or more suitable prosthetic devices are identified. In that regard, where two or more suitable prosthetic devices are identified a specific prosthetic device may be selected by the during-implantation matching process 204.

Referring to FIGS. 11 and 23, after the pre-implantation matching process at step 202, the method 200 continues at step 204 with a during-implantation matching process. The during-implantation matching process 204 begins at step 310 with the selection of at least two suitable trial prosthetic devices. In some embodiments, the suitable trial prosthetic devices are identified by the pre-implantation matching process 202 described above. In some embodiments, three trial prosthetic devices are selected. Further, in one particular embodiment three different sizes of a prosthetic device are selected. In other embodiments, the selected prosthetic devices may be substantially different in shape, materials, function, and/or other properties. In some embodiments, the trial prosthetic devices are substantially similar to the prosthetic devices that are to be permanently implanted. In some embodiments, the trial implants are the actual prosthetic devices that are to be permanently implanted. In one embodiment, each trial has a similar external geometry to the final implant and is formed of a material having similar strength properties to the final implant. However, the trial lacks the reinforcing fibers or layer. Thus, the trial may be more easily removed from the knee joint than the final implant. Further, in some instances, the trial includes a visual indicator such as a marking (e.g., "TRIAL") on the exterior or a dye in the polymer resin to readily distinguish the trial from the final implant. In some instances, the trials include radiopaque markers imbedded therein to distinguish them from the final implant.

The during-implantation matching process 204 continues at step 312 with an in vivo physical testing of the prosthetic device. Generally, the in vivo testing comprises introducing the trial prosthetic device into the knee joint and moving the knee joint through a series of movements. At step 314, the surgeon considers the fit of each prosthetic device trial and the corresponding movement of the knee joint. Based on the surgeon's observations at step 314, the during-implantation matching process 204 concludes at step 316 with the final selection of the best prosthetic device for the patient. Subsequently, the surgeon implants the selected prosthetic device into the patient. In some instances, the prosthetic device is implanted according to methods described herein.

Utilizing the during-implantation matching process 204, the surgeon can decide, based on actual physical tests, which prosthetic device best fits a candidate knee. In that regard, in some embodiments the pre-implantation matching process is utilized to identify two or more prosthetic devices that are suitable for use in the candidate knee. The during-implantation matching process is then utilized to select the best of the suitable prosthetic devices. Accordingly, the during-implantation matching process 204 may be utilized to confirm the results of the pre-implantation matching process 202 in some instances. In some embodiments, trial implants are utilized in the during-implantation matching process for selecting the appropriate sized prosthetic device and then the actual prosthetic device of that size is subsequently implanted. In some embodiments, three sizes of prosthetic devices and/or trials are taken to surgery. Typically, the three sizes will be the best fit prosthetic device identified in the pre-implantation matching process, and prosthetic devices slightly larger and slightly smaller than the best fit device. According to the fit within the actual candidate knee the surgeon identifies the best prosthetic device to use. After identifying the best fit prosthetic device during surgery, the surgeon implants the surgical device.

Surgical Protocols

Referring now to FIG. 24, shown therein is a block diagram of a surgical protocol 320 according to one aspect of the present disclosure. Generally, the surgical protocol 320 relates to the implantation of a prosthetic device into the knee joint of a patient. In the specifically described embodiments, the surgical protocol 320 relates to the implantation of a surgical device for replacing a medial meniscus. In other embodiments, similar surgical protocols are utilized for replacing a lateral meniscus with a surgical device. In some instances, the surgical procedure replaces both the medial and lateral menisci with a prosthetic device.

The surgical protocol 320 begins at step 322 where an arthroscopy is performed. In some embodiments, a leg holder or post is utilized. In such embodiments, the leg holder or post may be utilized in subsequent steps to facilitate application of a valgus force, ease insertion of implant, and/or otherwise assist in the performance of the surgery. The arthroscopy is a routine arthroscopy in some embodiments. The surgical protocol 320 also addresses any additional inter-articular pathologies as needed at step 322.

The surgical protocol 320 continues at step 324 with an evaluation of the articular cartilage of the knee joint. In some embodiments, the integrity of the articular cartilage positioned within the medial compartment is evaluated. Generally, the evaluation of the articular cartilage is to confirm that the patient's knee is suitable for receiving the prosthetic device intended to be implanted. In some instances, the articular cartilage is evaluated to identify defects in the articular cartilage such that these defects may be treated or otherwise addressed prior to implantation of the prosthetic device.

The surgical protocol 320 continues at step 326 where the meniscus and the fat pad are excised. In that regard, in some embodiments the meniscus is entirely removed (total meniscectomy). In other embodiments, the meniscus is partially removed (partial meniscectomy) to allow for the introduction of the prosthetic device into the knee joint. Generally, the fat pad is excised only to the degree necessary for exposure or access to the meniscus and/or medial compartment of the knee joint. Accordingly, in some instances the fat pad remains substantially intact. In other embodiments, a substantial portion of the fat pad may be removed.

The surgical protocol 320 continues at step 328 with an enlarging of the medial portal. Generally, the medial portal is the same portal created by the arthroscopy of step 322. However, in some embodiments the medial portal is separate from the portal created by the arthroscopy. In some embodiments, the incision is adjacent to the medial border of the patella tendon. The medial portal is enlarged to accommodate the insertion of the prosthetic device or implant into the knee joint. In some embodiments, the incision or portal is enlarged to a size between approximately 4.0 cm and approximately 6.0 cm. However, depending on the size of the implant, the flexibility of the implant, and/or other factors, the size of the opening may be larger or smaller in other instances.

The surgical protocol 320 continues at step 330 with accessing the medial cavity of the knee joint. In some instances, accessing the medial cavity comprises opening the capsule and retinaculum to provide access to the medial cavity. Further, in some instances any remaining portions of the anterior meniscus rim are removed or excised when gaining access to the medial cavity.

After gaining access to the medial cavity, the surgical protocol 320 continues at step 332 with the insertion of one or more trial implants into the knee joint. The trial implants may represent different sizes of the same implant, different types of implants, and/or combinations thereof. In some embodiments, the trial implants are identified in a pre-implantation matching or selection method. In one particular instance, the pre-implantation matching process 202 discussed above is utilized to identify one or more suitable implants for which trial versions of the implant may be obtained. In some instances, the trial implants are substantially similar in size and shape to the actual implant that will be permanently implanted in the patient. In some instances, the only difference between the trial implant and the actual implant is the material from which the implant is made. Specifically, in one embodiment, the trial does not include reinforcing fibers. In some instances, the trial implant and the actual implant are identical copies of one another. In some instances, a single implant is used as both the trial and actual implant.

Generally, a first trial implant is inserted into the knee joint. In some instances, the first trial implant is representative of the implant identified as the most suitable implant in a pre-implantation selection process. After insertion of the trial implant into the knee joint, the functionality of the knee joint is checked. In that regard, the surgeon or other medical personnel moves the knee through a variety of motions similar to the natural motions of the knee and monitors the knee for signs of problems. For example, in some instances the knee is monitor for limited or excessive the ranges of motion, abnormal sounds (e.g., clicking or grinding), non-smooth movements, implant rotation, implant translation, and/or other issues indicating a potential problem with using the associated implant. If a problem or potential problem is observed when checking the functionality of the knee, the first trial implant is removed an alternative trial implant is inserted and knee functionality is checked. In some instances, the subsequent trial implant will be one size up or down from the previous trial implant. Further, the time period for the trialing of the implant can range from a couple of minutes up to several weeks. This process repeats until a suitable trial implant is identified. In some instances, the trial implant process is substantially similar to the during-implantation matching process 204 discussed above.

Figure 25:
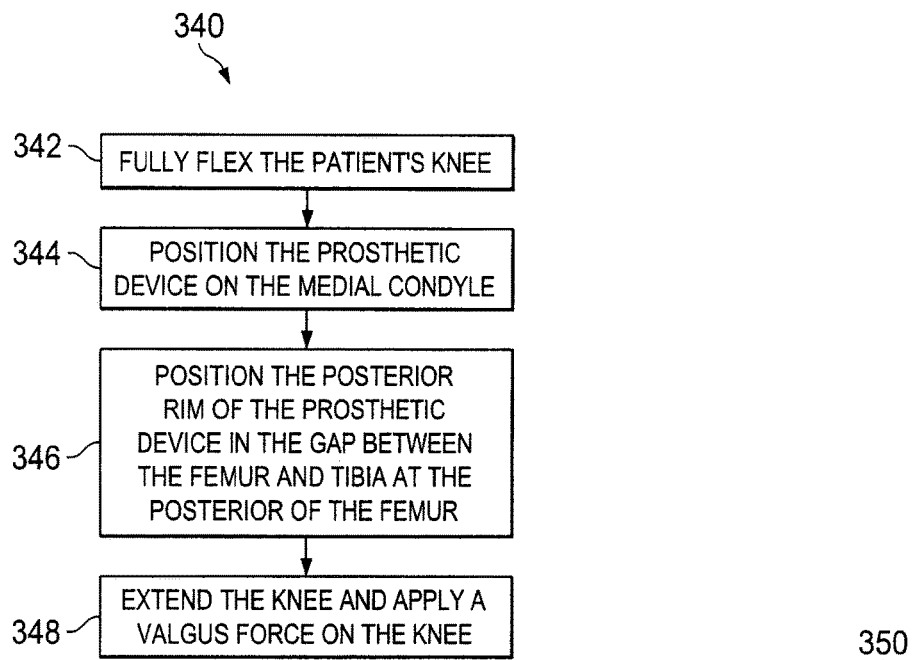
FIG. 25 is a block diagram of a method for implanting a prosthetic device into a patient's knee for use in the surgical protocol of FIG. 24 according to one aspect of the present disclosure.

After a suitable trial implant has been identified, the surgical protocol 320 continues at step 334 with the implantation of the implant or prosthetic device selected during the trialing process. Generally, the prosthetic device is implanted using any suitable implantation method for the associated prosthetic device. A couple of implantation methods will now be described. In some instances, the prosthetic devices of the present disclosure are suitable for implantation using the following methods. Referring to FIG. 25, shown therein is a block diagram of a method 340 of implanting a prosthetic device into a patient's knee according to one aspect of the present disclosure. In some instances, the method 340 is utilized as the implantation step 334 of the surgical protocol 320. The method 340 will be described with respect to a "floating" implant, i.e., an implant that does not penetrate the bone or mate with a device that penetrates bone. However, in other instances a similar method may be utilized with an implant that is fixedly secured to bone by penetrating bone or mating with a device that penetrates the bone.

The method 340 begins at step 342 where the patient's knee is fully flexed. That is, the patient's knee is put in full flexion. After the patient's knee has been fully flexed, the method 340 continues at step 344 where the prosthetic device is positioned onto the medial compartment of the tibia. As explained above, in one embodiment the bridge of the prosthetic device is folded slightly inward into a reduced size insertion configuration (see FIG. 9*a* for example) as it is passed into the knee joint. Once the bridge of the prosthetic device reaches the femoral notch, the bridge resiliently moves to its anchoring configuration (see FIG. 9*b* for example). The method 340 continues at step 346 where the posterior rim or edge of the prosthetic device is positioned within the gap between the femur and the tibia adjacent the posterior portion of the femur. With the prosthetic device positioned on the medial compartment and the posterior rim in the gap between the femur and tibia, the method 340 continues at step 348 where the knee is extended and a valgus force is applied to the knee. In some instances, the knee is extended to about a 30 degree flexion. In other instances, the knee is extended less or more. This secures the implant within the knee joint and engages the implant with both the medial compartment of the tibia and the femur. Subsequently, the shape of the implant and the compression forces applied across the implant keep the implant in place within the knee. In some instances, the prosthetic device 100 as described above is implanted using the method 340.

Figure 26:
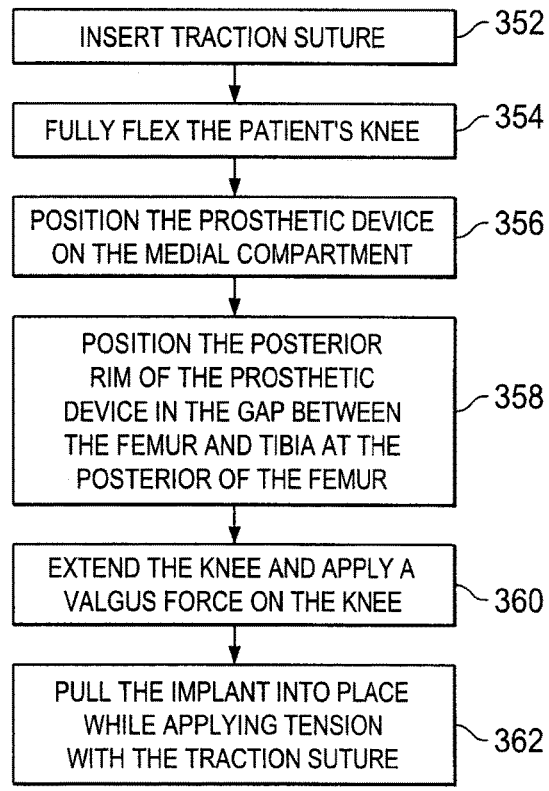
FIG. 26 is a block diagram of a method for implanting a prosthetic device into a patient's knee for use in the surgical protocol of FIG. 24 according to another aspect of the present disclosure.
Figure 27:
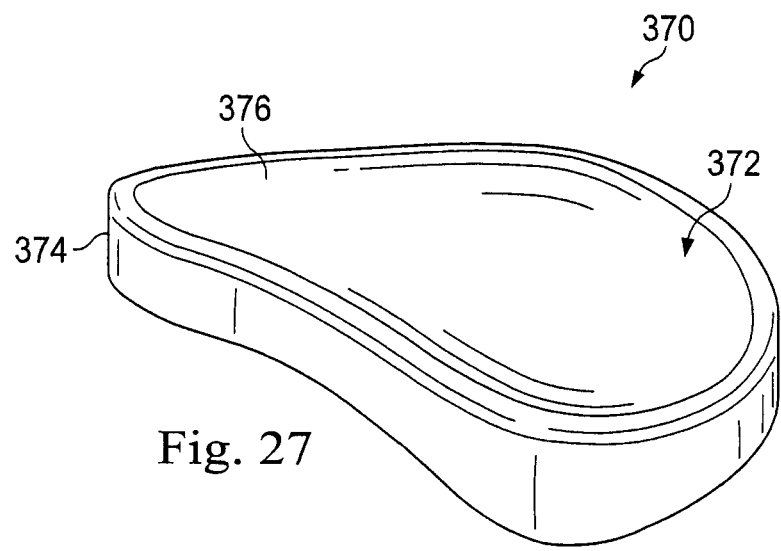
FIG. 27 is a diagrammatic perspective view of a prosthetic device according to one aspect of the present disclosure.

Referring now to FIG. 26, shown therein is a block diagram of a method 350 of implanting a prosthetic device into a patient's knee according to one aspect of the present disclosure. In some instances, the method 350 is utilized as the implantation step 334 of the surgical protocol 320. The method 350 will be described with respect to a "floating" implant, i.e., an implant that does not penetrate the bone or mate with a device that penetrates bone. However, in other instances a similar method may be utilized with an implant that is fixedly secured to bone by penetrating bone or mating with a device that penetrates the bone.

The method 350 begins at step 352 where a traction suture is inserted. In some instances the traction suture is inserted to the posterior-medial side of where the prosthetic device will be positioned and extends through the posterior-medial soft tissue structures enveloping the knee. In other embodiments, the traction suture is otherwise positioned adjacent and/or within the knee joint to assist in insertion of the prosthetic device into the medial cavity. It should be noted that in some instances the traction suture is inserted after a partial insertion of the prosthetic device into the knee joint. The method 350 continues at step 354 where the patient's knee is fully flexed. That is, the patient's knee is put in full flexion. After the patient's knee has been fully flexed, the method 350 continues at step 356 where the prosthetic device is positioned onto the medial condyle of the tibia. The method 350 continues at step 358 where the posterior rim or edge of the prosthetic device is positioned within the gap between the femur and the tibia adjacent the posterior portion of the femur. With the prosthetic device positioned on the medial condyle and the posterior rim in the gap between the femur and tibia, the method 350 continues at step 360 where the knee is extended and a valgus force is applied to the knee. The method 350 continues at step 362 where the implant is pulled into its final position while applying tension with the traction suture. In some instances, the traction suture helps facilitate positioning of the implant. In some embodiments, the traction suture is utilized to urge the implant into the medial cavity. In other embodiments, the traction suture is utilized to maintain an opening to the medial cavity to allow the implant to inserted therethrough. With the prosthetic device secured within the knee joint, the shape of the implant and the compression forces applied across the implant during loading of the knee prevent the implant from slipping out of place.

Referring again to FIG. 24, the method 320 continues at step 336 with checking the knee motion with the prosthetic device implanted. In some embodiments, step 336 is substantially similar to step 332 where the trial implants are evaluated. Accordingly, in some embodiments step 336 comprises confirming the actual implant performs as suggested by the monitoring of the trial implant at step 332. If, for some reason, the knee functionality with the prosthetic device implanted is impaired, the prosthetic device may be adjusted, replaced with an alternative prosthetic device, or otherwise modified to correct the problem. After the knee motion has been checked and confirmed to be acceptable, the method 320 concludes at step 338 with the suturing and bandaging of the knee.

Though not described in the above methods, it is fully contemplated that in some instances, the femoral condyle and/or other aspects of the knee joint may be surgically prepared to permit near-normal knee joint flexion after implantation. Further, the tibial plateau and/or other aspects of the knee joint may be surgically prepared to fixedly engage the implanted prosthetic device. Other modifications of the above methods will be apparent to those skilled in the art without departing from scope of the present disclosure.

A variety of materials are suitable for use in making the prosthetic devices of the present disclosure. Medical grade polyurethane based materials especially suitable for use in the embodiments described include, but are not limited to the following:

Bionate®, manufactured by Polymer Technology Group ("PTG"), a polycarbonate-urethane is among the most extensively tested biomaterials ever developed. Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability. Bionate® polycarbonate-urethane is a thermoplastic elastomer formed as the reaction product of a hydroxyl terminated polycarbonate, an aromatic diisocyanate, and a low molecular weight glycol used as a chain extender. The results of extensive testing encompassing Histology, Carcinogenicity, Biostability, and Tripartite Biocompatibility Guidance for Medical Devices verifies the cost effective material's biocompatibility.

Another group of suitable materials are copolymers of silicone with polyurethanes as exemplified by PurSil™, a Silicone Polyether Urethane and CarboSil™, a Silicone Polycarbonate Urethane. Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted. In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have an excellent flex life, tensile strength exceeding 5000 psi, and ultimate elongations greater than 700 percent. These materials are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, in polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo. Polymer Technology Group synthesized silicone-polyurethane copolymers by combining two previously reported methods: copolymerization of silicone (PSX) together with organic (non-silicone) soft segments into the polymer backbone, and the use of surface-modifying end groups to terminate the copolymer chains.

Other applicable materials include PurSil™ silicone-polyether-urethane and CarboSil™ silicone-polycarbonate-urethane which are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminated polycarbonate (CarboSil). The hard segment consists of an aromatic diisocyanate, MDI, with low molecular weight glycol chain extender. The copolymer chains are then terminated with silicone (or other) Surface-Modifying End Groups. Aliphatic (AL) versions of these materials, with a hard segment synthesized from an aliphatic diisocyanate, are also available.

Many of these silicone urethanes demonstrate desirable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Properties). These properties make these materials very attractive as high-performance substitutes for conventional cross-linked silicone rubber. In both the PTMO and PC families, some polymers have tensile strengths three to five times higher than conventional silicone biomaterials.

Further examples of suitable materials include Surface Modifying End Groups (SMEs) which are surface-active oligomers covalently bonded to the base polymer during synthesis. SMEs—which include silicone (S), sulfonate (SO), fluorocarbon (F), polyethylene oxide (P), and hydrocarbon (H) groups—control surface chemistry without compromising the bulk properties of the polymer. The result is that key surface properties, such as thromboresistance, biostability, and abrasion resistance, are permanently enhanced without additional post-fabrication treatments or topical coatings. This technology is applied to a wide range of PTG's polymers.

SMEs provide a series of base polymers that can achieve a desired surface chemistry without the use of additives. Polyurethanes prepared according to PTG's development process couple endgroups to the backbone polymer during synthesis via a terminal isocyanate group, not a hard segment. The added mobility of endgroups relative to the backbone facilitates the formation of uniform overlayers by the surface-active end blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymers amphipathic characteristics in which the hydrophobic versus hydrophilic balance may be easily controlled.

Other suitable materials, manufactured by CARDIO-TECH CTE, include ChronoFlex® and Hydrothane™.

The ChronoFlex®, polycarbonate aromatic polyurethanes, family of medical-grade segmented biodurable polyurethane elastomers have been specifically developed by CardioTech International to overcome the in vivo formation of stress-induced microfissures.

HydroThane™, hydrophilic thermoplastic polyurethanes, is a family of super-absorbent, thermoplastic, polyurethane hydrogels ranging in water content from 5 to 25% by weight. HydroThane™ is offered as a clear resin in durometer hardness of 80A and 93 Shore A. The outstanding characteristic of this family of materials is the ability to rapidly absorb water, high tensile strength, and high elongation. The result is a polymer having some lubricious characteristics, as well as being inherently bacterial resistant due to their exceptionally high water content at the surface.

HydroThane™ hydrophilic polyurethane resins are thermoplastic hydrogels, and can be extruded or molded by conventional means. Traditional hydrogels on the other hand are thermosets and difficult to process.

Additional suitable materials manufactured by THERMEDICS include Tecothante® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane). Tecothane® is a family of aromatic, polyether-based TPU's available over a wide range of durometers, colors, and radiopacifiers. One can expect Tecothane resins to exhibit improved solvent resistance and biostability when compared with Tecoflex resins of equal durometers. Carbothane® is a family of aliphatic, polycarbonate-based TPU's available over a wide range of durometers, colors and radiopacifiers. This type of TPU has been reported to exhibit excellent oxidative stability, a property which may equate to excellent long-term biostability. This family, like Tecoflex, is easy to process and does not yellow upon aging. Tecophilic® is a family of aliphatic, polyether-based TPU's which have been specially formulated to absorb equilibrium water contents of up to 150% of the weight of dry resin.

Polyurethanes are designated aromatic or aliphatic on the basis of the chemical nature of the diisocyanate component in the formulation. Tecoflex, Tecophilic and Carbothane resins are manufactured using the aliphatic compound, hydrogenated methylene diisocyanate (HMDI). Tecothane and Tecoplast resins use the aromatic compound methylene diisocyanate (MDI). Tecoflex® is a family of aliphatic, polyether-based TPU's. These resins are easy to process and do not yellow upon aging. Solution grade versions are candidates to replace latex. Some formulations are formulated using polytetramethylene ether glycol (PTMEG) and 1,4 butanediol chain extender. Carbothane is specifically formulated with a polycarbonate diol (PCDO). These materials represent the major chemical composition differences among the various families. Aromatic and aliphatic polyurethanes share similar properties that make them outstanding materials for use in medical devices. In general, there is not much difference between medical grade aliphatic and aromatic polyurethanes with regard to the following chemical, mechanical and biological properties: high tensile strength (4,000 to 10,000 psi); high ultimate elongation (250 to 700%); wide range durometer (72 Shore A to 84 Shore D); good biocompatibility; high abrasion resistance; good hydrolytic stability; can be sterilized with ethylene oxide and gamma irradiation; retention of elastomeric properties at low temperature; good melt processing characteristics for extrusion, injection molding, etc.

With such an array of desirable features, it is no wonder that both aliphatic and aromatic polyurethanes have become increasingly the material of choice in the design of medical grade components. There are, however, distinct differences between these two families of polyurethane that could dictate the selection of one over the other for a particular application:

In their natural states, both aromatic and aliphatic polyurethanes are clear to very light yellow in color. Aromatics, however, can turn dark yellow to amber as a result of melt processing or sterilization, or even with age. Although the primary objection to the discoloration of aromatic clear tubing or injection molded parts is aesthetic, the yellowing that is caused by the formation of a chromophore in the NMI portion of the polymer does not appear to affect other physical properties of the material. Radiopaque grades of Tecothane also exhibit some discoloration during melt processing or sterilization. However, both standard and custom compounded radiopaque grades of Tecothane have been specifically formulated to minimize this discoloration.

Aromatic polyurethanes exhibit better resistance to organic solvents and oils than do aliphatics—especially as compared with low durometer (80 to 85 Shore A) aliphatic, where prolonged contact can lead to swelling of the polymer and short-term contact can lead to surface tackiness. While these effects become less noticeable at higher durometers, aromatics exhibit little or no sensitivity upon exposure to the common organic solvents used in the health care industry.

Both aliphatic and aromatic poly-ether based polyurethanes soften considerably within minutes of insertion in the body. Many device manufacturers promote this feature of the urethane products because of patient comfort advantage as well as the reduced risk of vascular trauma. However, this softening effect is less pronounced with aromatic resins than with aliphatic resins.

Tecothane, Tecoplast and Carbothane melt at temperatures considerably higher than Tecoflex and Tecophilic. Therefore, processing by either extrusion of injection molding puts more heat history into products manufactured from Tecothane, Tecoplast and Carbothane. For example, Tecoflex EG-80A and EG-60D resins mold at nozzle temperatures of approximately 310 degrees F. and 340 degrees F. respectively while Tecothane and Carbothane products of equivalent durometers mold at nozzle temperatures in the range of 380 degrees F. and 435 degrees F.

Additional materials of interest include Tecogel, a new member to the Tecophilic family, a hydrogel that can be formulated to absorb equilibrium water contents between 500% to 2000% of the weight of dry resin, and Tecoplast®, a family of aromatic, polyether-based TPU's formulated to produce rugged injection molded components exhibiting high durometers and heat deflection temperatures.

Additional potentially suitable materials include four families of polyurethanes, named Elast-Eon™, which are available from AorTech Biomaterials.

Elast-Eon™1, a Polyhexamethylene oxide (PFMO), aromatic polyurethane, is an improvement on conventional polyurethane in that it has a reduced number of the susceptible chemical groups. Elast-Eon™2, a Siloxane based macrodiol, aromatic polyurethane, incorporates siloxane unto the soft segment. Elast-Eon™3, a Siloxane based macrodiol, modified hard segment, aromatic polyurethane, is a variation of Elast-Eon™2 with further enhanced flexibility due to incorporation of siloxane into the hard segment. Elast-Eon™4 is a modified aromatic hard segment polyurethane.

Bayer Corporation also produces candidate materials. Texin 4210 and Texin 4215 are thermoplastic polyurethane/polycarbonate blends for injection molding and extrusion. Texin 5250, 5286 and 5290 are aromatic polyether-based medical grade materials with Shore D hardness of approximately 50, 86, and 90 respectively for injection molding and extrusion.

Manufacturing Procedures

The prosthetic devices of the present disclosure may be manufactured in various sizes, so that typical applications can be satisfied by a "stock" unit. Accordingly, a surgeon could, during an implantation procedure, select a correctly sized device from the selection of stock units. Alternatively, in another embodiment, a replacement meniscus is custom manufactured for a particular patient utilizing characteristics determined by medical imaging techniques, such as MRI, coupled with computer aided manufacturing (CAM) techniques.

In some embodiments, the prosthetic device is a melt mold composite implant composed of two biocompatible materials: PTG Bionate® Polycarbonate-Urethane (PCU), 80 Shore A, matrix material and ultra high molecular weight polyethylene (UHMWPE) reinforcement material. In some particular embodiments, a prosthetic device formed of PCU and reinforced circumferentially with DSM Dyneema® fibers results in a desirable distribution of loads on the underlying articulation surfaces of the prosthetic device. Accordingly, referring generally to FIGS. 27-35 aspects and methods of manufacturing such a device will be described.

Figure 29:
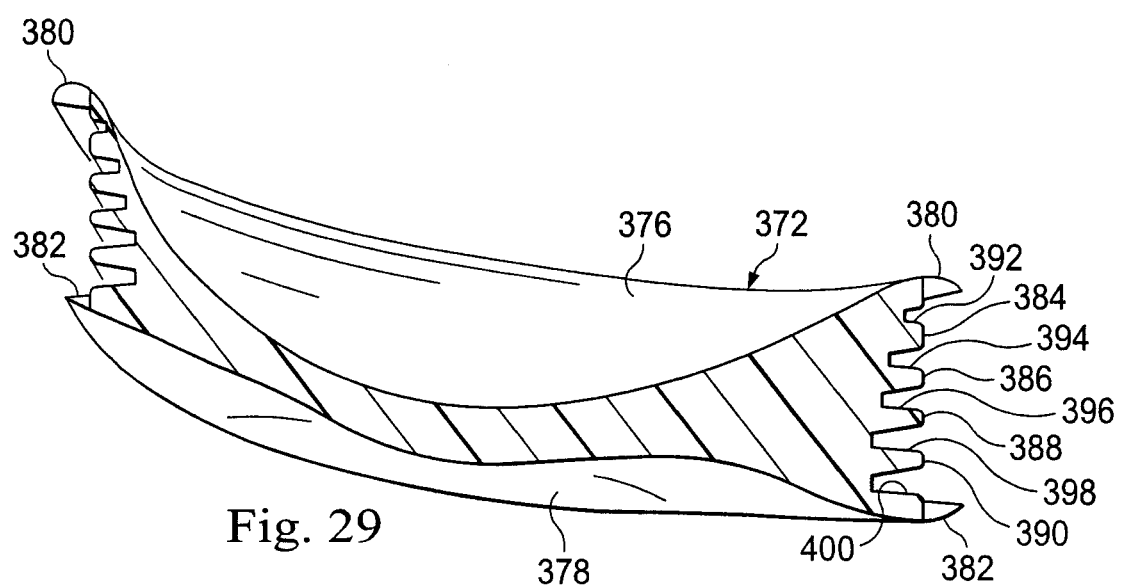
FIG. 29 is a diagrammatic perspective view of a core of the prosthetic device of FIG. 27 according to one aspect of the present disclosure.

Referring more specifically to FIGS. 27, 28, 29, and 31, shown therein is a prosthetic device 370 according to one aspect of the present disclosure. Generally, the prosthetic device 370 includes a core 372 surrounded by an outer portion 374. The prosthetic device 370 includes an upper articulation surface 376 and an opposing lower articulation surface 378 (FIG. 29). The upper articulation surface 376 is configured to engage the femur while the lower articulation surface 378 is configured to engage the tibia. In some embodiments, the prosthetic device 370 is formed via an injection molding process that substantially limits the defects, imperfections, and/or process residue in and on the articulation surfaces. In that regard, the articulation surfaces may obtain a smoothness substantially similar to that of the surfaces of the mold in which they are formed. In some instances, the mold surfaces are mirror polished to an optical polish between about 0.05 Ra and 0.4 Ra.

Figure 28:
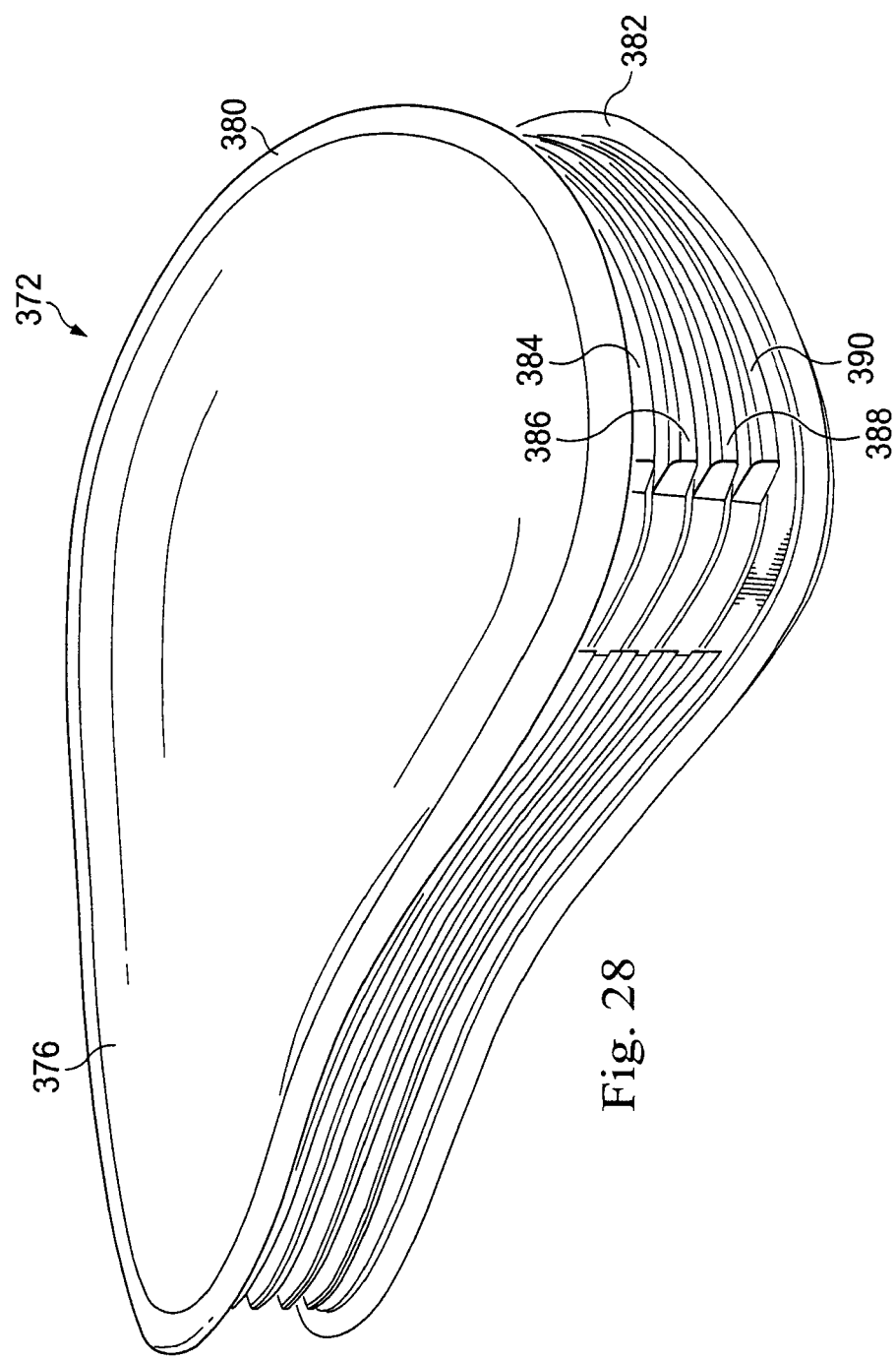
FIG. 28 is a diagrammatic perspective view of a core of a prosthetic device according to one aspect of the present disclosure.

The prosthetic device 370 is imbedded with fibers (not shown). In some instances, the fibers are positioned circumferentially around the prosthetic device 370 between the core 372 and the outer portion 374. In that regard, the core 372 includes features to facilitate positioning of the fibers within the prosthetic device 370 in some embodiments. For example, referring more specifically to FIG. 28, shown therein is a diagrammatic perspective view of the core 372 according to one aspect of the present disclosure. As shown, the core 372 includes an upper rim 380 and a lower rim 382 defining an outer boundary of the core. Between the upper and lower rims 380, 382 the core 372 includes a series of alternating projections and recesses. In the current embodiment, the core includes projections 384, 386, 388, and 390 between the upper rim 380 and the lower rim 382. Referring to FIG. 29, between the rims 380, 382 and the projections the core 372 includes recesses 392, 394, 396, 398, and 400. In some embodiments, the recesses 392, 394, 396, 398, and 400 are sized and shaped to receive the fibers to be imbedded within the device 370. In some instances, the projections 384, 386, 388, 390 and the recesses 392, 394, 396, 398, 400 are configured such that the fibers may be wound around the core 372.

In the present embodiment, the recesses 392, 394, 396, 398, and 400 increase in size along the height of the core 372 from the upper rim 380 to the lower rim 382. Accordingly, the recess 392 adjacent the upper rim 380 and projection 384 is the smallest of the recesses, while the recess 400 adjacent the lower rim 382 and projection 390 is the largest of the recesses. Thus, in the current embodiment the lower portion of the prosthetic device 370 as viewed in FIG. 29 is configured to receive a greater number of fibers than the upper portion of the device. Further, as shown, each of the recesses 392, 394, 396, 398, and 400 are tapered such that the recess is wider adjacent the outer portion of the recess than the inner portion of the recess. In some instances, this is a result of injection molding the core 372 with a mold/insert having a corresponding tapered or angled shape. The tapering or angling the mold/inserts in this manner to create the tapered or angled recesses allows the mold/inserts to be separated from the core 372 after the injection molding process easier and without causing damage to the core.

Generally, the shape and size and of the projections and recesses of the core 372 are tailored or selected to achieve the desired fiber distribution through the device. Accordingly, in some instances all of the projections and recesses are substantially the same size. In other instances, the projections, recesses, or other aspects of the prosthetic device associated with the distribution of the imbedded fibers vary along the height, circumference, length, width, or other aspect of the prosthetic device to accommodate a desired fiber distribution. In that regard, in some instances, the projections and recesses are substantially annular extending completely around the core 372. In other instances, such as the embodiment illustrated in FIG. 28, the projections and recesses comprise one or more discrete sections around the core 372.

Figure 30:
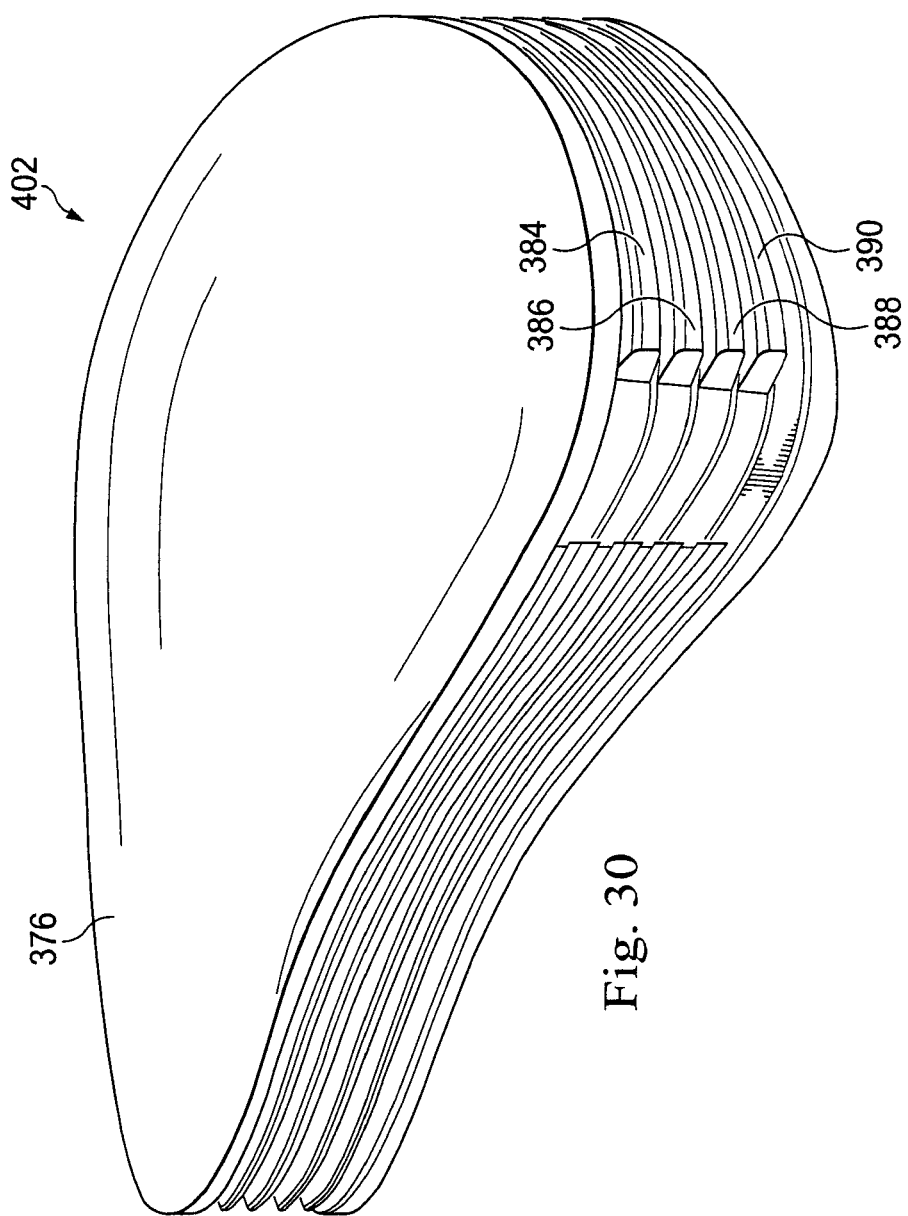
FIG. 30 is a diagrammatic cross-sectional view of the prosthetic device core of FIG. 29.

In some instances, the upper and lower rims 380, 382 of the core 372 are configured to mate with the outer portion 374 of the prosthetic device 370 such that the outer portion is substantially positioned between the upper and lower rims. In that regard, the upper and lower rims 380, 382 may comprise part of the upper and lower articulation surfaces 376, 378, respectively, such that the outer portion 374 may be injection molded or otherwise attached to the core 372 without adversely affecting the articulation surfaces of the prosthetic device 370. In some instances, however, the core 372 does not include the upper and lower rims 380, 382. For example, referring to FIG. 30 shown therein is a core 402 according to an alternative embodiment of the present disclosure that does not include upper and lower rims. The core 402 is otherwise substantially similar to the core 372 in other respects. In some instances, the outer portion 374 of the prosthetic device 370 comprises an outer area or boundary of the upper and lower articulating surfaces of the prosthetic device. For example, in some instances the outer portion 374 is molded around the core 402 such that the outer portion defines at least a portion of the upper and lower articulating surfaces of the prosthetic device. In one such embodiment, at least the upper and lower surfaces of the outer portion 374 have a smoothness substantially similar to the upper and lower articulating surfaces 376, 378 of the core.

As noted, in other instances, the outer portion 374 is positioned substantially between the upper and lower rims 380, 382 of the core 372. Referring more specifically to FIG. 31, the outer portion 374 comprises an inner surface 404, and outer surface 406, an upper surface 408, and a lower surface 410. While the inner surface 404 is shown as being substantially smooth, it is understood that in some embodiments the outer portion 374 is injection molded around the core 372 and/or the fibers surrounding the core. In such embodiments, the inner surface 404 will substantially match the contours of the core and fibers adjacent thereto. In other embodiments, however, the outer portion 374 comprises a substantially smooth inner surface 404 as shown. Where the outer portion 374 is positioned substantially between the upper and lower rims 380, 382 the upper and lower surfaces 408, 410 interface with the rims. In that regard, in some instances, the engagement surfaces of the upper and lower rims 380, 382 include features to facilitate engagement between the outer portion 374 and the core 372. For example, the engagement surfaces of the upper and lower rims 380, 382 may be roughened, textured, knurled, include projections and/or recesses, or otherwise be shaped or treated to enhance engagement between the outer portion 374 and the core 372.

In some embodiments, the fibers of the prosthetic device 370 are fully imbedded inside the hosting material of the core 372 and/or the outer portion 374 to prevent contact between the fibers and articulation surfaces of the device. In this manner the fibers are prevented from contacting the host tissue of the patient as well. In some embodiments, the fibers are formed of UHMWPE while the core 372 and/or outer portion 374 are formed of a PCU. In such embodiments, the injection molding process is performed in a manner that does not affect the form, mechanical properties, or stability of the UHMWPE fibers. In that regard, generally the UHMWPE has a lower melting temperature than the PCU such that standard injection molding processes that would inject PCU around the UMWPE fibers will adversely affect the properties of the UHMWPE fibers. Accordingly, in some instances the prosthetic device 370 is manufactured utilizing methods of the present disclosure that preserve the desired material properties of the UHMWPE fibers even when utilized with PCU.

In some embodiments, the fibers are configured to distribute the load across the prosthetic device 370 in a manner that mimics a natural meniscus. In that regard, the amount of fibers, the type of fibers, distribution of the fibers, and/or the location of the fibers is altered in some embodiments to achieve a desired load distribution. Further, these attributes of the fiber may vary within a single implant depending on the position within the implant. For example, in some instances the number or density of fibers varies along the height of the prosthetic device. In some instances, the fiber characteristics are determined at least partially based on the patient receiving the prosthetic device 370. For example, factors such as the size of the patient's knee anatomy, the patient's weight, the patient's anticipated activity level, and or other aspects of the patient are taken into consideration when determining the characteristics of the fibers imbedded in the prosthetic device 370. In some instances, a fiber incorporation ratio (FIR) is taken into consideration. Generally, the fiber incorporation ratio is representative of the amount or percentage of fibers within the prosthetic device 370 as compared to the matrix material or base material. In some embodiments, the fiber incorporation ratio is measured as the area of the fibers divided by the area of the prosthetic device as view in a cross-section of the device, or $$FIR = \frac{Area_{FiberCS}}{Area_{DeviceCS}}.$$

Referring to FIG. 32, shown there is a chart setting forth fiber incorporation ratios for prosthetic devices based on patient weight and activity levels according to one aspect of the present disclosure. As illustrated, in this embodiment the fiber incorporation ratio is determined based on the patient's weight and activity level, which are grouped into ranges. Specifically, the patient's weight is grouped into three categories: less than 60 Kg, between 60 Kg and 110 Kg, and greater than 110 Kg. In other embodiments, the patient's weight is grouped into a greater number of categories or the patient's specific weight is utilized. The patient's activity level is also grouped into three categories: low activity, moderate activity, and high activity. Again, in other embodiments the patient's activity level is grouped into a greater number of categories and/or characterized based on types of activities. In other instances, other factors are taken into consideration in determining the fiber incorporation. As shown in FIG. 32, generally the greater the patient's weight and activity level, the greater the fiber incorporation ratio. Generally, in accordance with FIG. 32 the fiber incorporation ratio ranges from about 0.1% to about 1.2%. In other embodiments, however, the fiber incorporation ratio ranges from about 0.0% (i.e., no fibers) to about 50%.

Referring to FIGS. 33 and 34, shown therein are prosthetic devices 430 and 440 having different fiber incorporation ratios according to the present disclosure. The prosthetic device 430 of FIG. 33 includes an upper articulation surface 432, a lower articulation surface 434, and an outer portion 436 reinforced with fibers 438. The prosthetic device 430 comprises a relatively low fiber incorporation ratio. The fibers 438 are distributed equally along the height of the prosthetic device 430 and adjacent the outer boundary of the device. The prosthetic device 440 of FIG. 34 also includes an upper articulation surface 442, a lower articulation surface 444, and an outer portion 446 reinforced with fibers 447. However, the fibers 447 of the prosthetic device 440 are not distributed equally along the height of the device. As shown, in the prosthetic device 440 the fibers 447 are generally aligned in rows 448, 450, 452, and 454 of increasing fiber density from the upper portion of the device towards the lower portion of the device. In some aspects, the prosthetic device 440 is representative of a device that utilizes the core 372 discussed above having varying sized recesses for receiving the fibers. In that regard, the rows 448, 450, 452, and 454 of varying fiber density correspond to the recesses of the core having varying sizes for receiving the fibers.

Referring now to FIG. 35, shown therein is a block diagram of a method 460 for manufacturing a prosthetic device according to one aspect of the present disclosure. Generally, the method 460 comprises three steps: a core injection step 462, a fiber winding step 464, and an outer portion injection step 466. The method 460 begins at step 462 with the injection molding of the core of the prosthetic device. In some instances, the core is molded to be substantially similar to the cores 372 or 402 described above. Accordingly, in such embodiments the mold into which the material is injected is shaped as the negative of the core 372 or core 402. In some instances, to avoid over-lapping of the PCU in the outer portion injection process and to ensure that the contact surfaces of the implant remain smooth and free of defects, the upper and lower rims of the core are molded to allow the outer portion of the prosthetic device to be subsequently injected between the rims without affecting the articulation surfaces of the device.

After molding of the core at step 462, the method 460 continues at step 464 with the winding of fiber around the core. In some embodiments, the core is allowed to completely set up prior to winding the fibers around the core. In other instances, the core is not completely set up prior to the winding such that at least a first layer of the fibers is at least partially imbedded within the core. In some embodiments, the winding process 464 is performed by a winding machine that controls the amount of fibers in each tunnel or recess of the core and maintains the tension of the fibers during the winding process. As discussed above, the tunnels of core are sized to allow incorporation of different amounts of fibers in some embodiments. Accordingly, in some instances between 1 and 20 fibers are placed in each tunnel depending on the location of the tunnel along the implant height.

During the winding process 464 the fibers will be tensioned with a force between about 5 N and about 78 N. In some instances, the tension on the fibers is selected so that the resultant prosthetic device is pretensioned such that the prosthetic device stretches upon implantation and loading. In some instances, the pretensioning results in the prosthetic device having a reduced size relative to the natural meniscus in the pretensioned state. In some embodiments, the tension on the fiber is determined based on the chart of FIG. 36 setting forth tensioning forces for various fibers based on the property of the fibers according to one aspect of the present disclosure. In some instances, the fiber is wound at approximately 10% of the fiber's maximum tension. For example, if the fibers maximum tension force is approximately 50 N, then in some instances the fiber is wound around the core of the prosthetic device with a force of approximately 5 N.

After the fibers have been wound around the core, the method 460 continues at step 466 with the injection molding of the outer portion of the prosthetic device. In some instances, prior to the outer portion injection 466, the core mold will be warmed to approximately 100° C. to improve the adhesion between the core and the outer surface portion. However, based on manufacturer instruction, long exposure to temperatures higher than 150° C. will cause melting of UHMWPE fibers. A short exposure to temperature higher than 150° C. (thermal shock condition), however, will not affect the structural or mechanical properties of the UHMWPE fibers. Accordingly, in some instances the outer portion is injected at a temperature above the melting point of the UHMWPE fibers. In one specific embodiment, a polycarbonate polyethylene is injected at a temperature of approximately 160° C. Accordingly, in embodiments where UHMWPE fibers are utilized, one or more of the following steps are utilized to minimize the time the fibers are exposed to the elevated temperature to prevent melting of the fibers and/or adverse material changes to the fibers. In some instances, immediately after the outer surface injection, the mold is cooled to ambient room temperature (approximately 25° C.) by circulating cold fluid through cooling tunnels within the mold used in forming the prosthetic device. Further, in some instances, the amount of the material injected into the mold for the outer portion is kept to a minimum. The smaller mass of injected material cools faster reducing the exposure time to the increased temperatures.

In some embodiments, the two-phase molding process (steps 462 and 466) utilizes a single modular mold structure composed of several parts. For example, in some instances the mold comprises an outer structure shaped to correspond to the overall shape of the prosthetic device and includes at least one removable insert shaped for molding the core of the prosthetic device. In that regard, the mold is modified by removing the inserts between the two injection phases 462 and 466. The removal of the inserts allows the winding of fibers around the core in some instances. Generally, removal of the inserts after the core injection 462 does not require the removal or destruction of the previously injected material forming the core. Rather, as discussed above the tunnels or recesses along the perimeter of the core are shaped to allow smooth release of the inserts of the mold that shape these tunnels. For example, in some embodiments, the mold inserts are tapered to facilitate removal. In some instances, the mold inserts are polished or otherwise have smooth surfaces to limit the friction between the injected core and the inserts. In some embodiments, the mold is made of aluminum, steel, other metals, and/or combinations thereof. In situations where aluminum and/or aluminum steel are utilized, the surfaces that come into contact with the injected material are coated with hard anodize. In some instances, a layer of approximately 10 µm of hard anodize is utilized. In other instances, a thicker or thinner layer of hard anodize is utilized.

In some embodiments, the prosthetic devices are formed of a cartilage replacement material having structural and material properties simulating the functionality of a natural meniscus. Generally, the material provides a pliable articulating surface equivalent to the various load bearing forms of cartilaginous tissues of the body, such as hyaline (articular) cartilage and fibro-cartilage (e.g. intervertebral discs, knee meniscus, etc.). The material provides shock absorption and reduction in the impact intensity exerted on the adjacent bones and/or the implant itself. In some instances, the shock absorption function reduces patient pain, reduces wear on the device, and/or provides greater mobility to the patient. The material is resiliently deformable. Specifically, the material deforms under the natural stresses applied by the patient's body such that material stresses of the prosthetic device are handled in a manner similar to that of the natural cartilage to achieve pressure distributions within the material and on the articulating surfaces similar to natural, healthy cartilage.

In one embodiment, the material is a composite material composed of a pliable biocompatible matrix material imbedded with fibers or other reinforcement material. The specific composite structure of the material is based, in some instances, on the structural characteristics of natural cartilage, which consists of a cartilage matrix imbedded with a highly orientated collagen fiber network or collagen fibrils. Similar to natural cartilage, the material is able to withstand high impact forces yet maintain its form due to its reinforced resilient composite structure. In that regard, a synergism between the matrix material and the fiber material results in material properties unavailable from the each of the materials individually. Specifically, the pliable matrix material provides a damping or cushioning effect and distributes pressure by permitting local material flow or deformation. The reinforcement material, on the other hand, maintains and stabilizes the overall design shape of the prosthetic device by restraining or limiting the flow of the matrix material. In that regard, the reinforcement material or fiber material bears a high portion of the stresses that act on the prosthetic device. In some instances, compressive loads exerted on the prosthetic device are transformed into tensile loading on the reinforcement or fiber materials due to the shape of the prosthetic device and the orientation of the fibers therein. In that regard, the prosthetic device 100 discussed above functions in this manner in some instances. That is, compression loading of the prosthetic device 100 is converted into tensile loading on the imbedded fiber 124 due to the deformation or stretching of the prosthetic device. These materials have been shown to produce load distributions under compression similar to natural cartilaginous tissue.

In some embodiments, the resilient matrix material comprises a biocompatible polymer. In some instances, the polymer is a polycarbonate polyurethane. In one specific embodiment, the matrix material is PTG Bionate® Polycarbonate-Urethane (PCU), 80 Shore A. The high modulus reinforcement material utilized in the application may be any one of the following: Ultra High Molecular Weight Polyethylene (UHMWPE) fiber, for example DSM Dyneema® Purity; Para-aramid synthetic fiber, for example DuPont™ Kevlar, Kevlar29, Kevlar49; carbon; stainless-steel; titanium; nickel-titanium (Nitinol); and/or other suitable reinforcement materials. In that regard, the fibers may be employed in a monofilament or multifilament form as a single strand or a multiple fiber twine, in a diameter range of 0 to 1 mm.

A few specific embodiments of the cartilage replacement material will now be described. These embodiments are understood to be exemplary and do not limit the various ways in which reinforcement material may be imbedded or otherwise distributed within a matrix material to simulate the properties of natural cartilage in accordance with the present disclosure. Generally, the reinforcement material can be imbedded in the matrix material in either a fiber form (straight, wound, or otherwise), in a complex mesh form, and/or any combination of thereof depending on the desired functionality and geometry of the application. In some instances, the fiber distribution varies through different portions of the matrix material. In that regard, in some embodiments the fiber distribution is varied such that the mechanical properties of the material divert high stresses from prone areas.

Overall, the fiber incorporation ratio of the material may vary between about 0 percent and about 50 percent, when measured as the fiber cross section area relative to the total material cross section area. In some instances, the fiber incorporation ratio is varied through the material to obtain a desired functionality and/or material properties. For example, the amount of fibers incorporated into the material may vary according to position (i.e. the amount of fibers incorporated in different material depths and locations is varied) based on the intended application of material. Generally, higher contact stress areas are associated with employing of higher a number of fibers. Accordingly, in some instances fibers are concentrated in the high contact stress areas of the material or prosthetic device. The specific number of fibers utilized depends on such factors as patient activity level, patient body weight, the matrix material, the fiber material, implant shape, desired functionality, and/or other factors. In some instances, the distribution of fibers and/or the fiber incorporation ratio are determined by a computational finite-element analysis.

Figure 37:
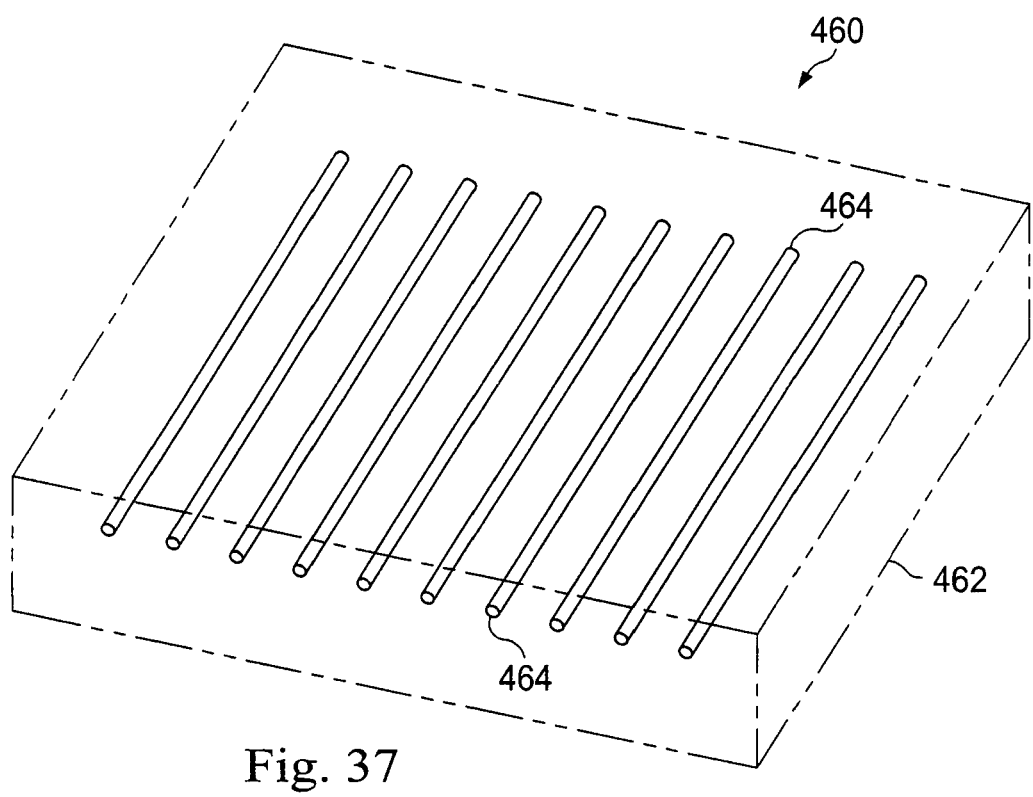
FIG. 37 is a diagrammatic perspective view of a material having a linear fiber configuration according to one aspect of the present disclosure.

Referring more specifically to FIG. 37, shown therein is a diagrammatic perspective view of a representative material 460 having a linear fiber configuration according to one aspect of the present disclosure. In that regard, the material 460 includes a matrix material 462 imbedded with a plurality of fibers 464. As shown, the fibers 464 extend substantially parallel to one another along a length of the material. In some instances, the fibers 464 are aligned such that all of the fibers are positioned substantially within the same plane within the matrix material. In other embodiments, the fibers are aligned in multiple planes within the matrix material. In yet other embodiments, the fibers are distributed throughout the matrix material but all extend linearly in substantially the same direction. Generally, the fibers 464 may be distributed through the matrix material 462 in any manner, orientation, or combination such that the fibers 464 extend linearly and substantially parallel to one another.

Figure 38:
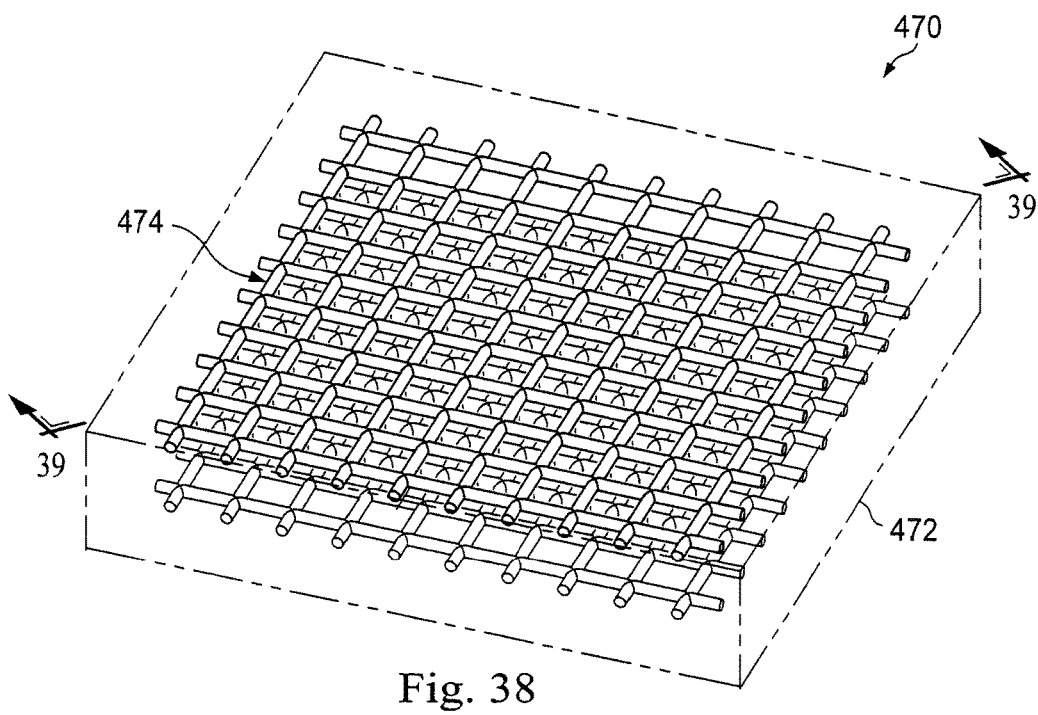
FIG. 38 is a diagrammatic perspective view of a material having a fiber mesh configuration according to one aspect of the present disclosure.
Figure 39:
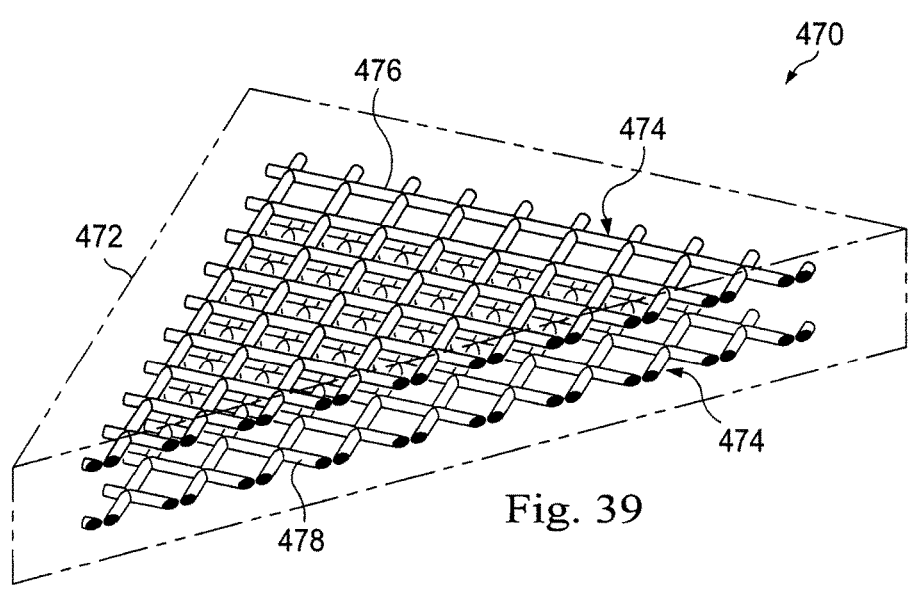
FIG. 39 is a diagrammatic partial cross-sectional view of the material having a fiber mesh configuration of FIG. 38 taken along section line 39-39.

Referring more specifically to FIGS. 38 and 39, shown therein is a representative material 470 having a fiber mesh configuration according to one aspect of the present disclosure. Specifically, FIG. 38 is a diagrammatic perspective view of the material 470 and FIG. 39 is a partial cross-sectional view of the material 470 taken along section line 39-39 of FIG. 38. The material 470 includes a matrix material 472 imbedded with a plurality of fibers or fiber mesh 474. As shown in FIG. 39, in the present embodiment the fibers 474 include an upper fiber mesh portion 476 and a lower fiber mesh portion 478. As shown, each of the fiber mesh portions 476, 478 comprise interlocking, interweaved, and/or overlying fibers 474 organized in a grid pattern. In the present embodiments, the fibers interface at substantially perpendicular angles to define the grid pattern. That is, a first grouping of fibers extend substantially parallel to one another along a first axis of the material and a second grouping of fibers extend substantially parallel to a second axis of the material substantially perpendicular to the first axis to define grid pattern of the fiber mesh. In other embodiments, the fiber mesh may comprise alternative grid patterns, angles, and/or orientations. In the present embodiment, the upper and lower fiber mesh portions 476, 478 are substantially planar and extend substantially parallel to one another through the material 470. In some instances, the fiber mesh portions 476, 478 extend at non-parallel angles with respect to one another. In some embodiments, the material 470 includes a greater or fewer number of fiber mesh portions. In some instances, the fiber mesh portions are not substantially planar. Generally, the fiber mesh portions may be distributed through the matrix material 472 in any manner, orientation, or combination as desired.

Figure 40:
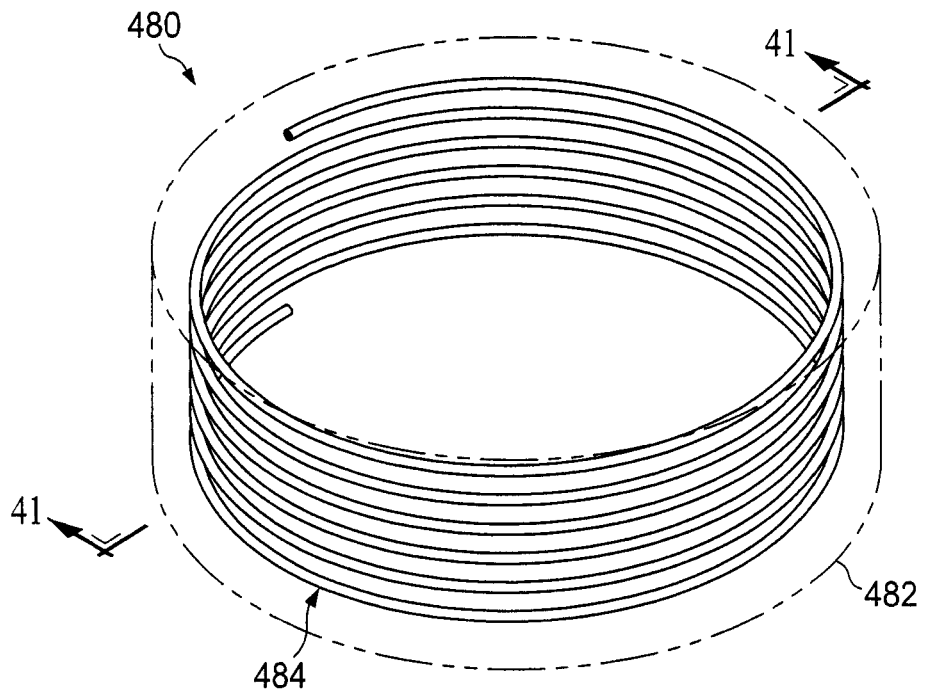
FIG. 40 is a diagrammatic perspective view of a material having a winded fiber configuration according to one aspect of the present disclosure.
Figure 41:
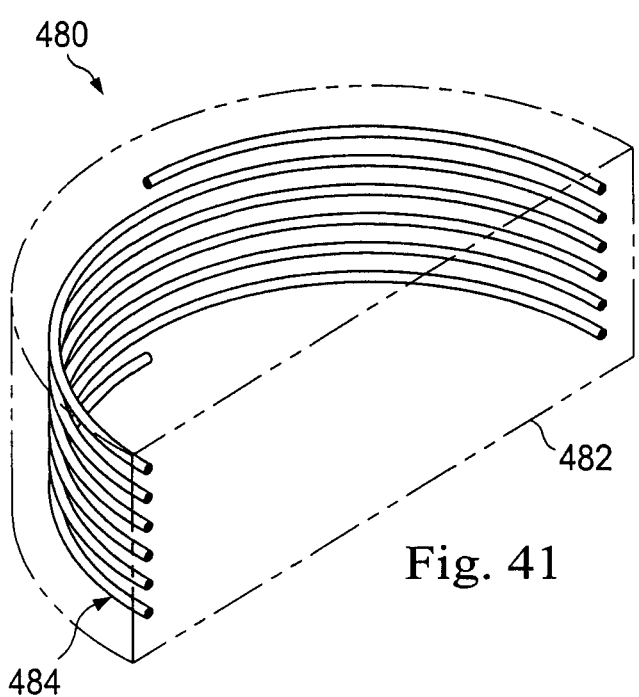
FIG. 41 is a diagrammatic partial perspective cross-sectional view of the material having a winded fiber configuration of FIG. 40 taken along section line 41-41.

Referring more specifically to FIGS. 40 and 41, shown therein is a representative material 480 having winded fiber configuration according to one aspect of the present disclosure. Specifically, FIG. 40 is a diagrammatic perspective view of the material 480 and FIG. 41 is a partial perspective cross-sectional view of the material 480 taken along section line 41-41 of FIG. 40. The material 480 includes a matrix material 482 imbedded with a plurality of fibers 484. In the present embodiment, the fibers 484 are disposed annularly within the matrix material 482. In some instances, each of the fibers 484 is wound around or into the material 482 to form the annular structure. In the present embodiment, the fibers 484 are substantially aligned within a vertical plane of the material such that the fibers generally define a cylindrical shape. In other embodiments, the fibers 484 may comprise alternative orientations and/or patterns. In that regard, the fibers are wound into oblong, rectangular, other geometrical, and/or other non-geometrical shapes in some instances. Further, in some instances, multiple groupings of fibers are disposed within the material. In one specific embodiment, multiple annular rings of fibers are disposed concentrically within the matrix material. Generally, the fibers may be wound into or around the matrix material 472 in any manner, orientation, or combination as desired.

In the illustrated embodiments of FIGS. 37-41, the matrix materials are illustrated as being at least partially translucent, while the fibers are illustrated as being substantially opaque such that the fibers are visible through the matrix material. In other instances, however, the matrix material is substantially opaque and/or the fibers are translucent and/or substantially the same color as the matrix material such that the fibers are not visible through the matrix material.

The composite materials described above may be utilized for forming prosthetic devices. For example, in some instances the composite materials are utilized for knee joints (including meniscus and total knee joints), hip joints (including acetabular cups), shoulder joints, elbow joints, finger joints, and other load bearing and/or non-load bearing prosthetic devices.

It should be appreciated that in some instances the prosthetic devices of the present disclosure are formed by other processes than those described herein. These manufacturing processes include any suitable manufacturing method. For example, without limitation any of the following manufacturing methods may be utilized: injection molding including inserting inserts; compression molding including inserting inserts; injection-compression molding including inserting inserts; compression molding of prefabricated elements preformed by any of the above methods including inserting inserts; spraying including inserting inserts; dipping including inserting inserts; machining from stocks or rods; machining from prefabricated elements including inserting inserts; and/or any of the above methods without inserts. Further, it should be appreciated that in some embodiments the prosthetic devices of the present disclosure are formed of medical grade materials other than those specifically identified above. In that regard, in some embodiments the prosthetic devices are formed of any suitable medical grade material.

While the principles of the present disclosure have been set forth using the specific embodiments discussed above, no limitations should be implied thereby. Any and all alterations or modifications to the described devices, instruments, and/or methods, as well as any further application of the principles of the present disclosure that would be apparent to one skilled in the art are encompassed by the present disclosure even if not explicitly discussed herein. It is also recognized that various presently unforeseen or unanticipated alternatives, modifications, and variations of the present disclosure may be subsequently made by those skilled in the art. All such variations, modifications, and improvements that would be apparent to one skilled in the art to which the present disclosure relates are encompassed by the following claims.

The invention claimed is:

1. A prosthetic device for replacing a damaged meniscus, the prosthetic device comprising:
   a body, comprising:
      a central portion, comprising:
         an upper articulating surface configured to contact a cooperating surface of a femur;
         a lower articulating surface configured to contact a cooperating surface of a tibia;
         an upper rim bounding the upper articulating surface; and
         a lower rim bounding the lower articulating surface; and
      an outer portion coupled to and surrounding the central portion, wherein at least one of the upper rim or the lower rim comprises an engagement surface configured to facilitate coupling of the outer portion and the central portion, wherein the body is configured to maintain positioning between the tibia and the femur in a knee joint without penetrating anatomy to secure the body within the knee joint; and
   a reinforcement member disposed within the body and configured to distribute load across the body.

2. The prosthetic device of claim 1, wherein the reinforcement member comprises a metal.

3. The prosthetic device of claim 1, wherein the upper articulating surface and the lower articulating surface comprise a polymer.

4. The prosthetic device of claim 1, wherein the reinforcement member comprises at least one fiber.

5. The prosthetic device of claim 4, wherein the at least one fiber is wound around the central portion.

6. The prosthetic device of claim 4, wherein a quantity of the at least one fiber varies along a height of the body.

7. The prosthetic device of claim 4, wherein a density of the at least one fiber varies along a height of the body.

8. The prosthetic device of claim 4, wherein the at least one fiber is distributed equally along a height of the body.

9. The prosthetic device of claim 4, wherein a ratio of an area associated with the at least fiber to an area associated with the body comprises a range from approximately 0.1% to approximately 1.2%.

10. The prosthetic device of claim 1, wherein the reinforcement member is disposed between the central portion and the outer portion.

11. The prosthetic device of claim 1, wherein the engagement surface comprises at least one of a projection, a recess, roughening, texturing, or knurling.

12. The prosthetic device of claim 1, wherein the outer portion is disposed between the upper rim and the lower rim.

13. The prosthetic device of claim 1, wherein the body comprises a biocompatible matrix material, and wherein the reinforcement member embedded within the biocompatible matrix material.

14. The prosthetic device of claim 13, wherein the reinforcement member is arranged in a geometric configuration within the biocompatible matrix material.

15. The prosthetic device of claim 14, wherein the geometric configuration comprises a linear pattern, a grid pattern, or an annular pattern.

16. The prosthetic device of claim 1, wherein:
   the upper articulating surface comprises a concave shape; and
   the lower articulating surface comprises a convex shape.

17. The prosthetic device of claim 1, wherein a smoothness of upper and lower surfaces of the outer portion is substantially similar to a smoothness of the upper articulating surface and the lower articulating surface.

* * * * *